United States Patent
Brooks et al.

(10) Patent No.: US 12,209,286 B2
(45) Date of Patent: Jan. 28, 2025

(54) METHODS OF DIAGNOSING, DETERMINING THE PROGRESSION OF, AND TREATING A PROSTATE CANCER

(71) Applicant: UNIVERSITY OF SOUTH AUSTRALIA, Adelaide (AU)

(72) Inventors: Doug Brooks, North Cheltenham (AU); Emma Parkinson-Lawrence, Morphettville (AU); Ian R. D. Johnson, Littlehampton (AU); Lisa Butler, Paradise (AU)

(73) Assignee: UNIVERSITY OF SOUTH AUSTRALIA, Adelaide (AU)

( * ) Notice: Subject to any disclaimer, the term of this patent is extended or adjusted under 35 U.S.C. 154(b) by 55 days.

(21) Appl. No.: 17/579,355

(22) Filed: Jan. 19, 2022

(65) Prior Publication Data
US 2022/0154292 A1    May 19, 2022

Related U.S. Application Data

(63) Continuation of application No. 15/794,270, filed on Jan. 23, 2018, now Pat. No. 11,261,496, which is a continuation of application No. 14/897,612, filed as application No. PCT/AU2014/000612 on Jun. 13, 2014, now abandoned.

(30) Foreign Application Priority Data

Jun. 13, 2013 (AU) .................................. 2013902141

(51) Int. Cl.
| | |
|---|---|
| G01N 33/574 | (2006.01) |
| C12Q 1/6886 | (2018.01) |
| A61N 5/10 | (2006.01) |
| C07K 14/47 | (2006.01) |
| C07K 14/705 | (2006.01) |
| C07K 16/18 | (2006.01) |
| C07K 16/28 | (2006.01) |
| C07K 16/30 | (2006.01) |

(52) U.S. Cl.
CPC ..... *C12Q 1/6886* (2013.01); *G01N 33/57434* (2013.01); *A61N 5/10* (2013.01); *C07K 14/4702* (2013.01); *C07K 14/70571* (2013.01); *C07K 16/18* (2013.01); *C07K 16/286* (2013.01); *C07K 16/3069* (2013.01); *C07K 2317/34* (2013.01); *C12Q 2600/106* (2013.01); *C12Q 2600/112* (2013.01); *C12Q 2600/118* (2013.01); *C12Q 2600/158* (2013.01); *G01N 2333/4703* (2013.01); *G01N 2333/82* (2013.01); *G01N 2333/96455* (2013.01); *G01N 2800/54* (2013.01)

(58) Field of Classification Search
CPC .............................................. G01N 33/57434
See application file for complete search history.

(56) References Cited

U.S. PATENT DOCUMENTS

| | | |
|---|---|---|
| 4,816,567 A | 3/1989 | Cabilly et al. |
| 5,639,641 A | 6/1997 | Pedersen et al. |
| 6,180,370 B1 | 1/2001 | Queen et al. |

FOREIGN PATENT DOCUMENTS

WO     92/22653 A1    12/1992

OTHER PUBLICATIONS

Mitsuuchi et al, 1999. Oncogene. 18: 4891-4898.*
Bae et al, 2011. Br J Haematol. 155(3): 349-361.*
Benjamini et al, 1991. Immunology: A Short Course, 2nd edition, p. 40 only.*
Kohler, et al., "Continuous cultures of fused cells secreting antibody of predefined specificity", Nature, vol. 256, pp. 495-497,1975.
Kozbor, et al., "Specific immunoglobulin production and enhanced tumorigenicity following ascites growth of human hybridomas", J. Immunol. Methods, vol. 81, pp. 31-42, 1985.
Cote, et al., "Generation of human monoclonal antibodies reactive with cellular antigens", Proc. Natl. Acad. Sci., vol. 80, pp. 2026-2030, 1983.
Cole, et al., "Human monoclonal antibodies", Mol. Cell Biol., vol. 62, pp. 109-120, 1984.
Gu, et al., "Construction and expression of mouse-human chimeric antibody SZ-51 specific for activated platelet P-selectin", Thrombosis and Haemostasis, vol. 77(4), pp. 755-759, 1997.
Morrison, et al., "Chimeric human antibody molecules: mouse antigen-binding domains with human constant region domains", Proc. Natl. Acad. Sci, vol. 81, pp. 6851-6855, 1984.
Neuberger, et al., "Recombinant antibodies possessing novel effector functions", Nature, vol. 312, pp. 604-608, 1984.
Takeda, et al., "Construction of chimaeric processed immunoglobulin genes containing mouse variable and human constant region sequences", Nature, vol. 314, pp. 452-454, 1985.
I. Johnson et al., "Altered Endosome Biogenesis in Prostate Cancer," Colloquia Abstract, ComBio2012, COL-03-01, Sep. 23-27, 2012, pp. 92.
Paul Mitchell et al., "Can urinary exosomes act as treatment response markers in prostate cancer?" Journal of Translational Medicine 2009, vol. 7, No. 4, pp. 1-13.
T. Kallunki et al., "Cancer-associated lysosomal changes: friends or foes?" Oncogene (2013) 32, pp. 1995-2004.
James P. Cherry et al., "Analysis of Cathepsin D Forms and Their Clinical Implications in Human Prostate Cancer," The Journal of Urology, vol. 160, pp. 2223-2228, Dec. 1998.
Yaron Mosesson et al., "Derailed endocytosis: an emerging feature of cancer," Nature Reviews: Cancer, vol. 8, Nov. 2008, pp. 835-850.
Stephanie Swift et al., "Altered Expression of Neurotensin Receptors Is Associated with the Differentiation State of Prostate Cancer," Tumor and Stem Cell Biology, Cancer Research 2010, vol. 70, No. 1, pp. 346-356.

(Continued)

*Primary Examiner* — Zachary C Howard
(74) *Attorney, Agent, or Firm* — BakerHostetler

(57) ABSTRACT

Methods for detecting a prostate cancer in a subject comprise detecting a marker selected from an endosomal associated marker and/or a lysosomal associated marker from the subject.

11 Claims, 47 Drawing Sheets

Specification includes a Sequence Listing.

(56) References Cited

OTHER PUBLICATIONS

Ceren G. Korkmaz et al., "Molecular cloning and characterization of STAMP2, an androgen-regulated six transmembrane protein that is overexpressed in prostate cancer," Oncogene 2005, vol. 24, No. 31, pp. 4934-4945.
Nicholas Turner et al., "Fibroblast growth factor signalling: from development to cancer," Nature Review Cancer Feb. 2010, vol. 10, No. 2, pp. 116-129.
Qian et al., "Identification and expression of two new secretory proteins associated with prostate cancer," Yi Chaun, 2010, vol. 32, No. 3, pp. 235-241.
Alicia Llorente et al., "Cholesterol regulates prostasome release from secretory lysosomes in PC-3 human prostate cancer cells," Euroepan Journal of Cell Biology 2007, vol. 86, No. 7, pp. 405-415.
Johanna Kiviniemi et al., "Altered expression of syndecan-1 in prostate cancer," APMIS 2004, vol. 112, pp. 89-97, 2004.
Binod Kumar et al., "Oxidative Stress is Inherent in Prostate Cancer Cells and is Required for Aggressive Phenotype," Cancer Research, vol. 68, No. 6, pp. 1777-1785, 2008.
Luz Canacho et al., "Acid ceramidase as a therapeutic target in metastatic prostate cancer," J. Lipid Res. May 2013, vol. 54, No. 5, pp. 1207-1220.
Sinha et al., "Plasma Membrane Association of Cathepsin B in Human Prostate Cancer: Biochemical and Immunogold Electron Microscopic Analysis," The Prostate, vol. 49, 2001, pp. 172-184.
C. Kelly et al., "Toll-like receptor 4 is not targeted to the lysosome in cystic fibrosis airway epithelial cells," Am J Physiol Lung Cell Mol Physiol, vol. 304, 2013, pp. L371-L382.
J. Wisniewski et al., "Extensive quantitative remodeling of the proteome between normal colon tissue and adenocarcinoma," Molecular Systems Biology, vol. 8, No. 611, 2012, pp. 1-12.
M. Jovic et al., "The early endosome: a busy sorting station for proteins at the crossroads," Histol Histopathol., vol. 25, No. 1, Jan. 2010, pp. 99-112.
Hood et al., "Proteomic Analysis of Formalin-Fixed Prostate Cancer Tissue," Molecular and Cellular Proteomics, vol. 4, 2005, pp. 1741-1753.
H. Miyake et al., "Serum Level of Cathepsin B and its Density in Men with Prostate Cancer as Novel Markers of Disease Progression," Anticancer Research, vol. 24, 2004, pp. 2573-2578.
Caspar, et al., "In Vitro Cultivation of Primary Prostate Cancer Cells Alters the Molecular Biomarker Pattern", In vivo, vol. 30, pp. 573-580, 2016.
Ferrara, et al., "Recombinant renewable polyclonal antibodies", mAbs, vol. 7, No. 1, pp. 32-41, 2015.
Yu, et al., "The diverse and contrasting effects of using human prostate cancer cell lines to study androgen receptor roles in prostate cancer", Asian Journal of Andrology, vol. 11, pp. 39-48, 2009.

* cited by examiner

Figure 26B

| Gene | P | HR | 95 % CI |
|---|---|---|---|
| M6PR | 0.182 | 0.716 | 0.337 – 1.486 |
| IGF2R | 0.073 | 1.938 | 0.938 – 4.041 |
| SORT1 | 0.010 | 2.732 | 1.246 – 5.343 |
| STEAP4 | 0.546 | 0.861 | 0.405 – 1.817 |
| MYO1B | 0.032 | 2.230 | 1.100 – 4.898 |
| PDCD6IP | 0.047 | 0.476 | 0.213 – 0.960 |
| SDC1 | 0.496 | 0.777 | 0.374 – 1.606 |
| SDCBP | 0.430 | 1.262 | 0.607 – 2.649 |

Figure 27B

| Gene | P | HR | 95 % CI |
|---|---|---|---|
| M6PR | 0.085 | 0.538 | 0.137 – 1.771 |
| IGF2R | 0.007 | 6.808 | 1.759 – 19.68 |
| SORT1 | 0.005 | 11.33 | 1.825 – 19.49 |
| STEAP4 | 0.828 | 1.209 | 0.282 – 5.094 |
| MYO1B | 0.072 | 2.205 | 0.673 – 7.273 |
| PDCD6IP | 0.045 | 0.288 | 0.053 – 0.797 |
| SDC1 | 0.302 | 0.476 | 0.146 – 1.565 |
| SDCBP | 0.814 | 1.178 | 0.362 – 3.846 |

SEQUENCE LISTING

<160> NUMBER OF SEQ ID NOS: 43

<210> SEQ ID NO 1
<211> LENGTH: 34
<212> TYPE: PRT
<213> ORGANISM: Homo sapiens

<400> SEQUENCE: 1

Ala Ser Asn Asp His Asp Ala Ala Ile Asn Arg Tyr Ser Arg Leu Ser
1               5                   10                  15

Lys Lys Arg Glu Asn Asp Lys Val Lys Tyr Glu Val Thr Glu Asp Val
            20                  25                  30

Tyr Thr

<210> SEQ ID NO 2
<211> LENGTH: 37
<212> TYPE: PRT
<213> ORGANISM: Homo sapiens

<400> SEQUENCE: 2

Asp Glu Val Ala Ser Asp Pro Leu Tyr Val Pro Asp Pro Asp Pro Thr
1               5                   10                  15

Lys Phe Pro Val Asn Arg Asn Leu Thr Arg Lys Ala Gly Tyr Leu Asn
            20                  25                  30

Ala Arg Asn Lys Thr
            35

<210> SEQ ID NO 3
<211> LENGTH: 29
<212> TYPE: PRT
<213> ORGANISM: Homo sapiens

<400> SEQUENCE: 3

Ser Glu Gly Gln Phe Val Val Leu Ser Ser Gln Ser Glu Glu Ser
1               5                   10                  15

Asp Leu Gly Glu Gly Gly Lys Lys Arg Glu Ser Glu Ala
            20                  25

<210> SEQ ID NO 4
<211> LENGTH: 35
<212> TYPE: PRT
<213> ORGANISM: Homo sapiens

<400> SEQUENCE: 4

Pro Asn Thr Phe Lys Thr Leu Asp Ser Trp Arg Asp Glu Phe Leu Ile
1               5                   10                  15

Gln Ala Ser Pro Arg Asp Pro Glu Asn Phe Pro Phe Val Val Leu Gly
            20                  25                  30

Asn Lys Ile
        35

<210> SEQ ID NO 5
<211> LENGTH: 35
<212> TYPE: PRT
<213> ORGANISM: Homo sapiens

<400> SEQUENCE: 5

Asp Pro Glu Asn Phe Pro Phe Val Val Leu Gly Asn Lys Ile Asp Leu
1               5                   10                  15

Glu Asn Arg Gln Val Ala Thr Lys Arg Ala Gln Ala Trp Cys Tyr Ser
            20                  25                  30

```
Lys Asn Asn
        35

<210> SEQ ID NO 6
<211> LENGTH: 35
<212> TYPE: PRT
<213> ORGANISM: Homo sapiens

<400> SEQUENCE: 6

Ala Leu Lys Gln Glu Thr Glu Val Glu Leu Tyr Asn Glu Phe Pro Glu
1               5                   10                  15

Pro Ile Lys Leu Asp Lys Asn Asp Arg Ala Lys Ala Ser Ala Glu Ser
            20                  25                  30

Cys Ser Cys
        35

<210> SEQ ID NO 7
<211> LENGTH: 15
<212> TYPE: PRT
<213> ORGANISM: Homo sapiens

<400> SEQUENCE: 7

Asn Arg Tyr Ser Arg Leu Ser Lys Lys Arg Glu Asn Asp Lys Val
1               5                   10                  15

<210> SEQ ID NO 8
<211> LENGTH: 15
<212> TYPE: PRT
<213> ORGANISM: Homo sapiens

<400> SEQUENCE: 8

Asp Pro Asp Pro Thr Lys Phe Pro Val Asn Arg Asn Leu Thr Arg
1               5                   10                  15

<210> SEQ ID NO 9
<211> LENGTH: 14
<212> TYPE: PRT
<213> ORGANISM: Homo sapiens

<400> SEQUENCE: 9

Gln Ser Glu Glu Ser Asp Leu Gly Glu Gly Gly Lys Lys Arg
1               5                   10

<210> SEQ ID NO 10
<211> LENGTH: 15
<212> TYPE: PRT
<213> ORGANISM: Homo sapiens

<400> SEQUENCE: 10

Arg Asp Glu Phe Leu Ile Gln Ala Ser Pro Arg Asp Pro Glu Asn
1               5                   10                  15

<210> SEQ ID NO 11
<211> LENGTH: 15
<212> TYPE: PRT
<213> ORGANISM: Homo sapiens

<400> SEQUENCE: 11

Gly Asn Lys Ile Asp Leu Glu Asn Arg Gln Val Ala Thr Lys Arg
1               5                   10                  15

<210> SEQ ID NO 12
<211> LENGTH: 15
```

<210> SEQ ID NO 12
<211> LENGTH: (not shown)
<212> TYPE: PRT
<213> ORGANISM: Homo sapiens

<400> SEQUENCE: 12

Tyr Asn Glu Phe Pro Glu Pro Ile Lys Leu Asp Lys Asn Asp Arg
1               5                   10                  15

<210> SEQ ID NO 13
<211> LENGTH: 19
<212> TYPE: PRT
<213> ORGANISM: Homo sapiens

<400> SEQUENCE: 13

Cys Lys Lys Leu Asp Asp Phe Val Glu Thr Gly Asp Ile Arg Thr Met
1               5                   10                  15
Val Phe Pro

<210> SEQ ID NO 14
<211> LENGTH: 20
<212> TYPE: DNA
<213> ORGANISM: Artificial Sequence
<220> FEATURE:
<223> OTHER INFORMATION: Primer Sequence

<400> SEQUENCE: 14
tgcaccacca actgcttagc                                          20

<210> SEQ ID NO 15
<211> LENGTH: 21
<212> TYPE: DNA
<213> ORGANISM: Artificial Sequence
<220> FEATURE:
<223> OTHER INFORMATION: Primer Sequence

<400> SEQUENCE: 15
ggcatggact gtggtcatga g                                        21

<210> SEQ ID NO 16
<211> LENGTH: 21
<212> TYPE: DNA
<213> ORGANISM: Artificial Sequence
<220> FEATURE:
<223> OTHER INFORMATION: Primer Sequence

<400> SEQUENCE: 16
acgttacagc gtccagctca t                                        21

<210> SEQ ID NO 17
<211> LENGTH: 19
<212> TYPE: DNA
<213> ORGANISM: Artificial Sequence
<220> FEATURE:
<223> OTHER INFORMATION: Primer Sequence

<400> SEQUENCE: 17
tctttggagc tcgcattgg                                           19

<210> SEQ ID NO 18
<211> LENGTH: 19
<212> TYPE: DNA
<213> ORGANISM: Artificial Sequence
<220> FEATURE:
<223> OTHER INFORMATION: Primer Sequence

<400> SEQUENCE: 18

-continued aaagcagcca agaggttcc                                            19

<210> SEQ ID NO 19
<211> LENGTH: 21
<212> TYPE: DNA
<213> ORGANISM: Artificial Sequence
<220> FEATURE:
<223> OTHER INFORMATION: Primer Sequence

<400> SEQUENCE: 19
gtctcccgtt tcaacaaagt c                                         21

<210> SEQ ID NO 20
<211> LENGTH: 23
<212> TYPE: DNA
<213> ORGANISM: Artificial Sequence
<220> FEATURE:
<223> OTHER INFORMATION: Primer Sequence

<400> SEQUENCE: 20
ggctacttgg gctattgtaa agg                                       23

<210> SEQ ID NO 21
<211> LENGTH: 23
<212> TYPE: DNA
<213> ORGANISM: Artificial Sequence
<220> FEATURE:
<223> OTHER INFORMATION: Primer Sequence

<400> SEQUENCE: 21
cagtttctcc gacaactttc tct                                       23

<210> SEQ ID NO 22
<211> LENGTH: 19
<212> TYPE: DNA
<213> ORGANISM: Artificial Sequence
<220> FEATURE:
<223> OTHER INFORMATION: Primer Sequence

<400> SEQUENCE: 22
cgtgcggaga ctctgtgtt                                            19

<210> SEQ ID NO 23
<211> LENGTH: 21
<212> TYPE: DNA
<213> ORGANISM: Artificial Sequence
<220> FEATURE:
<223> OTHER INFORMATION: Primer Sequence

<400> SEQUENCE: 23
atccaggtca ggctcatagt t                                         21

<210> SEQ ID NO 24
<211> LENGTH: 21
<212> TYPE: DNA
<213> ORGANISM: Artificial Sequence
<220> FEATURE:
<223> OTHER INFORMATION: Primer Sequence

<400> SEQUENCE: 24
acttgggtac atgcaagctc a                                         21

<210> SEQ ID NO 25
<211> LENGTH: 21
<212> TYPE: DNA
<213> ORGANISM: Artificial Sequence

```
<220> FEATURE:
<223> OTHER INFORMATION: Primer Sequence

<400> SEQUENCE: 25
tccctgcgaa cattctgaac g                                         21

<210> SEQ ID NO 26
<211> LENGTH: 20
<212> TYPE: DNA
<213> ORGANISM: Artificial Sequence
<220> FEATURE:
<223> OTHER INFORMATION: Primer Sequence

<400> SEQUENCE: 26
agctgatcgc gcctggaacg                                           20

<210> SEQ ID NO 27
<211> LENGTH: 21
<212> TYPE: DNA
<213> ORGANISM: Artificial Sequence
<220> FEATURE:
<223> OTHER INFORMATION: Primer Sequence

<400> SEQUENCE: 27
gggttggtac gcctgctccc t                                         21

<210> SEQ ID NO 28
<211> LENGTH: 22
<212> TYPE: DNA
<213> ORGANISM: Artificial Sequence
<220> FEATURE:
<223> OTHER INFORMATION: Primer Sequence

<400> SEQUENCE: 28
cccaacttgc tactgaaatt gc                                        22

<210> SEQ ID NO 29
<211> LENGTH: 22
<212> TYPE: DNA
<213> ORGANISM: Artificial Sequence
<220> FEATURE:
<223> OTHER INFORMATION: Primer Sequence

<400> SEQUENCE: 29
tgtcagacgt gtcacttttt gt                                        22

<210> SEQ ID NO 30
<211> LENGTH: 20
<212> TYPE: DNA
<213> ORGANISM: Artificial Sequence
<220> FEATURE:
<223> OTHER INFORMATION: Primer Sequence

<400> SEQUENCE: 30
agacccaacg ggccaaatac                                           20

<210> SEQ ID NO 31
<211> LENGTH: 22
<212> TYPE: DNA
<213> ORGANISM: Artificial Sequence
<220> FEATURE:
<223> OTHER INFORMATION: Primer Sequence

<400> SEQUENCE: 31
gccccaatgg tactctcttg aa                                        22
```

```
<210> SEQ ID NO 32
<211> LENGTH: 21
<212> TYPE: DNA
<213> ORGANISM: Artificial Sequence
<220> FEATURE:
<223> OTHER INFORMATION: Primer Sequence

<400> SEQUENCE: 32
attaaggcga ttgccacagt c                                              21

<210> SEQ ID NO 33
<211> LENGTH: 21
<212> TYPE: DNA
<213> ORGANISM: Artificial Sequence
<220> FEATURE:
<223> OTHER INFORMATION: Primer Sequence

<400> SEQUENCE: 33
tggtgctcat agtcacgaac t                                              21

<210> SEQ ID NO 34
<211> LENGTH: 21
<212> TYPE: DNA
<213> ORGANISM: Artificial Sequence
<220> FEATURE:
<223> OTHER INFORMATION: Primer Sequence

<400> SEQUENCE: 34
ggggctctcc tcgtctatga t                                              21

<210> SEQ ID NO 35
<211> LENGTH: 21
<212> TYPE: DNA
<213> ORGANISM: Artificial Sequence
<220> FEATURE:
<223> OTHER INFORMATION: Primer Sequence

<400> SEQUENCE: 35
agcgcattgt aggtttctcg g                                              21

<210> SEQ ID NO 36
<211> LENGTH: 22
<212> TYPE: DNA
<213> ORGANISM: Artificial Sequence
<220> FEATURE:
<223> OTHER INFORMATION: Primer Sequence

<400> SEQUENCE: 36
caacaagaag catccaggtt ga                                             22

<210> SEQ ID NO 37
<211> LENGTH: 22
<212> TYPE: DNA
<213> ORGANISM: Artificial Sequence
<220> FEATURE:
<223> OTHER INFORMATION: Primer Sequence

<400> SEQUENCE: 37
gcacctacag ctccacgata at                                             22

<210> SEQ ID NO 38
<211> LENGTH: 21
<212> TYPE: DNA
<213> ORGANISM: Artificial Sequence
<220> FEATURE:
<223> OTHER INFORMATION: Primer Sequence
```

```
<400> SEQUENCE: 38
tcggcgaatc aggtgtgggg a                                          21

<210> SEQ ID NO 39
<211> LENGTH: 20
<212> TYPE: DNA
<213> ORGANISM: Artificial Sequence
<220> FEATURE:
<223> OTHER INFORMATION: Primer Sequence

<400> SEQUENCE: 39
atggtggtgc ggctgtcgtg                                            20

<210> SEQ ID NO 40
<211> LENGTH: 23
<212> TYPE: DNA
<213> ORGANISM: Artificial Sequence
<220> FEATURE:
<223> OTHER INFORMATION: Primer Sequence

<400> SEQUENCE: 40
gtgttgctga aggttatcat cct                                        23

<210> SEQ ID NO 41
<211> LENGTH: 23
<212> TYPE: DNA
<213> ORGANISM: Artificial Sequence
<220> FEATURE:
<223> OTHER INFORMATION: Primer Sequence

<400> SEQUENCE: 41
gctcctattg tggctttgta ctg                                        23

<210> SEQ ID NO 42
<211> LENGTH: 20
<212> TYPE: DNA
<213> ORGANISM: Artificial Sequence
<220> FEATURE:
<223> OTHER INFORMATION: Primer Sequence

<400> SEQUENCE: 42
cctcattgcg cccagacggg                                            20

<210> SEQ ID NO 43
<211> LENGTH: 21
<212> TYPE: DNA
<213> ORGANISM: Artificial Sequence
<220> FEATURE:
<223> OTHER INFORMATION: Primer Sequence

<400> SEQUENCE: 43
agtgcaagag tgtctcgcgg c                                          21
```

METHODS OF DIAGNOSING, DETERMINING THE PROGRESSION OF, AND TREATING A PROSTATE CANCER

CROSS-REFERENCE TO RELATED APPLICATIONS

This application is a continuation of U.S. application Ser. No. 15/794,270, filed on Jan. 23, 2018, which is a continuation of U.S. application Ser. No. 14/897,612, filed on Dec. 10, 2015, and now abandoned, which is a National Stage of International patent application PCT/AU2014/000612, filed on Jun. 13, 2014, which claims priority to Australian provisional patent application number 2013902141 filed on Jun. 13, 2013, the contents of which are hereby incorporated by reference.

SEQUENCE LISTING

The instant application contains a Sequence Listing which has been submitted electronically in ASCII format and is hereby incorporated by reference in its entirety. Said ASCII copy, created on Feb. 1, 2022, is named SEQ.txt and is 12 kilobytes in size.

FIELD

The present invention relates to methods for detecting prostate cancer, methods for the diagnosis and/or prognosis of prostate cancer, methods for determining the progression of prostate cancer, methods for treating prostate cancer based on the detection of markers, and antibodies useful for diagnosis and/or prognosis of prostate cancer.

BACKGROUND

Prostate cancer is the most common form of cancer in males from developed countries, and the incidence of this disease is predicted to double globally by 2030. For example, in 2008 more than twenty thousand Australian men were diagnosed with prostate cancer, and there were nearly three thousand deaths, making this disease one of the largest causes of cancer-related deaths.

The prostate-specific antigen (PSA) test is currently used for prostate cancer screening, however, this assay suffers from a number of disadvantages, including a high percentage of false-positive results. PSA also cannot distinguish between aggressive or more slow-growing cancers at the time of diagnosis, resulting in over-treatment. Recently there have been recommendations to abandon this procedure, particularly in older men.

The digital rectal examination is an alternative procedure to check the prostate for abnormalities, but this test is limited by the inability to assess the whole gland and to some degree the size of the tumour.

There is therefore an urgent need for more specific and/or more accurate detection methods for prostate cancer, to assist in early diagnosis and selection of the most appropriate therapeutic interventions. Early detection significantly reduces mortality from prostate cancer, making improved diagnostic and prognostic methods an important objective.

Given the deficiencies associated with current techniques of diagnosis and/or prognosis of prostate cancer, the ability to utilise other biomarkers to assist in the detection of prostate cancer would be highly advantageous. However, the identification of clinically relevant biomarkers associated with prostate cancer remains problematic.

Accordingly, there remains a need to identify alternative biomarkers to detect prostate cancer and/or to provide one or more advantages in the art.

SUMMARY

The present disclosure is based on the determination that specific endosomal and/or lysosomal associated markers may be used to detect prostate cancer in a subject.

Certain embodiments of the present disclosure provide a method of detecting a prostate cancer in a subject, the method comprising detecting a marker selected from an endosomal associated marker and/or a lysosomal associated marker from the subject, thereby detecting a prostate cancer in the subject.

Certain embodiments of the present disclosure provide a method of detecting a prostate cancer in a subject, the method comprising detecting a marker selected from an endosomal associated marker and/or a lysosomal associated marker from the subject.

Certain embodiments of the present disclosure provide a method of detecting a prostate cancer in a subject, the method comprising detecting a marker selected from an endosomal associated marker and/or a lysosomal associated marker from the subject, wherein one or more of an altered presence, level, secretion and distribution of the selected marker is indicative of a prostate cancer in the subject.

Certain embodiments of the present disclosure provide a method of detecting a prostate cancer in a subject, the method comprising:
  obtaining a biological sample from the subject;
  processing the sample to allow detection of a marker selected from an endosomal associated marker and/or a lysosomal associated marker;
  detecting one or more of an altered presence, level, secretion and distribution of the selected marker in the processed sample; and
  identifying a prostate cancer in the subject.

Certain embodiments of the present disclosure provide a method of detecting a prostate cancer in a subject, the method comprising:
  obtaining a biological sample from the subject;
  processing the sample to allow detection of a marker selected from an endosomal associated marker and/or a lysosomal associated marker;
  detecting one or more of the presence, level, secretion and distribution of the selected marker in the processed sample;
  comparing one or more of the presence, level, secretion and distribution of the selected marker with one or more other markers known to be indicative of the presence or absence of prostate cancer in the subject; and
  identifying prostate cancer in the subject.

Certain embodiments of the present disclosure provide a method of identifying a subject suffering from or susceptible to a prostate cancer, the method comprising detecting a marker selected from an endosomal associated marker and/or a lysosomal associated marker from the subject.

Certain embodiments of the present disclosure provide a method of identifying a subject suffering from or susceptible to a prostate cancer, the method comprising detecting a marker selected from an endosomal associated marker and/or a lysosomal associated marker from the subject, wherein one or more of an altered presence, level, secretion and distribution of the selected marker is indicative that the subject is suffering from or susceptible to a prostate cancer.

Certain embodiments of the present disclosure provide a method of screening for a prostate cancer in a subject, the method comprising detecting a marker selected from an endosomal associated marker and/or a lysosomal associated marker from the subject.

Certain embodiments of the present disclosure provide a method of screening for a prostate cancer in a subject, the method comprising detecting a marker selected from an endosomal associated marker and/or a lysosomal associated marker from the subject, wherein one or more of an altered presence, level, secretion and distribution of the selected marker is indicative of prostate cancer in the subject.

Certain embodiments of the present disclosure provide method of treating a prostate cancer in a subject, the method comprising:
  detecting a marker selected from an endosomal associated marker and/or a lysosomal associated marker from the subject; and
  treating the subject based on one or more of the presence, level, secretion and distribution of the selected marker detected.

Certain embodiments of the present disclosure provide a method of diagnosis for detecting a prostate cancer in a subject, the method comprising detecting a marker selected from an endosomal associated marker and/or a lysosomal associated marker from the subject.

Certain embodiments of the present disclosure provide a method of determining the likelihood and/or risk of a subject suffering from, or being susceptible to, a prostate cancer, the method comprising detecting a marker selected from an endosomal associated marker and/or a lysosomal associated marker from the subject.

Certain embodiments of the present disclosure provide a method for determining the progression of a prostate cancer in a subject, the method comprising detecting a marker selected from an endosomal associated marker and/or a lysosomal associated marker from the subject.

Certain embodiments of the present disclosure provide a kit for performing a method as described herein.

Certain embodiments of the present disclosure provide a method of treating a prostate cancer in a subject, the method comprising:
  detecting a marker selected from an endosomal associated marker and/or a lysosomal associated marker from the subject; and
  treating the subject based on one or more of the presence, level, secretion and distribution of the selected marker detected.

Certain embodiments of the present disclosure provide an isolated or purified antibody raised to a polypeptide comprising an amino acid sequence of one or more of ASNDHDAAINRYSRLSKKRENDKVKYEVTEDVYT (SED ID NO. 1), DEVASDPLYVPDPDPTKFPVNRNL-TRKAGYLNARNKT (SEQ ID NO. 2), SEGQFVVLSSSQ-SEESDLGEGGKKRESEA (SEQ ID NO. 3), an antigenic fragment of any of the aforementioned amino acid sequences, and/or a variant of any of the aforementioned amino acid sequences or an antigenic fragment thereof.

Certain embodiments of the present disclosure provide an isolated and/or purified antibody binding to an epitope in an amino acid sequence in the human APPL1 protein comprising one or more of ASNDHDAAINRYSRL-SKKRENDKVKYEVTEDVYT (SED ID NO. 1), DEV-ASDPLYVPDPDPTKFPVNRNLTRKAGYLNARNKT (SEQ ID NO. 2), SEGQFVVLSSSQSEESDLGE GGKKRESEA (SEQ ID NO. 3), and/or an equivalent region of a homolog, ortholog or paralog of the protein.

Certain embodiments of the present disclosure provide an isolated and/or purified antibody raised to a polypeptide comprising an amino acid sequence of one or more of PNTFKTLDSWRDEFLIQASPRDPENFPFVVLGNKI (SED ID NO. 4), DPENFPFVVLGNKIDLENRQ-VATKRAQAWCYSKNN (SEQ ID NO. 5), ALKQETEV-ELYNEFPEPIKLDKNDRAKASAESCSC (SEQ ID NO. 6), an antigenic fragment of any of the aforementioned amino acid sequences, and/or a variant of any of the aforementioned amino acid sequences or an antigenic fragment thereof.

Certain embodiments of the present disclosure provide an isolated and/or purified antibody binding to an epitope in an amino acid sequence in the human RAB7 protein comprising one or more of PNTFKTLDSWRDE-FLIQASPRDPENFPFVVLGNKI (SED ID NO. 4), DPENFPFVVLGNKIDLENRQVATKRAQAWCYSKNN (SEQ ID NO. 5), ALKQETEVELYNEFPEPIKLDKN-DRAKASAESCSC (SEQ ID NO. 6), and/or an equivalent region of a homolog, ortholog or paralog of the protein.

Certain embodiments of the present disclosure provide a method of detecting an APPL1 protein or a fragment thereof, the method comprising using an APPL1 antibody as described herein.

Certain embodiments of the present disclosure provide a method of detecting a RAB7 protein or a fragment thereof, the method comprising using an RAB7 antibody as described herein.

Certain embodiments of the present disclosure provide a method of detecting a prostate cancer in a subject, the method comprising using an APPL1 antibody and/or a RAB7 antibody as described herein.

Certain embodiments of the present disclosure provide a method of identifying a selected marker for diagnosis and/or prognosis of a prostate cancer, the method comprising:
  identifying a marker selected from an endosomal associated marker and/or a lysosomal associated marker; and
  determining the ability of the selected marker to diagnose and/or prognose a prostate cancer;
  thereby identifying the marker as a selected marker for diagnosis and/or prognosis of a prostate cancer.

Other embodiments are disclosed herein.

BRIEF DESCRIPTION OF THE FIGURES

Certain embodiments are illustrated by the following figures. It is to be understood that the following description is for the purpose of describing particular embodiments only and is not intended to be limiting with respect to the description.

FIGS. 26A-26B show Kaplan-Meier analysis of endosome/lysosome-related genes and patient stratification based on biochemical recurrence (BCR).

FIGS. 27A-27B show Kaplan-Meier survival and multivariate analysis of endosomal-lysosomal gene expression for cancer patients expressing ≤7.8 ng/mL PSA.

DETAILED DESCRIPTION

Figure 1:
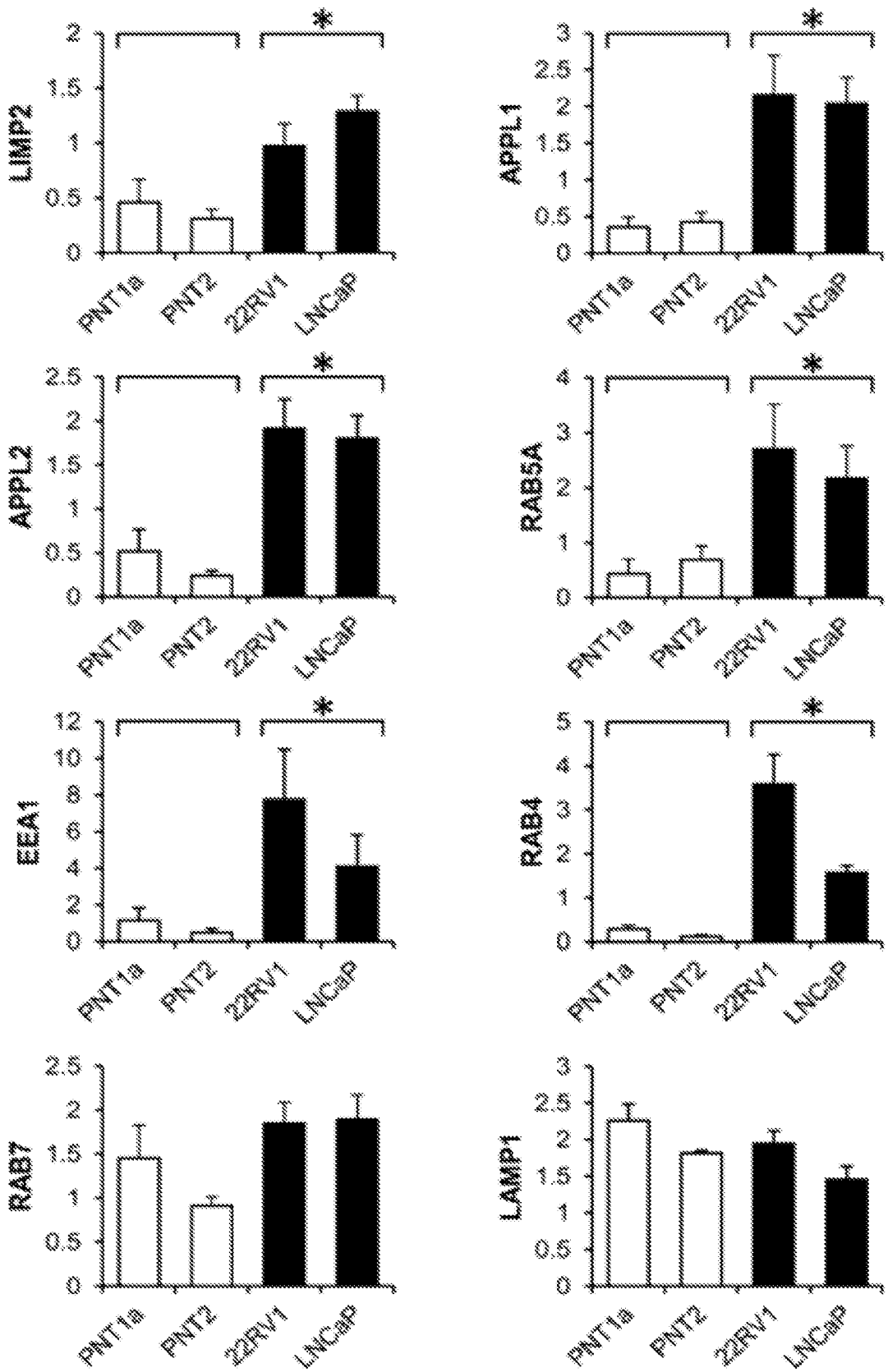
FIG. 1 shows quantification of endosomal and lysosomal gene expression in control and prostate cancer cell lines. Levels of mRNA transcripts in non-malignant control cell lines (white bars) and prostate cancer cell lines (black bars) were evaluated by qPCR in triplicate experiments. Data was expressed relative to GAPDH endogenous control and analysed by Kruskal-Wallis rank sum method. Statistical significance ($p<0.05$) is represented by an asterisk.

The present disclosure is based on the determination that specific endosomal associated and/or lysosomal associated markers may be used for the diagnosis and/or prognosis of prostate cancer.

Certain embodiments of the present disclosure provide methods for detecting a prostate cancer in a subject. Certain embodiments of the present disclosure provide methods for determining the progression of a prostate cancer in a subject. Certain embodiments of the present disclosure provide methods of treating prostate cancer in a subject based on use of selected markers. Other embodiments are disclosed herein.

Certain disclosed embodiments have one or more combinations of advantages. For example, some of the advantages of the embodiments disclosed herein include one or more of the following: the identification of a new class of markers for the diagnosis and/or prognosis of prostate cancer; one or more markers that in some instances may be used for both diagnosis and prognosis of prostate cancer; one or more markers that are readily detectable in a biological sample, such as in a tissue or biopsy sample, blood or plasma; use of one or more protein based markers; use of one or more nucleic acid based markers; one or more markers which may be used in conjunction with other types of markers; use of a method that is amenable to high throughput analysis of samples; use of a method that assists in identifying subjects suitable for pharmacological and/or surgical intervention to treat prostate cancer; markers that are suitable for use in kits; to address one or more problems in the art; to provide one or more advantages in the art; or to provide a useful commercial choice. Other advantages of certain embodiments are disclosed herein.

As described herein, the present disclosure is based on the determination that specific endosomal associated and/or lysosomal associated markers in a subject may be used to detect prostate cancer.

Further, certain embodiments of the present disclosure are based, at least in part, on the recognition that a unique change in the cell biology of early and late endosomes occurs in prostate cancer cells. Without being bound by theory, late endosomes normally form intra-luminal vesicles by invagination of their outer membrane (i.e. form small vesicles inside of the late endosome, also called multi vesicular bodies). These small internal ~100 nm vesicles can be released from normal cells when the late endosomes fuse with the cell surface, releasing their internal contents from the cell, together with these exosome vesicles. Because of the way that they are formed, exosomes can contain cytosolic proteins as well as endosome vesicular machinery. In normal controls early endosomal associated markers can therefore be released from cells and detected in the extracellular milieu/circulation. It has been found that there is a specific reduction in the release of early endosomal associated markers from prostate cancer cells when compared to control cells. More importantly, it has been discovered that: the vesicular machinery associated with different populations of early endosomes, are released from prostate cancer cells, suggesting that early endosomes may be able to form intra-luminal vesicles in prostate cancer cells; early endosomes fuse with the plasma membrane of prostate cancer cells and preferentially release these early endosome derived exosome vesicles; the process of endosome biogenesis is altered to form intra-luminal vesicles in early rather than late endosomes. This provides a unique set of changes to both early and late endosomes in prostate cancer cells and also provides a basis for a ratio when detecting biomarkers from these different endosome populations, which effectively identifies the changes in prostate cancer when compared to control cells.

Certain embodiments of the present disclosure provide methods and kits for detecting a prostate cancer in a subject.

Certain embodiments of the present disclosure provide a method of detecting a prostate cancer in a subject, the method comprising detecting a marker selected from an endosomal associated marker and/or a lysosomal associated marker from the subject.

Certain embodiments of the present disclosure provide a method of detecting a prostate cancer in a subject, the method comprising detecting a marker selected from an endosomal associated marker and/or a lysosomal associated marker from the subject, thereby detecting the prostate cancer in the subject.

Certain embodiments of the present disclosure provide a method of detecting a prostate cancer in a subject by detecting a marker selected from an endosomal associated marker and/or a lysosomal associated marker from the subject, thereby detecting the prostate cancer on the basis of the endosomal associated marker and/or the lysosomal associated marker so detected.

In certain embodiments, the prostate cancer is selected from a prostatic intraepithelial neoplasia, a primary prostate cancer, and a metastatic prostate cancer. Other forms and/or grades of prostate cancer are contemplated.

In this regard, typically the Gleason Grading system is used to evaluate a prostate cancer. A "score" is assigned to a prostate cancer on the basis of the combination of a "Gleason" pattern associated with various features of a tumor specimen and a subsequent grade assigned to the patterns of the tumour specimen. A Gleason score of 2-4 is considered to be a cancer of low aggressiveness. A score of 5-6 is considered to be a cancer of moderate aggressiveness. A score of 7 is considered to be a score of intermediate aggressiveness. A score of 8-10 is considered to be a cancer of high aggressiveness. In certain embodiments, the prostate cancer is a cancer with a Gleason score of any of the aforementioned scores.

Prostate cancers may also be categorised by stage, being a measure of how far a cancer has developed. In Stage 1, the cancer is small and contained within the prostate. In Stage 2, the cancer is larger and may be in both lobes of the prostate, but is still confined to the organ. In Stage 3, the cancer has spread beyond the prostate and may have invaded the adjacent lymph glands or seminal vesicles. In Stage 4, the cancer has spread to other organs, or to bone. In certain embodiments, the prostate cancer is a cancer with a staging of any of the aforementioned stages.

It will be appreciated that while the present disclosure is described with reference to detecting a prostate cancer in a human subject, the present disclosure contemplates detecting prostate cancer in an animal subject, and accordingly veterinary applications of the present disclosure are also contemplated.

In certain embodiments, the subject is suffering from a prostate cancer. Examples of prostate cancers are as described herein.

Certain embodiments of the present disclosure provide a method of detecting a subject suffering from a prostate cancer, the method comprising detecting a marker selected from an endosomal associated marker and/or a lysosomal associated marker from the subject.

In certain embodiments, the subject is a subject with an increased likelihood or risk of suffering from a prostate cancer. In certain embodiments, the subject is a subject susceptible to a prostate cancer. In certain embodiments, the subject is a subject with one or more risk factors associated with a prostate cancer. In certain embodiments, the subject is a subject with an unknown likelihood or risk of suffering prostate cancer.

In certain embodiments, the subject is a subject with a measured or known PSA level. Examples of PSA levels are as described herein, for example, as described in Example 8 herein. In certain embodiments the subject is a subject with one or more of the characteristics as described in one or more of the Figures and/or Examples.

In certain embodiments, the subject is suitable for treatment for a prostate cancer.

The term "associated marker" refers to a marker which is enriched in one or more particular tissues, cells, organelles, and/or cell compartments and as such can be used alone, or in combination with other markers, to assist in the identification of the tissue, cell, organelle, and/or cell compartment.

In certain embodiments, the endosomal associated marker and/or the lysosomal associated marker comprises one or more of an early endosomal marker, a late endosomal marker, a marker associated with endosomal biogenesis, a marker associated with endosomal trafficking and a marker associated with endosomal recycling. Other types of endosomal and lysosomal markers are contemplated. Methods for determining whether a marker is one of the aforementioned markers are known in the art.

In certain embodiments, the selected marker as described herein comprises a protein, a polypeptide, a fragment, a derivative or a processed form of the aforementioned proteins or polypeptides, a nucleic acid including a mRNA, a microRNA, a nuclear RNA, a rRNA, or a fragment, a processed or unprocessed form of the aforementioned RNAs, a lipid, a cell surface marker, a receptor, or a cofactor. Other types of markers are contemplated.

In certain embodiments, the selected marker is a protein marker, and/or a fragment, an antigenic fragment, a derivative or a processed form thereof. Methods for detecting proteins are known in the art and examples are also as described herein.

In certain embodiments, the selected marker is a RNA marker, typically a mRNA, and/or a fragment, a derivative or a processed form thereof. Methods for detecting mRNAs are known in the art and examples are also as described herein.

As described herein, in certain embodiments, the detection of a mRNA may require the production of a cDNA strand complementary to the mRNA.

In certain embodiments, the selected marker may be useful as a protein marker. In certain embodiments, the selected marker may be useful as a mRNA marker. In certain embodiments, the selected marker may be useful as a protein marker and a mRNA marker.

In certain embodiments, the selected marker comprises one or more of CATHEPSIN B, CAPTHESIN D, α-GALACTOSIDASE, RAB7, LIMP-1, LIMP-2, TFR1, TFR2, STAMP2, SORT1 (SORTILIN), APPL1, EEA-1, LAMP-1, RAB4, APPL2, RAB5, RAB11, MPR, PAP, ACTIN, M6PR, IGFR2, MYO1B, PDCD6IP, SDCBP, SDC1, STX7, STX12, FGF1, FGF2, FGF3, FGFR1, FGFR2, FGFR3, NOX2, NOX4, and/or a mRNA encoding one of the aforementioned, a fragment of one of the aforementioned, a derivative of one of the aforementioned, and a processed form of one of the aforementioned.

In certain embodiments, the selected marker comprises one or more markers as described in any of the examples and/or figures.

Certain embodiments of the present disclosure provide a method of detecting a prostate cancer in a subject, the method comprising detecting a marker selected from one or more of CATHEPSIN B, CAPTHESIN D, α-GALACTOSIDASE, RAB7, LIMP-1, LIMP-2, TFR1, TFR2, STAMP2, SORT1 (SORTILIN), APPL1, EEA-1, LAMP-1, RAB4, APPL2, RAB5, RAB11, MPR, PAP, ACTIN, M6PR, IGFR2, MYO1B, PDCD6IP, SDCBP, SDC1, STX7, STX12, FGF1, FGF2, FGF3, FGFR1, FGFR2, FGFR3, NOX2, NOX4, and/or a mRNA encoding one of the aforementioned, a fragment of one of the aforementioned, a derivative of one of the aforementioned, and a processed form of one of the aforementioned.

It will be appreciated that the selected markers of the present disclosure are referred to herein as the human forms of the selected markers. However, it will be appreciated that the detection and/or use of equivalent markers are also contemplated. Equivalent markers in other species may be readily identified by a person skilled in the art.

Methods for detecting markers are known in the art. Typically, a marker present in a subject is detected in a sample, or a processed form of a sample, taken from a subject. For example, methods for detecting proteins and RNAs are known and may be performed typically using commercially available products. General methods, including methods for protein and RNA detection, extraction and isolation are known, are as described in, for example, Ausubel et al., Current Protocols of Molecular Biology, John Wiley and Sons (1997), the entire contents of which is hereby incorporated by reference.

Methods for detection of proteins markers are known and include for example immunological detection methods such as immunobinding, immunoblotting (eg Western analysis), immunoprecipitation, immunoelectrophoresis, immunostaining, immunohistochemistry, spectrophotometry, enzyme assays, mass spectrometry, and microscopy. Other methods are contemplated.

Methods for detecting nucleic acids are known and include microarray analysis, blotting (Northern, Southern), in situ hybridization, RT-PCR, End-Point Stem-Loop Real-Time RT-PCR, miR-Q RT-PCR, (A)-Tailed Universal Reverse Transcription, RNA Amplification Profiling, cloning based methods, nanoparticle based methods, splinted ligation methods, padlock-probes and rolling-circle amplification, bead-based flow cytometric methods, bioluminescence RNA detection methods, molecular beacon methods, ribozyme methods, and quantitative LNA-ELF-FISH methods. Other methods are contemplated.

In certain embodiments, the detecting of RNA markers comprises reverse transcription. Methods for reverse transcribing RNAs are known in the art. In certain embodiments, the detecting of RNA markers comprises amplification of a nucleic acid. Methods for nucleic acid amplification are known in the art. In certain embodiments, the detecting of RNA markers comprises a polymerase chain reaction. In certain embodiments, the polymerase chain reaction comprises a quantitative polymerase chain reaction.

In certain embodiments, the detecting of RNA markers comprises binding or hybridization of nucleic acids to one or more target nucleic acids. In certain embodiments, the detecting of RNA markers comprises binding of nucleic acids to one or more target nucleic acids bound to a solid substrate, such as a chip. Methods for binding nucleic acids to target nucleic acids, including binding to nucleic acids bound to a solid substrate, are known.

In certain embodiments, the detecting of the selected marker comprises a polymerase chain reaction. In certain embodiments, the polymerase chain reaction comprises a quantitative polymerase chain reaction.

In certain embodiments, the detecting of the selected marker comprises immunological detection. In certain embodiments, the immunological detection comprises ELISA, staining with an antibody, immunohistochemistry, and/or flow cytometric detection. Methods involving immunological detection are known in the art.

In certain embodiments, the methods as described herein comprise detecting one or more of the presence, level, expression, secretion and distribution of the selected marker.

In certain embodiments, one or more of an altered presence, altered level, altered expression, altered secretion and altered distribution of the selected marker is indicative of a prostate cancer in the subject.

In certain embodiments, an increased level and/or an increased secretion of an endosomal associated marker is indicative of prostate cancer in the subject. In certain embodiments, a decreased level and/or a decreased secretion of an endosomal associated marker is indicative of prostate cancer in the subject.

In certain embodiments, an increased level and/or an increased secretion of a lysosomal associated marker is indicative of prostate cancer in the subject. In certain embodiments, a decreased level and/or a decreased secretion of a lysosomal associated marker is indicative of prostate cancer in the subject.

In certain embodiments, an increased level and/or an increased secretion of a protein marker is indicative of a prostate cancer in the subject. In certain embodiments, a decreased level and/or a decreased secretion of a protein marker is indicative of a prostate cancer in the subject.

In certain embodiments, an increased level of a mRNA marker is indicative of prostate cancer in the subject. In certain embodiments, a decreased level of a mRNA marker is indicative of prostate cancer in the subject.

In certain embodiments, an increased level and/or an increased secretion of an early endosomal marker is indicative of prostate cancer in the subject.

In certain embodiments, one or more of an increased level of RAB5 protein and/or mRNA, an increased secretion of RAB5 protein, an increased level of APPL1 protein and/or mRNA, an increased secretion of APPL1 protein, an increased level of EEA1 protein and/or mRNA, an increased secretion of EEA1 protein, an increased level of LIMP-2 protein and/or mRNA, an increased level of TFR1 protein and/or mRNA, an increased level of TFR2 protein and/or mRNA, an increased level of RAB4 protein and/or mRNA, an increased secretion of RAB4 protein, an increased level of APPL2 protein and/or mRNA, a decreased level of LAMP1 protein and/or mRNA, an increased secretion of RAB11 protein, a decreased secretion of RAB7 protein, a decreased level of CAPTHESIN B protein or mRNA, a decreased level of CAPTHESIN D protein or mRNA, an increased level of α-GALACTOSIDASE protein or mRNA, a decreased level of STX7 protein or mRNA, a decreased level of STX12 protein or mRNA, an increased secretion of PDCD6IP protein, a decreased secretion of SDCBP protein, a decreased secretion of SORT1 protein, a decreased level of FGF1 protein or mRNA, a decreased level of FGF2 protein or mRNA, an increased level of FGF3 protein or mRNA, a decreased level of FGFR1 protein or mRNA, a decreased level of FGFR2 protein or mRNA, an increased level of FGFR3 protein or mRNA, an increased level of NOX2 protein or mRNA, and increased level of NOX4 protein or mRNA, an increased nuclear and/or nucleoli level of APPL1 protein, an increased nuclear membrane level of RAB7 protein, and an enlarged LIMP2 protein positive vesicles, is indicative of prostate cancer in the subject.

In certain embodiments, an altered presence, altered level, altered expression, altered secretion and altered distribution of one or more markers is as compared to one or more of non-malignant tissue, prostatic intraepithelial neoplasia, primary prostate cancer and metastatic prostate cancer.

In certain embodiments, LIMP2 protein or mRNA is increased in prostatic intraepithelial neoplasia as compared non-malignant prostate, LAMP1 protein or mRNA is decreased in metastatic prostate cancer as compared prostatic intraepithelial neoplasia, LAMP1 protein or mRNA is increased in primary prostate cancer as compared to metastatic prostate cancer, CAPTHESIN B protein or mRNA is decreased in primary prostate cancer as compared to non-malignant tissue, CAPTHESIN B protein or mRNA is decreased in metastatic prostate cancer as compared to non-malignant prostate, ACID CERAMIDASE protein or mRNA is increased in prostatic intraepithelial neoplasia as compared to non-malignant prostate, ACID CERAMIDASE protein or mRNA is increased in prostatic intraepithelial neoplasia as compared to metastatic prostate cancer, ACID CERAMIDASE protein or mRNA is increased in primary prostate cancer as compared to metastatic prostate cancer, APPL1 protein or mRNA is increased in primary prostate cancer as compared to non-malignant tissue, APPL2 protein or mRNA is increased in prostatic intraepithelial neoplasia as compared to non-malignant prostate, APPL2 protein or mRNA is increased in primary prostate cancer as compared to non-malignant tissue, APPL2 protein or mRNA is increased in prostatic intraepithelial neoplasia as compared to metastatic prostate cancer, APPL2 protein or mRNA is increased in primary prostate cancer as compared to metastatic prostate cancer, RAB5 protein or mRNA is decreased in metastatic prostate cancer as compared to non-malignant prostate, EEA1 protein or mRNA is decreased in metastatic prostate cancer as compared non-malignant prostate, EEA1 protein or mRNA is decreased in prostatic intraepithelial neoplasia as compared to metastatic prostate cancer, RAB4A protein or mRNA is decreased in metastatic prostate cancer as compared to non-malignant prostate, RAB4A protein or mRNA is decreased in prostatic intraepithelial neoplasia as compared to metastatic prostate cancer, RAB4A protein or mRNA is decreased in prostatic intraepithelial neoplasia as compared to primary prostatic cancer, RAB4A protein or mRNA is decreased in primary prostate cancer as compared to metastatic prostate cancer, MYO1B protein or mRNA is increased in prostatic intraepithelial neoplasia as compared to metastatic prostate cancer, MYO1B protein or mRNA is decreased in metastatic prostate cancer as compared prostatic intraepithelial neoplasia, MYO1B protein or mRNA is decreased in metastatic prostate cancer as compared to primary prostate cancer, PDCD6IP protein or mRNA is decreased in prostatic intraepithelial neoplasia as compared to metastatic prostate cancer, PDCD6IP protein or mRNA is decreased in prostatic intraepithelial neoplasia as compared to non-malignant prostate, SDCBP protein or mRNA is decreased in metastatic prostate cancer as compared to primary prostate cancer, STX7 protein or mRNA is decreased in metastatic prostate cancer as compared to primary prostate cancer, FGFR1 protein or mRNA is increased in metastatic prostate cancer as compared prostatic intraepithelial neoplasia, FGFR2 protein or mRNA is decreased in primary prostate cancer as compared to non-malignant tissue, NOX2 protein or mRNA is increased in primary prostate cancer as compared to non-malignant tissue and NOX4 protein or mRNA is increased in metastatic prostate cancer as compared prostatic intraepithelial neoplasia.

In certain embodiments, the methods as described herein comprise obtaining a biological sample from the subject.

In certain embodiments, the methods as described herein comprise processing the biological sample to allow detection of the selected marker. In certain embodiments, the methods as described herein comprise processing a biological sample to allow detection of a marker as described herein and detecting the marker in the processed sample. In certain embodiments, the methods as described herein comprise obtaining a biological sample from the subject and processing the biological sample to allow detection of the selected marker.

The term "biological sample" refers to a sample obtained from the subject and/or a processed and/or treated form thereof. For example, the biological sample may be untreated, diluted, a derivative, an extract, a treated form, pre-cleared, filtered, desalted, concentrated, diluted, buffered, centrifuged, induced, pre-treated, processed to remove one or more components or impurities from the sample, sliced, fixed, adhered to a slide, or suitable combinations thereof. In certain embodiments, a selected marker is detected in the sample directly. In certain embodiments, a selected marker is detected in the sample after processing and/or treating. In certain embodiments, the sample is processed and/or treated prior to detecting the selected marker and/or concurrently with detecting the selected marker.

Examples of biological samples include one or more biological fluids, such as blood, plasma, urine, amniotic fluid, tears, saliva, hair, skin, and one or more tissue samples or a biopsy. Other types of biological samples are contemplated.

In certain embodiments, the biological sample comprises one or more of a blood sample, a plasma sample, a serum sample, a biopsy and a prostate tissue sample.

In certain embodiments, the biological sample comprises a biopsy or a tissue sample. Certain embodiments provide detecting the in situ level of a selected marker.

In certain embodiments, the selected marker comprises one or more blood markers, plasma markers, and/or serum markers. Certain embodiments provide detecting the circulating level of a selected marker.

In certain embodiments, the detecting comprises a qualitative determination. In certain embodiments, the detecting comprises a qualitative determination of whether the selected marker has one or more of an altered presence, an altered level, an altered expression, an altered secretion and an altered distribution. In certain embodiments, the detecting comprises a quantitative determination of whether the selected marker has one or more of an altered presence, an altered level, an altered expression, an altered secretion and an altered distribution.

In certain embodiments, the detecting comprises a qualitative determination. In certain embodiments, the detecting comprises a qualitative determination of whether the selected marker is present or absent. In certain embodiments, the detecting comprises a quantitative assessment of the level of the selected marker. For example, certain methods allow for the quantification of the concentration of the selected marker. Methods for the calculation or determination of the concentration of markers are known in the art.

Certain embodiments of the present disclosure comprise detecting two or more selected markers. Certain embodiments of the present disclosure comprise detecting three or more selected markers. Certain embodiments of the present disclosure comprise detecting four or more selected markers.

In certain embodiments, the methods of the present disclosure comprise detecting two or more of the selected markers. In certain embodiments, the methods comprise detecting three or more of the selected markers. In certain embodiments, the methods comprise detecting four or more of the selected markers.

Certain embodiments of the present disclosure comprise detecting two or more of the following selected markers: CATHEPSIN B, CAPTHESIN D, α-GALACTOSIDASE, RAB7, LIMP-1, LIMP-2, TFR1, TFR2, STAMP2, SORT1 (SORTILIN), APPL1, EEA-1, LAMP-1, RAB4, APPL2, RAB5, RAB11, MPR, PAP, ACTIN, M6PR, IGFR2, MYO1B, PDCD6IP, SDCBP, SDC1, STX7, STX12, FGF1, FGF2, FGF3, FGFR1, FGFR2, FGFR3, NOX2, NOX4 and/or a mRNA encoding one of the aforementioned, a fragment of one of the aforementioned, a derivative of one of the aforementioned, and a processed form of one of the aforementioned.

Certain embodiments of the present disclosure comprise detecting three or more of the following selected markers: CATHEPSIN B, CAPTHESIN D, α-GALACTOSIDASE, RAB7, LIMP-1, LIMP-2, TFR1, TFR2, STAMP2, SORT1 (SORTILIN), APPL1, EEA-1, LAMP-1, RAB4, APPL2, RAB5, RAB11, MPR, PAP, ACTIN, M6PR, IGFR2, MYO1B, PDCD6IP, SDCBP, SDC1, STX7, STX12, FGF1, FGF2, FGF3, FGFR1, FGFR2, FGFR3, NOX2, NOX4 and/or a mRNA encoding one of the aforementioned, a fragment of one of the aforementioned, a derivative of one of the aforementioned, and a processed form of one of the aforementioned.

Certain embodiments of the present disclosure comprise detecting four or more of the following selected markers: CATHEPSIN B, CAPTHESIN D, α-GALACTOSIDASE, RAB7, LIMP-1, LIMP-2, TFR1, TFR2, STAMP2, SORT1 (SORTILIN), APPL1, EEA-1, LAMP-1, RAB4, APPL2, RAB5, RAB11, MPR, PAP, ACTIN, M6PR, IGFR2, MYO1B, PDCD6IP, SDCBP, SDC1, STX7, STX12, FGF1, FGF2, FGF3, FGFR1, FGFR2, FGFR3, NOX2, NOX4 and/or a mRNA encoding one of the aforementioned, a fragment of one of the aforementioned, a derivative of one of the aforementioned, and a processed form of one of the aforementioned.

In certain embodiments, the methods as described herein comprise determining the ratio of the level of one selected marker to another selected marker.

In certain embodiments, an altered ratio is indicative of a prostate cancer in the subject. In certain embodiments, an altered ratio as compared to non-malignant tissue is indicative of a prostate cancer in the subject. Other forms of comparison between different types of prostate tissue are as described herein.

In certain embodiments, an increased ratio of an early endosomal marker to a late endosomal marker is indicative of prostate cancer in the subject. In certain embodiments, an increased ratio of an early endosomal marker to a late endosomal marker as compared to non-malignant tissue is indicative of a prostate cancer in the subject.

In certain embodiments, the methods of the present disclosure comprise detecting one or more other markers in addition to the selected marker.

In certain embodiments, the methods of the present disclosure provide use of one or more markers, control markers and/or reference markers, as described herein.

An alteration in the presence, level, expression, secretion and distribution of a marker is typically relative to the level of one or more corresponding markers, for example one or more corresponding proteins or mRNAs in one or more control subjects and/or one or more subjects known to have prostate cancer.

In certain embodiments, the methods as described herein comprise comparing the presence, level, expression, secretion and distribution of the selected marker with one or more other markers known to be indicative of a prostate cancer in a subject and/or known to be indicative of the absence of a cancer.

In certain embodiments, the methods as described herein comprise comparing the presence, level, expression, secretion and distribution of the selected marker to one or more reference and/or control markers.

In certain embodiments, the methods as described herein comprise comparing the presence and/or level of the selected marker with the presence and/or level of one or more other markers associated with an altered risk of prostate cancer and/or one or more other markers known to be indicative of the presence or absence of prostate cancer in the subject.

In certain embodiments, the reference marker comprises an endogenous marker. In certain embodiments, the reference marker comprises an exogenous marker. For example, a sample may be spiked with an exogenous reference marker.

In certain embodiments, the one or more other markers comprises prostate specific antigen (PSA).

In certain embodiments, the methods of the present disclosure comprise processing the biological sample to allow detection of the selected markers. In certain embodiments, the methods of the present disclosure comprise processing a biological sample obtained from the subject to allow detection of the selected marker. Subjects are as described herein.

In certain embodiments, the methods and kits as described herein comprise use of one or more reagents for processing a sample for analysis.

In certain embodiments, the methods as described herein further comprise obtaining information relating to one or more clinical characteristics of the subject and using the information in combination with one or more of the presence, level, secretion and distribution of the selected marker to detect prostate cancer in the subject. In certain embodiments, the one or more clinical characteristics comprise one or more of age, body mass index, smoking, genetics and family history of cancer and/or prostate cancer.

In certain embodiments, the methods as described herein further comprise obtaining information relating to one or more clinical characteristics of the subject and using the information in combination with one or more of the presence, level, expression secretion and distribution of the selected marker to detect prostate cancer in the subject or the absence of prostate cancer.

In certain embodiments, the methods as described herein comprise using a computer processor means to process data associated with one or more of the presence, level, secretion and distribution of the selected marker to generate a likelihood and/or risk of the presence of prostate cancer in the subject. Examples of computer processor means are known.

In certain embodiments, the methods have a sensitivity of detection of 0.60 or greater. In certain embodiments, the methods have a sensitivity of detection of 0.70 or greater. In certain embodiments, the methods have a sensitivity of detection of 0.80 or greater. In certain embodiments, the methods have a sensitivity of detection of 0.90 or greater. In certain embodiments, the methods have a sensitivity of detection of 0.95 or greater.

In certain embodiments, the methods have a specificity of detection of 0.60 or greater. In certain embodiments, the methods have a specificity of detection of 0.70 or greater. In certain embodiments, the methods have a specificity of detection of 0.80 or greater. In certain embodiments, the methods have a specificity of detection of 0.90 or greater. In certain embodiments, the methods have a specificity of detection of 0.95 or greater.

In certain embodiments, the methods as described herein are used to diagnose prostate cancer in the subject, to screen for prostate cancer in the subject, for assessing prognosis, to determine the metastatic potential of a prostate cancer, to identify a subject suffering from prostate cancer, to identify a subject susceptible to prostate cancer, to determine the rate of relapse of prostate cancer in the subject, to determine the risk of mortality from prostate cancer in the subject, to stratify the prostate cancer, to discriminate between prostate cancer and not having prostate cancer in the subject, to determine whether the prostate cancer is an organ confined cancer, to discriminate between prostate cancer and one or more of benign prostatic hyperplasia, prostatitis and an inflammatory condition of the prostate, to determine pathogenic progression, to assess whether the prostate cancer is slow growing, indolent, or aggressive, to exclude the presence of prostate cancer in the subject, to identify a subject suitable for treatment and/or surgery for prostate cancer, and to determine the likelihood or risk of a subject having prostate cancer.

Certain embodiments of the present disclosure provide a method of detecting a prostate cancer in a subject, the method comprising:
  obtaining a biological sample from the subject;
  processing the sample to allow detection of a marker selected from an endosomal associated marker and/or a lysosomal associated marker;
  detecting one or more of an altered presence, level, expression, secretion and distribution of the selected marker in the processed sample; and
  identifying a prostate cancer in the subject.

Certain embodiments of the present disclosure provide a method of detecting a prostate cancer in a subject, the method comprising:

obtaining a biological sample from the subject;
processing the sample to allow detection of a marker in the sample;
detecting one or more of CATHEPSIN B, CAPTHESIN D, α-GALACTOSIDASE, RAB7, LIMP-1, LIMP-2, TFR1, TFR2, STAMP2, SORT1 (SORTILIN), APPL1, EEA-1, LAMP-1, RAB4, APPL2, RAB5, RAB11, MPR, PAP, ACTIN, M6PR, IGFR2, MYO1B, PDCD6IP, SDCBP, SDC1, STX7, STX12, FGF1, FGF2, FGF3, FGFR1, FGFR2, FGFR3, NOX2, NOX4, and/or a mRNA encoding one of the aforementioned, a fragment of one of the aforementioned, a derivative of one of the aforementioned, and a processed form of one of the aforementioned for an altered presence, level, expression, secretion and distribution of the selected marker in the processed sample; and
identifying prostate cancer in the subject.

Certain embodiments of the present disclosure provide a method of detecting prostate cancer in a subject substantially as described herein with reference to any of the accompanying examples and/or figures.

Certain embodiments of the present disclosure provide a method or kit for identifying a subject suffering from, or susceptible to, a prostate cancer.

Certain embodiments of the present disclosure provide a method of identifying a subject suffering from or susceptible to a prostate cancer, the method comprising detecting a marker selected from an endosomal associated marker and/or a lysosomal associated marker from the subject.

Certain embodiments of the present disclosure provide a method of identifying a subject suffering from, or susceptible to, a prostate cancer, the method comprising detecting a marker selected from an endosomal associated marker and/or a lysosomal associated marker from the subject, wherein one or more of an altered presence, level, expression, secretion and distribution of the selected marker is indicative that the subject is suffering from, or susceptible to, a prostate cancer.

Certain embodiments of the present disclosure provide a method of identifying a subject suffering from or susceptible to a prostate cancer in a subject, the method comprising detecting a marker from the subject as hereinbefore described with reference to any of the examples and/or figures.

Certain embodiments of the present disclosure provide methods or kits for screening for a prostate cancer in a subject.

Certain embodiments of the present disclosure provide a method of screening for a prostate cancer in a subject, the method comprising detecting a marker selected from an endosomal associated marker and/or a lysosomal associated marker from the subject.

In certain embodiments, the method is used to identify a subject suffering from, or susceptible to, a prostate cancer.

In certain embodiments, the method is used to exclude a subject not suffering from, or not susceptible to, a prostate cancer.

Certain embodiments of the present disclosure provide a method of screening for a prostate cancer in a subject, the method comprising detecting a marker selected from an endosomal associated marker and/or a lysosomal associated marker from the subject, wherein one or more of an altered presence, level, expression, secretion and distribution of the selected marker is indicative of a prostate cancer in the subject.

Certain embodiments of the present disclosure provide a method of screening for a prostate cancer in a subject, the method comprising detecting a marker from the subject as hereinbefore described with reference to any of the examples and/or figures.

Certain embodiments of the present disclosure provide a method or kit for diagnosis of a prostate cancer in a subject.

Certain embodiments of the present disclosure provide a method of diagnosis for detecting a prostate cancer in a subject, the method comprising detecting a marker selected from an endosomal associated marker and/or a lysosomal associated marker from the subject.

Certain embodiments of the present disclosure provide a method or kit for determining the likelihood and/or risk of a subject suffering from, or being susceptible to, a prostate cancer.

Certain embodiments of the present disclosure provide a method of determining the likelihood and/or risk of a subject suffering from, or being susceptible to, a prostate cancer, the method comprising detecting a marker selected from an endosomal associated marker and/or a lysosomal associated marker from the subject.

Certain embodiments of the present disclosure provide a method or kit for determining the progression of a prostate cancer in a subject.

Certain embodiments of the present disclosure provide a method for determining the progression of a prostate cancer in a subject, the method comprising detecting a marker selected from an endosomal associated marker and/or a lysosomal associated marker from the subject.

In certain embodiments, the method comprises determining biochemical recurrence of the cancer, relapse rate and/or survival rate.

In certain embodiments, the level of the marker is indicative of a reduced relapse rate and/or increased survival rate.

In certain embodiments, the marker comprises one or more of LIMP2, CATHEPSIN B, CAPTHESIN D, α-GALACTOSIDASE, RAB5A, EEA1, RAB7A, M6PR, IGFR2, SORT1, MYO1B, PDCD6IP, SDC1, STX12, FGF2, FGF3 and/or a mRNA encoding one of the aforementioned, a fragment of one of the aforementioned, a derivative of one of the aforementioned, and a processed form of one of the aforementioned.

In certain embodiments, the marker comprises one or more of decreased or lower LIMP2, increased or higher CATHEPSIN B, increased or higher CAPTHESIN D, increased or higher α-GALACTOSIDASE, decreased or lower RAB5A, decreased or lower EEA1, increased or higher RAB7A, increased or higher M6PR, decreased or lower IGFR2, decreased or lower SORT1, decreased or lower MYO1B, increased or higher PDCD6IP, increased or higher STX12, increased or higher FGF2, increased or higher FGF3 and/or a mRNA encoding one of the aforementioned, a fragment of one of the aforementioned, a derivative of one of the aforementioned, and a processed form of one of the aforementioned.

In certain embodiments, the method further comprises identifying the level of PSA expression in the subject and stratifying the expression of the marker on the basis of the PSA expression level in the subject. PSA levels are as described herein.

In certain embodiments, the PSA is a level indicative of a low risk of a prostate cancer. In certain embodiments, the PSA level is less than 10 ng/ml.

In certain embodiments, the PSA is a level of 7.8 ng/ml or less. In certain embodiments, the marker comprises one or more of LIMP2, CATHEPSIN B, α-GALACTOSIDASE, RAB5A, EEA1, M6PR, IGFR2, SORT1, MYO1B, PDCD6IP, SDC1, STX12, FGF2, FGF3 and/or a mRNA encoding one of the aforementioned, a fragment of one of the aforementioned, a derivative of one of the aforementioned, and a processed form of one of the aforementioned.

In certain embodiments, the marker comprises one or more of decreased or lower LIMP2, increased or higher CATHEPSIN B, increased or higher α-GALACTOSIDASE, decreased or lower RAB5A, decreased or lower EEA1, increased or higher M6PR, decreased or lower IGFR2, decreased or lower SORT1, decreased or lower MYO1B, increased or higher PDCD6IP, increased or higher SDC1, increased or higher STX12, increased or higher FGF2, increased or higher FGF3 and/or a mRNA encoding one of the aforementioned, a fragment of one of the aforementioned, a derivative of one of the aforementioned, and a processed form of one of the aforementioned.

In certain embodiments, the level of the marker is indicative of an increased relapse rat and/or decreased survival rate. In certain embodiments, the marker comprises one or more of LIMP2, CATHEPSIN B, CAPTHESIN D, α-GALACTOSIDASE, RAB5A, EEA1, RAB7A, M6PR, IGFR2, SORT1, MYO1B, PDCD6IP, SDC1, STX12, FGF2, FGF3 and/or a mRNA encoding one of the aforementioned, a fragment of one of the aforementioned, a derivative of one of the aforementioned, and a processed form of one of the aforementioned.

In certain embodiments, the marker comprises one or more of increased or higher LIMP2, decreased or lower CATHEPSIN B, decreased or lower CAPTHESIN D, decreased or lower α-GALACTOSIDASE, increased or higher RAB5A, increased or higher EEA1, decreased or lower RAB7A, decreased or lower M6PR, increased or higher IGFR2, increased or higher SORT1, increased or higher MYO1B, decreased or lower PDCD6IP, decreased or lower STX12, decreased or lower FGF2, decreased or lower FGF3 and/or a mRNA encoding one of the aforementioned, a fragment of one of the aforementioned, a derivative of one of the aforementioned, and a processed form of one of the aforementioned.

In certain embodiments, the method further comprises identifying the level of PSA expression in the subject and stratifying the expression of the marker on the basis of the PSA expression level in the subject. In certain embodiments, the PSA is a level indicative of a low risk of prostate cancer. In certain embodiments, the PSA level is less than 10 ng/ml. In certain embodiments, the PSA is a level of 7.8 ng/ml or less.

In certain embodiments, the marker comprises one or more of LIMP2, CATHEPSIN B, α-GALACTOSIDASE, RAB5A, EEA1, M6PR, IGFR2, SORT1, MYO1B, PDCD6IP, SDC1, STX12, FGF2, FGF3 and/or a mRNA encoding one of the aforementioned, a fragment of one of the aforementioned, a derivative of one of the aforementioned, and a processed form of one of the aforementioned.

In certain embodiments, the marker comprises one or more of increased or higher LIMP2, decreased or lower CATHEPSIN B, decreased or lower α-GALACTOSIDASE, increased or higher RAB5A, increased or higher EEA1, decreased or lower M6PR, increased or higher IGFR2, increased or higher SORT1, increased or higher MYO1B, decreased or lower PDCD6IP, decreased or lower SDC1, decreased or lower STX12, decreased or lower FGF2, decreased or lower FGF3 and/or a mRNA encoding one of the aforementioned, a fragment of one of the aforementioned, a derivative of one of the aforementioned, and a processed form of one of the aforementioned.

Certain embodiments of the present disclosure provide a kit for performing a method as described herein. The kits may comprise one or more components, reagents, and/or instructions as described herein.

In certain embodiments, the kit comprises one or more reagents and/or instructions for determining the presence, level, expression, secretion and distribution of a selected marker.

Certain embodiments of the present disclosure provide a method of treating a prostate cancer.

The term "treating", and related terms such as "treatment" and "treat", refer to obtaining a desired effect in terms of improving the condition of the subject, ameliorating, arresting, suppressing, relieving and/or slowing the progression of one or more symptoms in the subject, a partial or complete stabilization of the subject, a regression of the one or more symptoms, or a cure of a disease, condition or state in the subject.

Certain embodiments of the present disclosure provide a method of treating a prostate cancer in a subject, the method comprising:

detecting a marker selected from an endosomal associated marker and/or a lysosomal associated marker from the subject; and treating the subject based on one or more of the presence, level, secretion and distribution of the selected marker detected.

Certain embodiments of the present disclosure provide method of treating a prostate cancer in a subject, the method comprising:

detecting a marker as described herein; and treating the subject based on one or more of the presence, level, secretion and distribution of the marker so detected.

In certain embodiments, the treating comprising one or more of surgical intervention, radiation therapy and administration of a therapeutic agent.

Certain embodiments of the present disclosure provide a method of treating a prostate cancer by surgical intervention to a subject based on one or more of the presence, level, expression, secretion and distribution of the selected marker detected, as described herein. Methods of surgical intervention for prostate cancer are known in the art.

Certain embodiments of the present disclosure provide a method of treating a prostate cancer by administering to a subject an effective amount of a therapeutic agent based on one or more of the presence, level, expression, secretion and distribution of the selected marker detected, as described herein. Methods of pharmacological intervention for prostate cancer are known in the art.

Certain embodiments of the present disclosure provide a method of treating a prostate cancer by radiation therapy based on one or more of the presence, level, expression, secretion and distribution of the selected marker detected, as described herein. Methods of radiation therapy for prostate cancer are known in the art.

In certain embodiments, the treatment occurs when one or more of the presence, level, expression, secretion and distribution presence of the selected marker is indicative of the presence of prostate cancer and/or an increased likelihood or risk of prostate cancer, as described herein.

In certain embodiments, one or more of an altered presence, level, expression secretion and distribution level of the selected marker is indicative that the subject is suitable for treatment. Alterations in the presence, level, expression, secretion, and distribution are as described herein.

In certain embodiments, an increased level of the selected marker is indicative that the subject is suitable for treatment. In certain embodiments, a decreased level of the selected marker is indicative that the subject is suitable for treatment. In certain embodiments, a down regulation of selected marker is indicative that the subject is suitable for treatment. In certain embodiments, an up regulation of the selected marker is indicative that the subject is suitable for treatment. In certain embodiments, a down regulation of one selected marker and/or an up-regulation of another selected marker is indicative that the subject is suitable for treatment.

As described herein, certain embodiments of the present disclosure provide methods as follows: to diagnose prostate cancer in the subject, to screen for prostate cancer in the subject, for assessing prognosis, to determine the metastatic potential of a prostate cancer, to identify a subject suffering from prostate cancer, to identify a subject susceptible to prostate cancer, to determine the rate of relapse of prostate cancer in the subject, to determine the risk of mortality from prostate cancer in the subject, to stratify the prostate cancer, to discriminate between prostate cancer and not having prostate cancer in the subject, to determine whether the prostate cancer is an organ confined cancer, to discriminate between prostate cancer and one or more of benign prostatic hyperplasia, prostatitis and an inflammatory condition of the prostate, to determine pathogenic progression, to assess whether the prostate cancer is slow growing, indolent, or aggressive, to exclude the presence of prostate cancer in the subject, to identify a subject suitable for treatment and/or surgery for prostate cancer, and to determine the likelihood or risk of a subject having prostate cancer. Endosomal associated markers and/or lysosomal associated markers are as described herein. Methods for detecting markers are as described herein.

Certain embodiments of the present disclosure provide a method or kit for assessing prognosis of a subject susceptible to or suffering from a prostate cancer, the method comprising detecting a marker selected from an endosomal associated marker and/or a lysosomal associated marker from the subject.

Certain embodiments of the present disclosure provide a method or kit to determine the metastatic potential of a prostate cancer in a subject, the method comprising detecting a marker selected from an endosomal associated marker and/or a lysosomal associated marker from the subject.

Certain embodiments of the present disclosure provide a method or kit to determine the rate of relapse of a prostate cancer in a subject, the method comprising detecting a marker selected from an endosomal associated marker and/or a lysosomal associated marker from the subject.

Certain embodiments of the present disclosure provide a method or kit to determine the risk of mortality from a prostate cancer in a subject, the method comprising detecting a marker selected from an endosomal associated marker and/or a lysosomal associated marker from the subject.

Certain embodiments of the present disclosure provide a method or kit to stratify a prostate cancer in a subject, the method comprising detecting a marker selected from an endosomal associated marker and/or a lysosomal associated marker from the subject.

Certain embodiments of the present disclosure provide a method or kit to discriminate between a subject having a prostate cancer and not having a prostate cancer, the method comprising detecting a marker selected from an endosomal associated marker and/or a lysosomal associated marker from the subject.

Certain embodiments of the present disclosure provide a method or kit to determine whether a prostate cancer is an organ confined cancer in a subject, the method comprising detecting a marker selected from an endosomal associated marker and/or a lysosomal associated marker from the subject.

Certain embodiments of the present disclosure provide a method or kit to discriminate between a prostate cancer and one or more of benign prostatic hyperplasia, prostatitis and an inflammatory condition of the prostate in a subject, the method comprising detecting a marker selected from an endosomal associated marker and/or a lysosomal associated marker from the subject.

Certain embodiments of the present disclosure provide a method or kit to determine pathogenic progression of a prostate cancer in a subject, the method comprising detecting a marker selected from an endosomal associated marker and/or a lysosomal associated marker from the subject.

Certain embodiments of the present disclosure provide a method or kit to assess whether a prostate cancer in a subject is slow growing, indolent, or aggressive, the method comprising detecting a marker selected from an endosomal associated marker and/or a lysosomal associated marker from the subject.

Certain embodiments of the present disclosure provide a method or kit to exclude the presence of a prostate cancer in a subject, the method comprising detecting a marker selected from an endosomal associated marker and/or a lysosomal associated marker from the subject.

Certain embodiments of the present disclosure provide a method or kit to identify a subject suitable for treatment and/or surgery for prostate cancer, the method comprising detecting a marker selected from an endosomal associated marker and/or a lysosomal associated marker from the subject.

Certain embodiments of the present disclosure provide a method or kit to determine the likelihood or risk of a subject having a prostate cancer, the method comprising detecting a marker selected from an endosomal associated marker and/or a lysosomal associated marker from the subject.

Certain embodiments of the present disclosure provide a method or kit for identifying a selected marker for diagnosis and/or prognosis of a prostate cancer. Certain embodiments of the present disclosure provide a method of screening for a selected marker for diagnosis and/or prognosis of a prostate cancer.

Methods for identifying and/or screening markers are as described herein.

Certain embodiments of the present disclosure provide a method of identifying a selected marker for diagnosis and/or prognosis of a prostate cancer, the method comprising:

identifying a marker selected from an endosomal associated marker and/or a lysosomal associated marker; and
determining the ability of the selected marker to diagnose and/or prognose a prostate cancer;
thereby identifying the marker as a selected marker for diagnosis and/or prognosis of a prostate cancer.

Certain embodiments of the present disclosure provide markers identified according to a method as described herein for use in diagnosis and/or prognosis of a prostate cancer.

Certain embodiments of the present disclosure provide isolated and/or purified antibodies, and/or antigen binding fragments thereof. Antibodies and fragments thereof are as described herein. Antibodies, and antigen binding fragments thereof, may be used for example to detect a prostate cancer, such as for use in kits as described herein.

The term "antibody" is to be understood to mean an immunoglobulin molecule with the ability to bind an antigenic region of another molecule, and includes monoclonal antibodies, polyclonal antibodies, multivalent antibodies, chimeric antibodies, multi specific antibodies, diabodies and fragments of an immunoglobulin molecule or combinations thereof that have the ability to bind to the antigenic region of another molecule with the desired affinity including a Fab, Fab', F(ab')2, Fv, a single-chain antibody (scFv) or a polypeptide that contains at least a portion of an immunoglobulin (or a variant of an immunoglobulin) that is sufficient to confer specific antigen binding, such as a molecule including one or more Complementarity Determining Regions (CDRs).

In certain embodiments, the antibody (or antigen binding fragment thereof) comprises an affinity of at least $10^6$ $M^{-1}$, at least $10^7$ $M^{-1}$, at least $10^8$ $M^{-1}$, at least $10^9$ $M^{-1}$, at least $10^{10}$ $M^{-1}$, at least $10^{11}$ $M^{-1}$, or at least $10^{12}$ $M^{-1}$ to the antigen.

Antibodies may be generated using known methods in the art. For the production of antibodies, various hosts including goats, rabbits, rats, mice, humans, and others, may be immunized by injection with an appropriate antigen. Depending on the host species, various adjuvants may be used to increase an immunological response. Such standard adjuvants include Freund's adjuvant, mineral gels such as aluminium hydroxide, and surface-active substances such as lysolecithin, pluronic polyols, polyanions, peptides, oil emulsions, keyhole limpet hemocyanin, and dinitrophenol.

In certain embodiments, the antibody is a polyclonal antibody. Methods for producing and isolating polyclonal antibodies are known. In general, polyclonal antibodies are produced from B-lymphocytes. Typically polyclonal antibodies are obtained directly from an immunized subject, such as an immunized animal. Methods of immunization are known in the art.

In certain embodiments, the antibody is a monoclonal antibody. Monoclonal antibodies may be prepared using a technique that provides for the production of antibody molecules by continuous isolated cells in culture. These include, but are not limited to, the hybridoma technique, the human B-cell hybridoma technique, and the EBV-hybridoma technique. Methods for the preparation of monoclonal antibodies include for example Kohler et al. (1975) Nature 256:495-497 (herein incorporated by reference); Kozbor et al. (1985) J. Immunol. Methods 81:31-42 (herein incorporated by reference); Cote et al. (1983) Proc. Natl. Acad. Sci 80:2026-2030 (herein incorporated by reference); and Cole et al. (1984) Mol. Cell Biol. 62: 109-120 (herein incorporated by reference).

In certain embodiments, the antibody and/or an antigen binding fragment thereof comprises an isolated antibody. In certain embodiments, the antibody and/or an antigen binding fragment thereof comprise a purified antibody. Methods for producing and isolating polyclonal and monoclonal antibodies are known.

The term "isolated" refers to a species, such as a nucleic acid, a polypeptide or an antibody, that has been separated from its natural environment. Certain embodiments of the present disclosure provide an isolated nucleic acid, polypeptide, protein or antibody as described herein.

An isolated nucleic acid, polypeptide or antibody may be partially or substantially purified. In some cases, the isolated entity is in a substantially un-purified state, being associated with a variety of other species. In some cases, the isolated entity is in a substantially purified state, being substantially free of other substances with which it is associated in nature or in vivo. The term "purified" refers to a species that has undergone some form of process to increase the proportion of a desired species. Certain embodiments of the present disclosure provide a purified nucleic acid, polypeptide, protein or antibody as described herein.

In certain embodiments, the antibody has an isotype selected from the group consisting of IgG1, IgG2a, IgG2b, IgG3, IgM and IgA.

In certain embodiments, the antibody and/or an antigen binding fragment thereof is a mouse antibody and/or an antigen binding fragment thereof, a human antibody and/or an antigen binding fragment thereof, or a humanized antibody and/or an antigen binding fragment thereof. Other types of antibodies (or antigen binding fragments thereof) are contemplated Humanized antibodies, or antibodies adapted for non-rejection by other mammals, may be produced by a suitable method known in the art, including for example resurfacing or CDR grafting. In resurfacing technology, molecular modeling, statistical analysis and mutagenesis are combined to adjust the non-CDR surfaces of variable regions to resemble the surfaces of known antibodies of the target host. Strategies and methods for the resurfacing of antibodies, and other methods for reducing immunogenicity of antibodies within a different host are known, for example as described in U.S. Pat. No. 5,639,641. Humanized forms of the antibodies may also be made by CDR grafting, by substituting the complementarity determining regions of, for example, a mouse antibody, into a human framework domain.

Methods for humanizing antibodies are known. For example, the antibody may be generated as described in U.S. Pat. No. 6,180,370 (herein incorporated by reference); WO 92/22653 (herein incorporated by reference); Wright et al. (1992) Critical Rev. in Immunol. 12(3,4): 125-168 (herein incorporated by reference); and Gu et al. (1997) Thrombosis and Hematocyst 77(4):755-759) (herein incorporated by reference).

Humanized antibodies typically have constant regions and variable regions other than the complementarity determining regions (CDRs) derived substantially or exclusively from a human antibody and CDRs derived substantially or exclusively from the non-human antibody of interest.

Techniques developed for the production of "chimeric antibodies", for example the splicing of mouse antibody genes to human antibody genes to obtain a molecule with appropriate antigen specificity and biological activity, may be performed by a suitable method. For example, chimeric antibodies may be produced as described in Morrison, S. L. et al. (1984) Proc. Natl. Acad. Sci 81:6851-6855 (herein incorporated by reference); Neuberger, M. S. et al. (1984) Nature 312:604-608 (herein incorporated by reference); and Takeda, S. et al. (1985) Nature 314:452-454 (herein incorporated by reference).

Immunoassays may be used for screening to identify antibodies and/or antigen binding fragments thereof having the desired specificity.

Antibody molecules and antigen binding fragments thereof may also be produced recombinantly by methods known in the art, for example by expression in *E. coli* expression systems. For example, a method for the production of recombinant antibodies is as described in U.S. Pat. No. 4,816,567 (herein incorporated by reference). Antigen binding fragments may also be produced, for example, by phage display technologies or using peptide libraries, which are known in the art.

Certain embodiments of the present disclosure provide an isolated or purified antibody, or an antigen binding fragment thereof, raised to a polypeptide as described herein.

Certain embodiments of the present disclosure provide an isolated or purified antibody, or an antigen binding fragment thereof, raised to a polypeptide comprising an amino acid sequence of one or more of ASNDHDAAINRYSRLSKKRENDKVKYEVTEDVYT (SED ID NO. 1), DEVASDPLYVPDPDPTKFPVNRNLTRKAGYLNARNKT (SEQ ID NO. 2), and SEGQFVVLSS SQSEESDLGE GGKKRESEA (SEQ ID NO. 3), an antigenic fragment of any of the aforementioned amino acid sequences, and/or a variant of any of the aforementioned amino acid sequences or an antigenic fragment thereof. Certain embodiments of the present disclosure provide an isolated or purified antibody, or an antigen binding fragment thereof, raised to a polypeptide consisting of one or more of the aforementioned amino acid sequences.

In certain embodiments, the antibody, or antigen binding fragment thereof, is raised to one or more polypeptides consisting of an amino acid sequence of ASNDHDAAINRYSRLSKKRENDKVKYEVTEDVYT (SED ID NO. 1), DEVASDPLYVPDPDPTKFPVNRNLTRK-AGYLNARNKT (SEQ ID NO. 2), and SEGQFVVLSS SQSEESDLGE GGKKRESEA (SEQ ID NO. 3), NRYSRLSKKRENDKV (SEQ ID NO. 7), DPDPTKFPVNRNLTR (SEQ ID NO. 8), and SQSEESDLGEGGKKR (SEQ ID NO. 9), an antigenic fragment of any of the aforementioned amino acid sequences, and/or a variant of any of the aforementioned amino acid sequences or antigenic fragment thereof.

Certain embodiments of the present disclosure also provide polypeptides or proteins as described herein.

Certain embodiments of the present disclosure provide a polypeptide consisting of one or more of the following amino acid sequences: ASNDHDAAINRYSRLSKKRENDKVKYEVTEDVYT (SED ID NO. 1), DEVASDPLYVPDPDPTKFPVNRNLTRKAGYLNARNKT (SEQ ID NO. 2), SEGQFVVLSS SQSEESDLGE GGKKRESEA (SEQ ID NO. 3), and NRYSRLSKKRENDKV (SEQ ID NO. 7), DPDPTKFPVNRNLTR (SEQ ID NO. 8), SQSEESDLGEGGKKR (SEQ ID NO. 9), a fragment of any of the aforementioned amino sequences, an antigenic fragment of any of the aforementioned amino acid sequences, and/or a variant of any of the aforementioned amino acid sequences or an antigenic fragment thereof. In certain embodiments, the polypeptide is an isolated polypeptide. Such polypeptides may, for example, be used to raise an antibody.

Certain embodiments of the present disclosure provide a non-naturally occurring polypeptide comprising one or more of the following amino acid sequences: ASNDHDAAINRYSRLSKKRENDKVKYEVTEDVYT (SED ID NO. 1), DEVASDPLYVPDPDPTKFPVNRNLTRK-AGYLNARNKT (SEQ ID NO. 2), SEGQFVVLSS SQSEESDLGE GGKKRESEA (SEQ ID NO. 3), and NRYSRLSKKRENDKV (SEQ ID NO. 7), DPDPTKFPVNRNLTR (SEQ ID NO. 8), SQSEESDLGEGGKKR (SEQ ID NO. 9), a fragment of any of the aforementioned amino sequences, an antigenic fragment of any of the aforementioned amino acid sequences, and/or a variant of any of the aforementioned amino acid sequences or an antigenic fragment thereof. In certain embodiments, the polypeptide is an isolated polypeptide. Such polypeptides may, for example, be used to raise an antibody.

Certain embodiments of the present disclosure provide an isolated and/or purified antibody binding to an epitope in an amino acid sequence in the human APPL1 protein comprising one or more of ASNDHDAAINRYSRLSKKRENDKVKYEVTEDVYT (SED ID NO.1), DEVASDPLYVPDPDPTKFPVNRNLTRKAGYLNARNKT (SEQ ID NO. 2), SEGQFVVLSS SQSEESDLGE GGKKRESEA (SEQ ID NO. 3), and/or an equivalent region of a homolog, ortholog or paralog of the protein. Methods for identifying the equivalent binding regions of related targets are known in the art.

In certain embodiments, the epitope comprises one or more of the amino acid sequences NRYSRLSKKRENDKV (SEQ ID NO. 7), DPDPTKFPVNRNLTR (SEQ ID NO. 8), and QSEESDLGEGGKKR (SEQ ID NO. 9), and/or an equivalent region of a homolog, ortholog or paralog of the APPL1 protein.

In certain embodiments, a polypeptide (or protein) as described herein is an isolated polypeptide. In certain embodiments, the polypeptide (or protein) as described herein is a purified polypeptide. In certain embodiments, a polypeptide (or protein) as described herein is a non-naturally occurring polypeptide. In certain embodiments, a polypeptide (or protein) as described herein is a recombinant polypeptide. In certain embodiments, a polypeptide (or protein) as described herein is a synthetic polypeptide. Other types of polypeptides are contemplated.

The term "variant" of a polypeptide or of an amino acid sequence includes, for example, one or more of amino acid insertion variants, amino acid deletion variants, amino acid substitution variants, and amino acid modification variants (natural and/or synthetic).

For example, amino acid insertion variants may comprise amino- and/or carboxy-terminal fusions (of any desired length) and also insertions of single or two or more amino acids in a particular amino acid sequence. In the case of amino acid sequence variants having an insertion, one or more amino acid residues may be inserted into a particular site in an amino acid sequence, although random insertion with appropriate screening of the resulting product is also possible.

Amino acid deletion variants are characterized by the removal of one or more amino acids from the sequence. Amino acid substitution variants are characterized by at least one residue in the sequence being removed and another residue being inserted in its place.

Amino acid changes in variants may be non-conservative and/or conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

The polypeptides and amino acid variants described herein may be readily prepared with the aid of known peptide synthesis techniques such as, for example, by solid phase synthesis and similar methods or by recombinant DNA manipulation. The manipulation of DNA sequences for preparing proteins and peptides having substitutions, insertions or deletions, is described in detail in Sambrook, J, Fritsch, E. F. and Maniatis, T. Molecular Cloning: A Laboratory Manual 2nd. ed. Cold Spring Harbor Laboratory Press, New York. (1989), herein incorporated by reference, and Ausubel et al., Current Protocols in Molecular Biology (2011), John Wiley & Sons, Inc., herein incorporated by reference.

The term "derivatives" refers to a modified form of a species. For example, a derivative of a polypeptide or protein refers to a modified form of a polypeptide or protein. Such modifications include chemical modifications and comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides.

Methods for isolating and/or producing polypeptides and protein are known, and are as described generally in Sambrook, J, Fritsch, E. F. and Maniatis, T. Molecular Cloning: A Laboratory Manual 2nd. ed. Cold Spring Harbor Laboratory Press, New York. (1989), herein incorporated by reference, and Ausubel et al., Current Protocols in Molecular Biology (2011), John Wiley & Sons, Inc., herein incorporated by reference.

Certain embodiments of the present disclosure provide an isolated and/or purified antibody raised to a polypeptide comprising an amino acid sequence of one or more of PNTFKTLDSWRDEFLIQASPRDPENFPFVVLGNKI (SED ID NO. 4), DPENFPFVVLGNKIDLENRQVATKRAQAWCYSKNN (SEQ ID NO. 5), ALKQETEVELYNEFPEPIKLDKNDRAKASAESCSC (SEQ ID NO. 6), an antigenic fragment of any of the aforementioned amino acid sequences, and/or a variant of any of the aforementioned amino acid sequences or an antigenic fragment thereof. Certain embodiments of the present disclosure provide an isolated or purified antibody, or an antigen binding fragment thereof, raised to a polypeptide consisting of one or more of the aforementioned amino acid sequences.

In certain embodiments the antibody is raised to a polypeptide comprising an amino acid sequence of one or more of RDEFLIQASPRDPEN (SEQ ID NO. 10), GNKIDLENRQVATKR (SEQ ID NO. 11) and YNEFPEPIKLDKNDR (SEQ ID NO. 12), an antigenic fragment of any of the aforementioned amino acid sequences, and/or a variant of any of the aforementioned amino acid sequences or an antigenic fragment thereof. Certain embodiments of the present disclosure provide an isolated or purified antibody, or an antigen binding fragment thereof, raised to a polypeptide consisting of one or more of the aforementioned amino acid sequences.

Certain embodiments of the present disclosure provide a polypeptide consisting of one or more of the following amino acid sequences: PNTFKTLDSWRDEFLIQASPRDPENFPF VVLGNKI (SED ID NO. 4), DPENFPFVVLGNKIDLENRQVATKRAQAWCYSKNN (SEQ ID NO. 5), ALKQETEVELYNEFPEPIKLDKNDRAKA SAESCSC (SEQ ID NO. 6), RDEFLIQASPRDPEN (SEQ ID NO. 10), GNKIDLENRQVATKR (SEQ ID NO. 11) and YNEFPEPIKLDKNDR (SEQ ID NO. 12), a fragment of any of the aforementioned amino sequences, an antigenic fragment of any of the aforementioned amino acid sequences, and/or a variant of any of the aforementioned amino acid sequences or an antigenic fragment thereof. Such polypeptides may, for example, be used to raise an antibody.

Certain embodiments of the present disclosure provide a non-naturally occurring polypeptide comprising one or more of the following amino acid sequences: PNTFKTLDSWRDEFLIQASPRDPENFPF VVLGNKI (SED ID NO. 4), DPENFPFVVLGNKIDLENRQVATKRAQAWCYSKNN (SEQ ID NO. 5), ALKQETEVELYNEFPEPIKLDKNDRAKA SAESCSC (SEQ ID NO. 6), RDEFLIQASPRDPEN (SEQ ID NO. 10), GNKIDLENRQVATKR (SEQ ID NO. 11) and YNEFPEPIKLDKNDR (SEQ ID NO. 12), a fragment of any of the aforementioned amino sequences, an antigenic fragment of any of the aforementioned amino acid sequences, and/or a variant of any of the aforementioned amino acid sequences or an antigenic fragment thereof. Such polypeptides may, for example, be used to raise an antibody.

Certain embodiments of the present disclosure provide an isolated and/or purified antibody binding to an epitope in an amino acid sequence in the human RAB7 protein comprising one or more of PNTFKTLDSWRDEFLIQASPRDPENFPF VVLGNKI (SED ID NO. 4), DPENFPFVVLGNKIDLENRQVATKRAQAWCYSKNN (SEQ ID NO. 5), ALKQETEVELYNEFPEPIKLDKNDRAKASAESCSC (SEQ ID NO. 6), and/or an equivalent region of a homolog, ortholog or paralog of the protein.

In certain embodiments, the epitope comprises one or more of the amino acid sequences RDEFLIQASPRDPEN (SEQ ID NO. 10), GNKIDLENRQVATKR (SEQ ID NO. 11) and YNEFPEPIKLDKNDR (SEQ ID NO. 12) and/or an equivalent region of a homolog, ortholog or paralog of the RAB7 protein.

Certain embodiments of the present disclosure provide an isolated and/or purified antibody raised to a polypeptide comprising an amino acid sequence of CKKLDDFVETGDIRTMVFP (SEQ ID NO. 13), an antigenic fragment of any of the aforementioned amino acid sequences, and/or a variant of any of the aforementioned amino acid sequences or an antigenic fragment thereof. Certain embodiments of the present disclosure provide an isolated or purified antibody, or an antigen binding fragment thereof, raised to a polypeptide consisting of the aforementioned amino acid sequence.

Certain embodiments of the present disclosure provide an isolated and/or purified antibody binding to an epitope in an amino acid sequence in the human LIMP-2 protein comprising CKKLDDFVETGDIRTMVFP (SEQ ID NO. 13) and/or an equivalent region of a homolog, ortholog or paralog of the protein.

Certain embodiments of the present disclosure provide a polypeptide consisting of the following amino acid sequence: CKKLDDFVETGDIRTMVFP (SEQ ID NO. 13), a fragment of the aforementioned amino sequence, an antigenic fragment of the aforementioned amino acid sequence, and/or a variant of the aforementioned amino acid sequence or an antigenic fragment thereof. Such polypeptides may, for example, be used to raise an antibody.

Certain embodiments of the present disclosure provide a non-naturally occurring polypeptide comprising the following amino acid sequence: CKKLDDFVETGDIRTMVFP (SEQ ID NO. 13), a fragment of the aforementioned amino sequence, an antigenic fragment of the aforementioned amino acid sequence, and/or a variant of the aforementioned amino acid sequence or an antigenic fragment thereof. Such polypeptides may, for example, be used to raise an antibody.

Certain embodiments of the present disclosure provide a method of detecting an APPL1 protein or a fragment thereof, the method comprising using an antibody as described herein.

Certain embodiments of the present disclosure provide a method of detecting a RAB7 protein or a fragment thereof, the method comprising using an antibody as described herein.

Certain embodiments of the present disclosure provide a method of detecting a LIMP2 protein or a fragment thereof, the method comprising using an antibody as described herein.

Certain embodiments of the present disclosure provide a method of detecting a prostate cancer in a subject, the method comprising using an antibody as described herein to detect an APPL1, RAB7 or LIMP2 protein, and/or a fragment, derivative or a processed form thereof from the subject.

Certain embodiments of the present disclosure provide a kit comprising an antibody as described herein. The kit may comprise one or more other reagents as described herein.

Certain embodiments of the present disclosure provide a hybridoma producing an antibody as described herein. Methods for producing hybridomas and monoclonal antibodies are known in the art.

A typical protocol for the production of a hybridoma is as follows: Animals (e.g. mice) are first exposed to the selected antigen. Usually this is done by a series of injections of the antigen, over the course of several weeks. Once splenocytes are isolated from the mammal's spleen, the B cells may be fused with immortalised myeloma cells. The myeloma cells are generally selected to ensure they are not secreting antibody themselves and that they lack the hypoxanthine-guanine phosphoribosyltransferase (HGPRT) gene, making them sensitive to HAT medium. The fusion may be accomplished, for example, using polyethylene glycol or Sendai virus.

Fused cells are incubated in HAT medium for roughly 10 to 14 days. Aminopterin blocks the pathway that allows for nucleotide synthesis and unfused myeloma cells die, as they cannot produce nucleotides by the de novo or salvage pathways, because they lack HGPRT. Removal of the unfused myeloma cells is necessary because they have the potential to outgrow other cells, especially weakly established hybridomas. Unfused B cells die as they have a short life span. In this way, only the B cell-myeloma hybrids survive, since the HGPRT gene coming from the B cells is functional. These cells produce antibodies and are immortal. The incubated medium is then diluted into multi-well plates to such an extent that each well contains only one cell. Since the antibodies in a well are produced by the same B cell, they will be directed towards the same epitope, and are thus monoclonal antibodies.

The next stage is a rapid primary screening process, which identifies and selects only those hybridomas that produce antibodies of appropriate specificity. The hybridoma culture supernatant, secondary enzyme labeled conjugate, and chromogenic or fluorescent substrate, are then incubated, and the formation of a colored product indicates a positive hybridoma. Alternatively, immunocytochemical screening or flow cytometry can also be used.

The B cell that produces the desired antibodies can be cloned to produce many identical daughter clones. Supplemental media containing interleukin-6 are essential for this step. Once a hybridoma colony is established, it will continually grow in culture medium like RPMI-1640 (with antibiotics and fetal bovine serum) and produce antibodies.

Multiwell plates are used initially to grow the hybridomas, and after selection, are changed to larger tissue culture flasks. This maintains the well-being of the hybridomas and provides enough cells for cryopreservation and supernatant for subsequent investigations. The culture supernatant can yield 1 to 60 μg/ml of monoclonal antibody, which is maintained at −20° C. or lower until required.

By using culture supernatant or a purified immunoglobulin preparation, further analysis of a potential monoclonal antibody producing hybridomas can be made in terms of reactivity, specificity, and cross-reactivity.

Finally, standard techniques may be used for recombinant DNA technology, oligonucleotide synthesis, antibody production, peptide synthesis, tissue culture and transfection. Enzymatic reactions and purification techniques may be performed according to manufacturer's specifications or as commonly accomplished in the art or as described herein. The foregoing techniques and procedures may be generally performed according to conventional methods known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), herein incorporated by reference.

Exemplary embodiments are illustrated by the following examples. It is to be understood that the following description is for the purpose of describing particular embodiments only and is not intended to be limiting with respect to the above description.

Example 1—Altered Endosome Biogenesis in Prostate Cancer

Materials and Methods (i) Reagents

A LIMP-2 sheep polyclonal antibody was generated using the peptide sequence CKKLDDFVETGDIRTMVFP (SEQ ID NO. 13) (Mimotopes Pty Ltd., Victoria, Australia). Primary antibodies used in this study included rabbit polyclonal antibodies against APPL1 (0.4 μg/mL, Abcam PLC, Cambridge United Kingdom, cat #ab95195), APPL2 (0.4 μg/m, Abcam, cat #ab95196), Rab4 (1 μg/mL, Abcam, cat #ab13252), TGN46 (10 μg/mL, Abcam, cat #ab50595), TfR1 (1 μg/mL, Abcam, cat #ab108985), TfR2 (1 μg/mL, Abcam, cat #ab80194), Akt (1/1000, Cell Signaling Technology, Inc., MA, USA) and Phospho-Akt (Thr308 1/1000, Cell Signaling Technology, Inc.). Goat anti-Rab5 (1 μg/mL, Santa Cruz Biotechnology, CA, USA), Rab7 (1 μg/mL, Santa Cruz Biotechnology) and EEA1 (1 μg/mL, Santa Cruz Biotechnology) polyclonal antibodies were also used. LAMP-1 (1 μg/mL) mouse monoclonal BB6 was provided by Umea University, Sweden). HRP conjugated secondary antibodies for Western blot analysis included anti-goat/sheep (1/2000, Merck Millipore Pty. Ltd., Victoria, Australia), anti-rabbit (1/2000, Sigma Aldrich Pty. Ltd., New South Wales, Australia) and anti-mouse (1/2000 Sigma Aldrich Pty. Ltd.). HRP-conjugated anti-GAPDH (1/20000 Sigma Aldrich Pty. Ltd.). The secondary and other antibody conjugated fluorophores that were used included Alexa Fluor® 488 (1/250), Alexa Fluor® 633 (1/250), Transferrin-633 (1/1000), Phalloidin-488 (1/100), LysoTracker® (5 μM), from Life Technologies Pty Ltd., Victoria, Australia. Primers were obtained from Geneworks Pty Ltd., Adelaide, Australia and the sequences listed in Supporting Information Table 1.

(ii) Cell Lines and Culture Conditions

The cell lines PNT1a and PNT2, 22RV1 and LNCaP (clone FCG) were obtained from the European Collection of Cell Cultures via CellBank Australia (Children's Medical Research Institute, New South Wales, Australia). These cell lines were absent from the list of cross-contaminated or misidentified cell lines, version 6.8 (9 Mar. 2012). PNT1a and PNT2 were previously derived from Simian vacuolating virus 40 (SV40) immortalised cell lines. The 22RV1 cancer cell line was previously derived from a xenograft, which had been serially propagated in mice after castration-induced regression and relapse of a parental, androgen-dependent xenograft. This cell line expressed the androgen receptor, but its proliferation was unresponsive to androgen stimulation. LNCaP was previously derived from a lymph node metastasis of prostate adenocarcinoma and is androgen responsive.

Cell lines were cultured in T75 tissue culture flasks and maintained in Roswell Park Memorial Institute (RPMI) 1640 culture medium (Gibco®, Life Technologies Australia Pty Ltd., Victoria, Australia), supplemented with 10% foetal calf serum (In Vitro Technologies Pty Ltd., Victoria, Australia) and 2 mM L-glutamine (Sigma Aldrich Pty Ltd., New South Wales, Australia). Cells were incubated at 37° C. with 5% $CO_2$ in a Sanyo MCO-17AI humidified incubator (Sanyo Electric Biomedical Co., Ltd., Osaka, Japan). Cells at approximately 90% confluence were passaged by washing with sterile PBS (Sigma Aldrich), trypsin treated (Trypsin-EDTA solution containing 0.12% trypsin, 0.02% EDTA; SAFC®, Sigma Aldrich, New South Wales, Australia), for dissociation from the culture surface and then suspended in supplemented culture medium.

(iii) Cell Extract Preparation

The culture medium was aspirated from 80-90% confluent cell cultures, the cells washed once with PBS, and then incubated with 800 μL of a 20 mM Tris (pH 7.0), 500 mM sodium chloride and 2% SDS solution. Cells were harvested and an extract prepared by heating to 65° C. and sonication for one minute. The lysate was then passaged 6 times through a 25-gauge needle. Total protein in cell extracts was quantified using a bicinchoninic acid assay according to the manufacturer's instructions (Micro BCA kit, Pierce, Rockford, IL, USA). Samples were quantified using a Wallac Victor™ optical plate-reader and Workout software v2.0 (Perkin-Elmer Pty, Ltd., Victoria, Australia), using a 5-point parameter standard curve. Cell extracts were stored at −20° C.

(iv) Gene Expression Analysis

Cell lines were cultured to 80-90% confluence (triplicate T75 flasks), the culture medium aspirated and the cell layer washed with PBS, before the addition of 1 mL TRI Reagent® (Applied Biosystems Pty Ltd., Victoria, Australia) for harvesting. Two hundred microlitres of chloroform was added per millilitre of TRI Reagent® and samples shaken vigorously for one minute, incubated at room temperature for three minutes and then centrifuged for 15 minutes at 16,000 g at 4° C. RNA extraction was performed using an RNeasy® mini kit (Qiagen Pty Ltd., Victoria, Australia) according to the manufacturer's instructions. The concentration of extracted RNA was determined using a NanoDrop™ 2000 spectrophotometer (Thermo Fisher Scientific Australia Pty Ltd., Victoria, Australia) at 260 nm. Ratios of 260/280 nm and 260/230 nm were assessed to ensure samples were free from protein and DNA contamination; a ratio greater than 1.6 indicated a sample free of contamination.

Complementary DNA (cDNA) for qRT-PCR was prepared using a High Capacity RNA-to-cDNA Kit (Life Technologies Pty Ltd., Victoria, Australia). Primer sequences were obtained from either published literature, Harvard PrimerBank or designed using NCBI Primer-BLAST. Primers were either selected or designed based on the criteria of the final amplicon-size being less than 150 base-pairs, a melting temperature near 60° C. and where possible, extension across an exon-exon junction. For quantitative RT-PCR 10 μL of reaction mixture contained 5 Power SYBR® Green PCR Master Mix (Life Technologies Australia Pty Ltd., Victoria, Australia), 0.5 μL each of 10 nM forward and reverse primer, 2 μL cDNA sample diluted to 1:25 with DEPC-treated $H_2O$, and 2 μL DEPC-treated $H_2O$. Reactions were plated in triplicate onto 96-well plates (Life Technologies Australia Pty Ltd., Victoria, Australia), with each plate containing serial dilutions of a reference cDNA sample for the target-gene and endogenous-gene standard curves, to control for reaction efficiency. qPCR was performed using a 7500 Fast Real-Time PCR System (Life Technologies Australia Pty Ltd., Victoria, Australia) using ABI 7500 software v2.0.2.

Cycling conditions for all targets comprised; 50° C. for 2 minutes, 95° C. for 10 minutes to activate the enzyme and denature cDNA followed by 40 cycles of a 95° C. 15-second denaturation step and a 60° C. 60-second extension and signal-acquisition step. Cycle threshold ($C_T$) values were derived at a threshold level of 0.35 in the exponential phase of amplification and above baseline noise. The relative amount of gene expression from each sample was derived by calculation of $C_T$ values versus standard curves produced from serial-dilutions. Reaction efficiencies, calculated from the slope of a linear trend-line plotted from diluted standards, were between 90 and 110%. Mean gene expression was derived from the mRNA amount on each replicate plate, with each single plate providing a mean $C_T$ and mRNA level from replicate wells.

(v) Western Blotting

Ten μg of cell lysate was heat-denatured (5 min at 100° C. in NuPAGE® LDS Sample Buffer and reducing agent) then electrophoresed at 120V for 1.5 hours using pre-cast gels in an XCell SureLock Mini-Cell system (Life Technologies Australia Pty Ltd., Victoria, Australia). Protein was then transferred to polyvinylidene difluoride membranes (Polyscreen®, PerkinElmer, Victoria, Australia) at 35 V for one hour. The transfer membranes were blocked for 1 hour at RT using 5% (w/v) skim milk solution in TBS-tween (0.1%; block) and incubated with primary antibody overnight at 4° C. The membranes were washed 3×5 min in TBS-tween (0.1%) and then incubated with the appropriate horseradish-peroxidase conjugated secondary antibody diluted 1/2000 in block solution. The membranes were developed using aNovex® ECL chemiluminescent substrate reagent kit (Life Technologies Australia Pty Ltd., Victoria, Australia) and proteins visualised using an ImageQuant™ LAS 4000 imager, software version 1.2.0.101 (GE Healthcare Bio-Sciences Pty Ltd., New South Wales, Australia). Triplicate samples were analysed and images quantified relative to a reference GAPDH loading control using AlphaViewSA™ software v3.0.0.0 (ProteinSimple, Santa Clara, California). Kruskal-Wallis rank sum statistical analyses using Stata/SE v11.2 (StataCorp LP, Texas, U.S.A) was performed to determine significance between non-malignant control and cancer cell line groups (95% confidence limit; $p<0.05$).

(vi) Confocal Microscopy

Cells were cultured on 22 mm glass coverslips, fixed with 4% (v/v) formaldehyde in PBS for 20 minutes at room temperature, then permeabilised with 0.1% Triton-X (v/v) in PBS for 10 minutes. Non-specific antibody reactivity was blocked by incubation with 5% (w/v) bovine serum albumin in PBS for two hours at RT. Cells were then incubated with primary antibody in 5% BSA for two hours at room temperature, then secondary antibody for one hour at RT. Unbound antibody was removed by three PBS washes and coverslips mounted in ProLong® Gold Antifade Reagent containing DAPI nuclear stain (Life Technologies Australia Pty Ltd., Victoria, Australia). Confocal microscopy was performed using a Zeiss LSM 710 META NLO laser scanning microscope and associated Carl Zeiss Zen 2009 software. Laser lines of 370, 488, 543 and 633 nm were utilised for DAPI, Alexa Fluor® 488, Cy3 and Alexa Fluor® 633 fluorescence, respectively. Images were exported as greyscale 16-bit TIFF files and processed using Adobe® Photoshop® CS5 (Adobe Systems Inc., San Jose, California, U.S.A).

(vii) Immunohistochemistry

Matched human non-malignant and tumour prostate tissue sections (3 µm) were mounted on Superfrost Ultra Plus® slides (Menzel-Glaser) and heated overnight at 50° C. Sections were then dewaxed in xylene, rehydrated in ethanol and incubated in 0.3% $H_2O_2$ in PBS for 15 min at RT. HIER was carried out using 10 mM citrate buffer (pH 6.5) in a Decloaking Chamber (Biocare Medical) for 5 min at 125° C. Slides were blocked first using an Invitrogen Avidin/Biotin Kit (as per manufacturer's instructions) and then in 5% blocking serum (SIGMA) for 30 min at RT in a humid chamber. Sections were then incubated with primary antibody overnight at 4° C. in a humid chamber, followed by incubation with the appropriate biotinylated secondary antibody (1/400; DAKO) for 1 hour at RT in a humid chamber, then streptavidin-horseradish peroxidise (1/500; DAKO) at RT for 1 hour in a humid chamber and finally with DAB/$H_2O_2$. The tissue sections were then counterstained with Lillie-Mayer's haemotoxylin, rinsed in water, rehydrated and mounted on slides with DPX. Images were obtained by scanning slides using a Nanozoomer (Hamamatsu)

Figure 2:
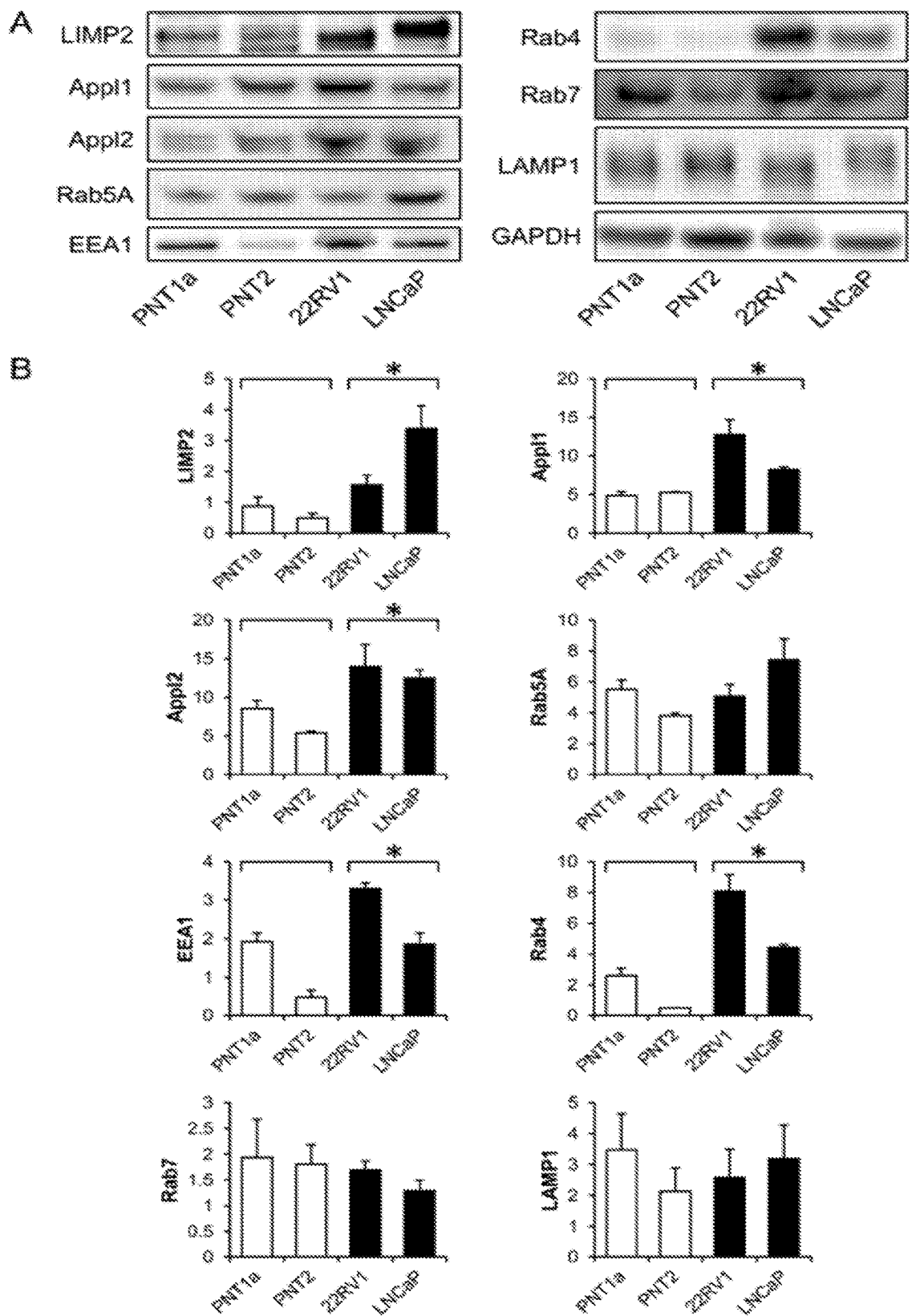
FIG. 2 shows detection and quantification of intracellular lysosomal proteins in non-malignant control and prostate cancer cell lines. (A) Representative images from Western blot analysis of 10 μg whole cell lysate from non-malignant control cell lines PNT1a and PNT2, and cancer cell lines 22RV1 and LNCaP, examined in triplicate. (B) Protein amount was quantified by densitometry relative to GAPDH endogenous control. Data was analysed by Kruskal-Wallis rank sum method with statistical significance (p<0.05) represented by an asterisk.

Results (i) Increased Endosome Related Gene and Protein Expression in Prostate Cancer Cells The expression of endosome and lysosome related genes was quantified by qRT-PCR in control and prostate cancer cells and normalised to the expression of GAPDH mRNA. The amounts of APPL1, APPL2, EEA1, RAB5A, RAB4A and LIMP2 mRNA were significantly increased in prostate cancer when compared to non-malignant control cell lines ($p<0.05$; FIG. 1). In each case there was an approximately 2-3 fold increase in mRNA expression. There was not a significant difference in the amount of either RAB7A or LAMP1 mRNA detected in prostate cancer cells compared to non-malignant controls. Western analysis demonstrated significant increases in the amount of APPL1, APPL2, EEA1, Rab4 and LIMP-2 protein in extracts from prostate cancer cells when compared to non-malignant control cells ($p<0.05$; FIG. 2). Moreover, for both LIMP-2 and Rab4 the increase was approximately 2-4 fold for prostate cancer when compared to non-malignant control cells (FIG. 2). There was not a significant difference in the amount of Rab5A, Rab7 and LAMP-1 protein detected in non-malignant compared to prostate cancer cells (FIG. 2).

(ii) Altered Distribution of Endosomes and Lysosomes in Prostate Cancer Cells

Figure 3:
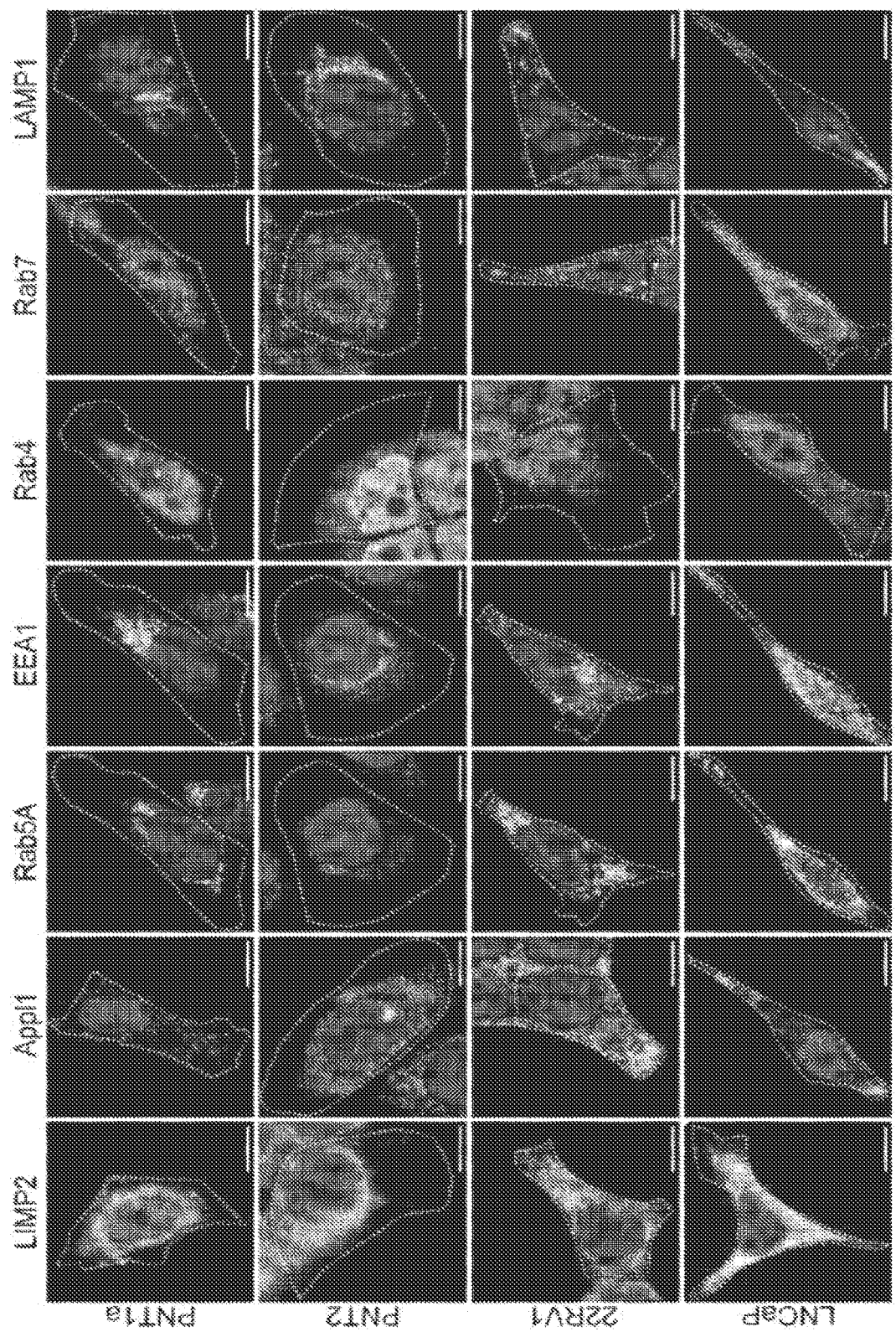
FIG. 3 shows confocal micrographs showing altered localisation of endosomal markers in prostate cancer cell lines compared to non-malignant control cell lines. Fixed cells were probed for endosome markers (green) and counterstained with DAPI nuclear stain (blue) and visualised by laser-scanning confocal microscopy. Transmitted light illumination was captured for visualisation of cell outline (white). Scale bars for all images represent 10 μm.
Figure 4:
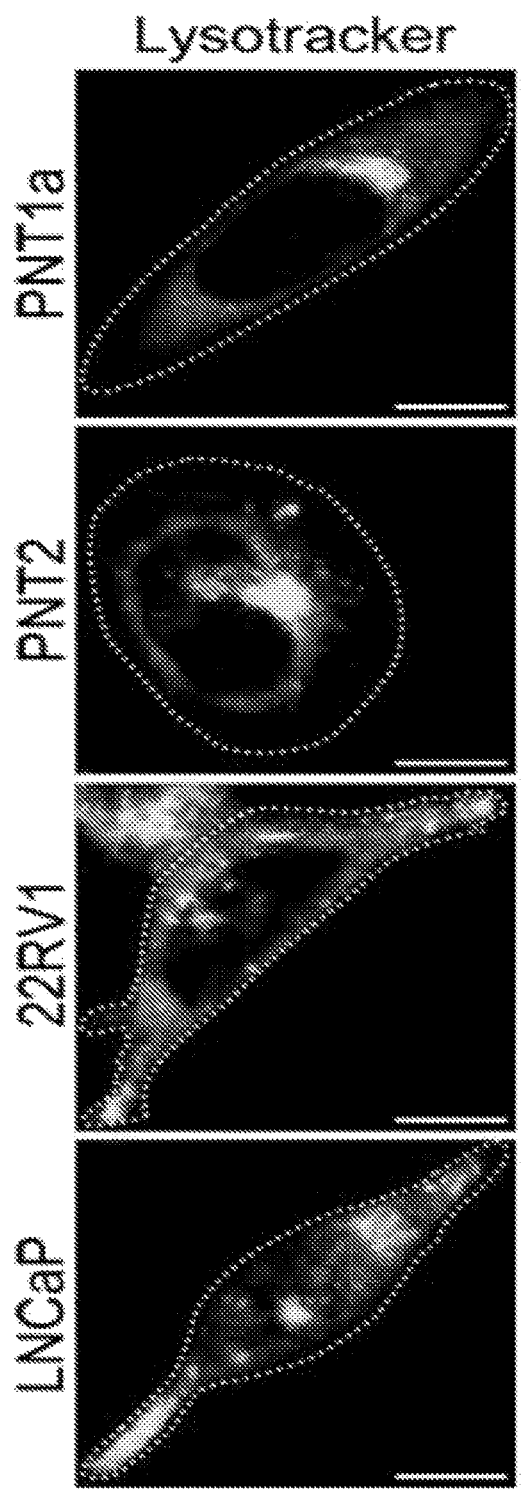
FIG. 4 shows confocal micrographs of Lysotracker®-positive vesicles in prostate cell lines. Non-malignant control prostate cell lines PNT1a and PNT2, and prostate cancer cell lines 22RV1 and LNCaP were stained with Lysotracker® (green). Cell outlines were visualised by TPMT and membrane depicted by white botted line. Scale bars for all images represent 10 μm.

Representative confocal images for the distribution of endosomes and lysosomes (FIG. 3), show increased staining and altered compartment distribution in prostate cancer compared to the non-malignant controls. APPL1 positive endosomes were detected mainly in the perinuclear region of non-malignant control cells, whereas in prostate cancer cells these compartments were distributed towards the cell periphery and tended to be more concentrated near the plasma membrane in cellular extensions/pseudopodia. Rab5A displayed a similar distribution to its effector EEA1 in both non-malignant control and prostate cancer cells. However, in non-malignant control cells both Rab5A and EEA1 were concentrated in the perinuclear region, while in prostate cancer cells these endosomal compartments were found throughout the cytoplasm, with some compartments located towards the cell periphery in cellular extensions. Rab7 positive endosomes were located mainly in the perinuclear region of both non-malignant control and prostate cancer cells. In non-malignant control cells LIMP-2 was concentrated in the perinuclear region, with some tubular and punctuate vesicular staining in the remainder of the cytoplasm and near the cell surface. In contrast, prostate cancer cells displayed relatively smaller LIMP-2 compartments, which had an even distribution throughout the cytoplasm. In non-malignant control cells, LAMP-1 was detected on compartments that were concentrated in the perinuclear region, whereas in prostate cancer cells the LAMP-1 compartments were distributed away from the perinuclear region, concentrated in cellular extensions. Consistent with the LAMP-1 staining, LysoTracker™ positive acidic compartments were concentrated mainly in the perinuclear region of non-malignant control cells, whereas in prostate cancer cells, these compartments were detected in both the perinuclear region and in cytoplasmic extensions (FIG. 4).

(iii) Altered Distribution of Endocytosed Transferrin in Prostate Cancer Cells

Figure 5:
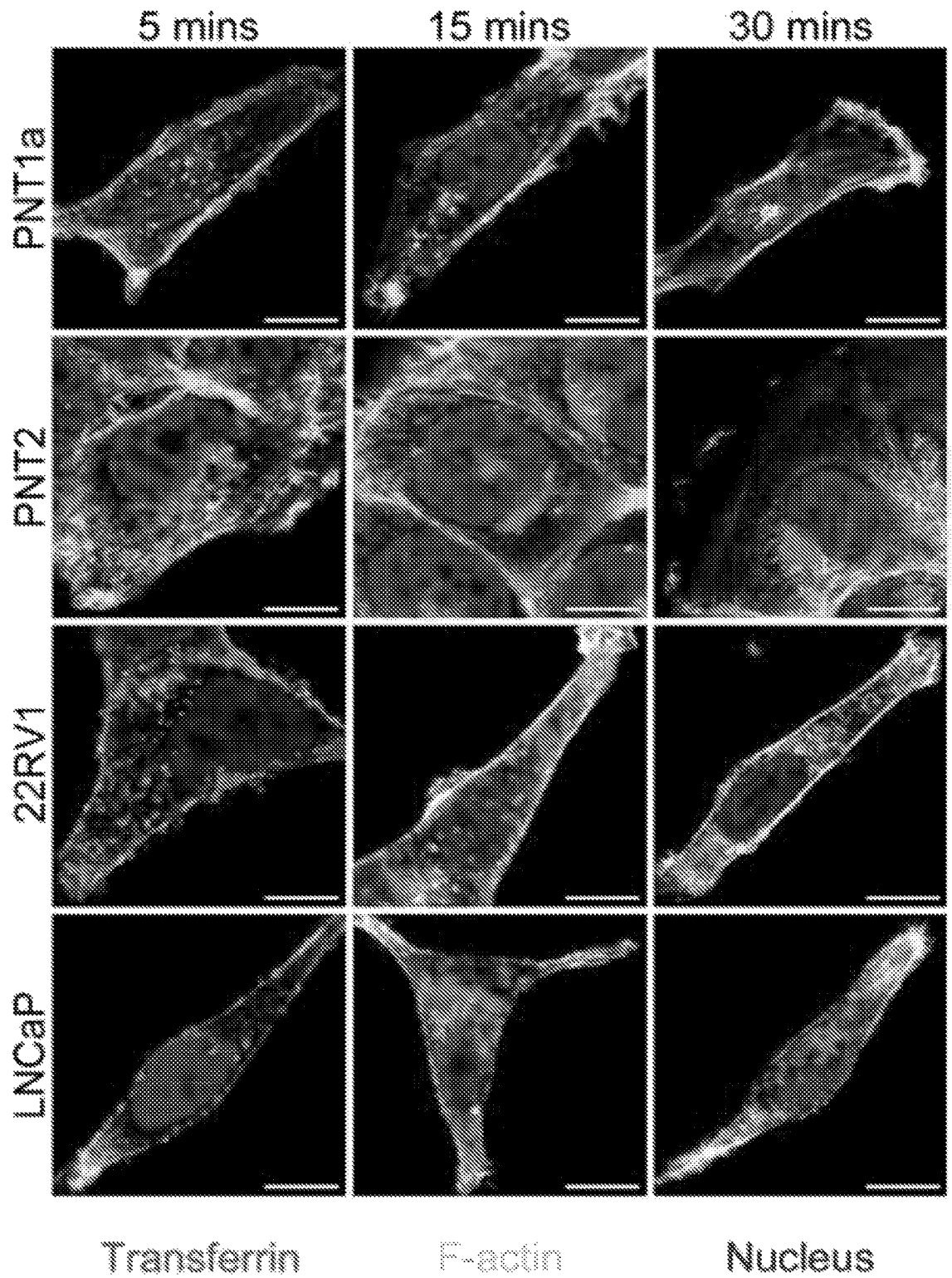
FIG. 5 shows time-course of transferrin uptake in prostate cell lines. Confocal micrographs showing increased uptake and altered distribution of transferrin in prostate cancer cell lines compared to non-malignant control cell lines; together with altered actin staining. Cell cultures were incubated with transferrin Alexa Fluor® 633 conjugate (red) for a period of 5, 15 and 30 minutes prior to cell fixation and actin labelled with phalloidin Alexa Fluor® 488 (green). Scale bars represent 10 μm.
Figure 6:
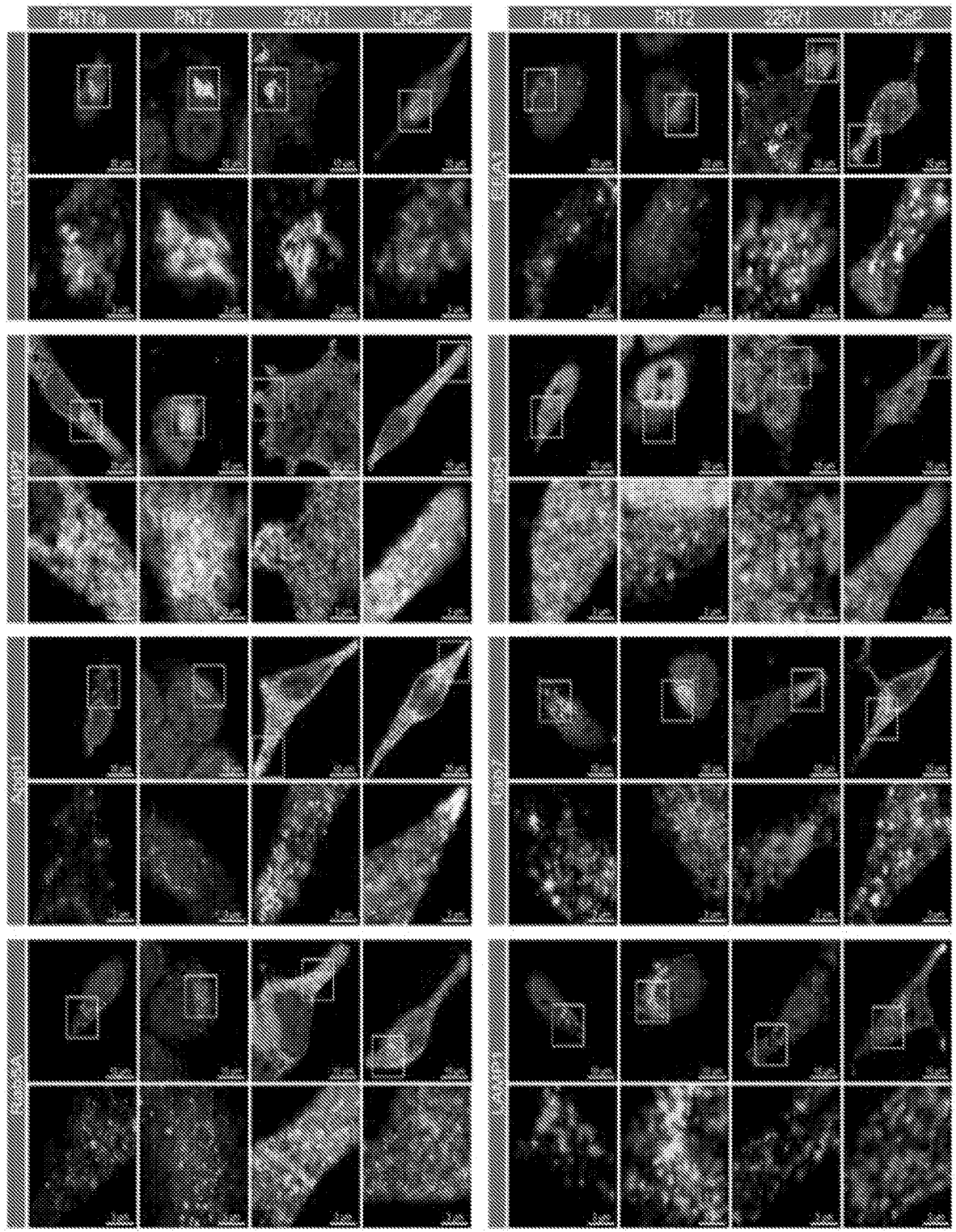
FIG. 6 shows transferrin and endosome/lysosome marker co-fluorescence. Confocal micrographs showing transferrin (red) and endosome/lysosome marker (green) in non-malignant control cell lines PNT1a and PNT2, and prostate cancer cell lines 22RV1 and LNCaP. Colocalisation is represented by yellow fluorescence.
Figure 7:
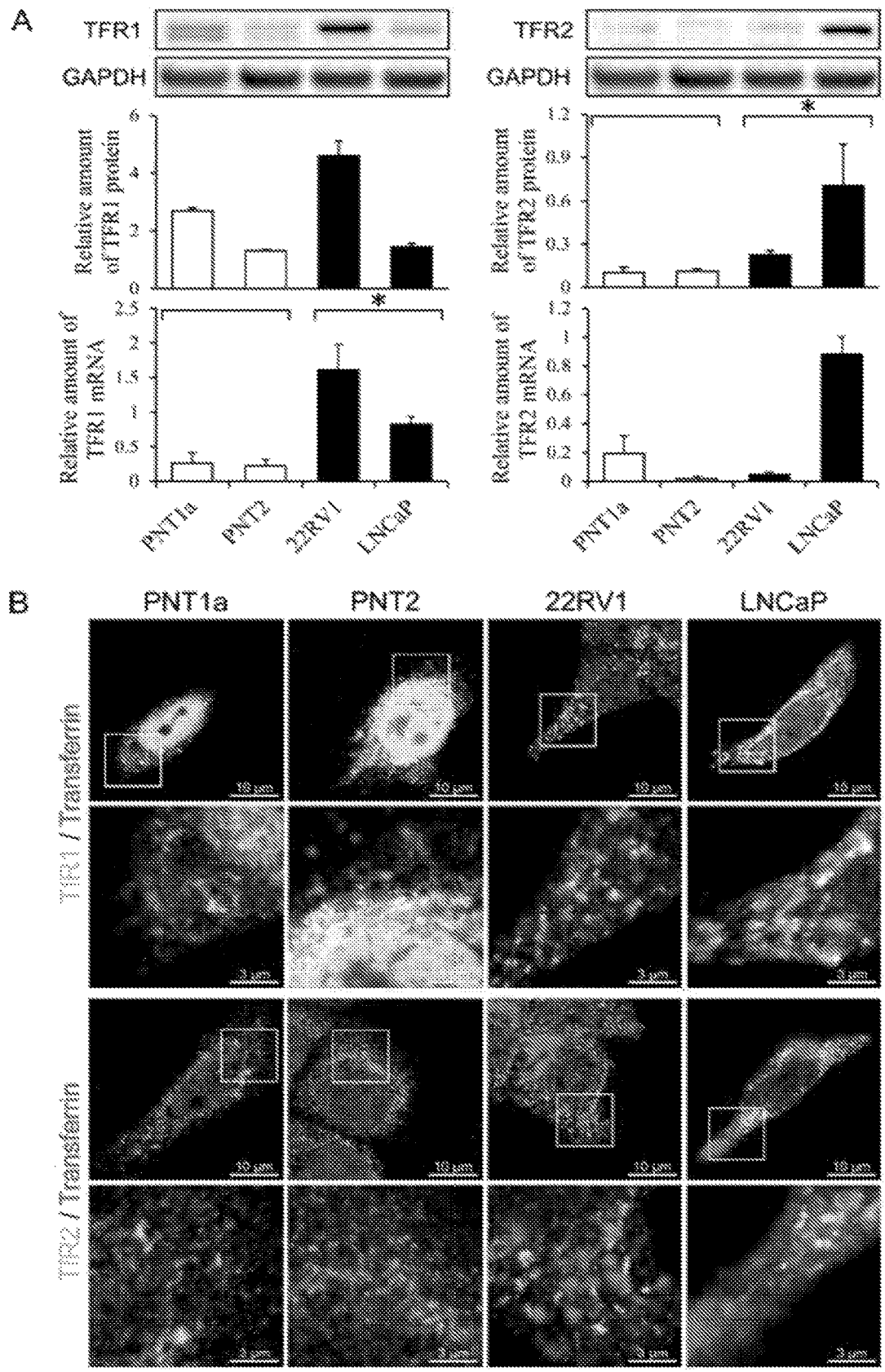
FIG. 7 shows analysis of transferrin receptor expression and cell localisation with transferrin. (A) Western blot analysis and quantification of protein amount and gene expression of transferrin receptor 1 (TFR1) and transferrin receptor 2 (TFR2). Quantification of protein and gene expression was relative to GAPDH protein and gene, respectively. Asterisk represents p<0.05. (B) Confocal micrographs and enlargements showing transferrin (red) and transferrin receptor (green) in non-malignant control cell lines PNT1a and PNT2, and prostate cancer cell lines 22RV1 and LNCaP. Colocalisation of transferrin receptor and transferrin is represented by yellow fluorescence.

Previous studies have reported increased uptake of transferrin in prostate cancer cells, prompting the investigation of receptor expression and transferrin endocytosis in relation to the observed increase in endosome protein expression and altered endosome distribution. In non-malignant control cells, endocytosed transferrin was observed in punctuate intracellular structures after 5 minutes and in the perinuclear region at 15 and 30 minutes (FIG. 5). The prostate cancer cells endocytosed more transferrin than the non-malignant control cell lines and the internalised transferrin was not as concentrated in the perinuclear region of prostate cancer cells, with more in the cell periphery, when compared to the non-malignant controls (FIG. 5). There was also a dramatic reduction in actin staining for the prostate cancer compared to the non-malignant control cell lines (FIG. 5). In the non-malignant control cells, transferrin was clustered in LIMP-2 and Rab7 positive endosomes localised in the perinuclear region (FIG. 6). While the prostate cancer cells had some LIMP-2 positive staining in the perinuclear region and some co-localisation with the Golgi marker TGN46, the majority of transferrin was localised in different endosomal compartments (i.e. Appl1, Rab5A, EEA1) distributed throughout the cytoplasm and in cellular extensions (FIG. 6). The Rab4 recycling endosomes and LAMP-1 positive lysosomes had similar patterns of transferrin staining for the prostate cancer and non-malignant control cell lines (FIG. 6). Further analysis of the transferrin receptors revealed variable gene and protein expression for TfR1 and TfR2 (FIG. 7). There was a significant increase in TFR1 gene expression in prostate cancer cells when compared to non-malignant controls, but only a qualitative increase in TFR1 protein in the prostate cancer cell line 22RV1 and not for LNCaP (FIG. 7A). While there was significantly more TFR2 protein detected in prostate cancer cells when compared to the non-malignant controls, there was only and increase in TFR2 gene expression observed in LNCaP (FIG. 7A). Thus, while there was an increased amount of TFR protein in prostate cancer compared to non-malignant control cells, there was relatively more TFR1 in 22RV1 and more TFR2 in LNCaP cells.

(iv) Altered Akt Signalling in Prostate Cancer Cells

Figure 8:
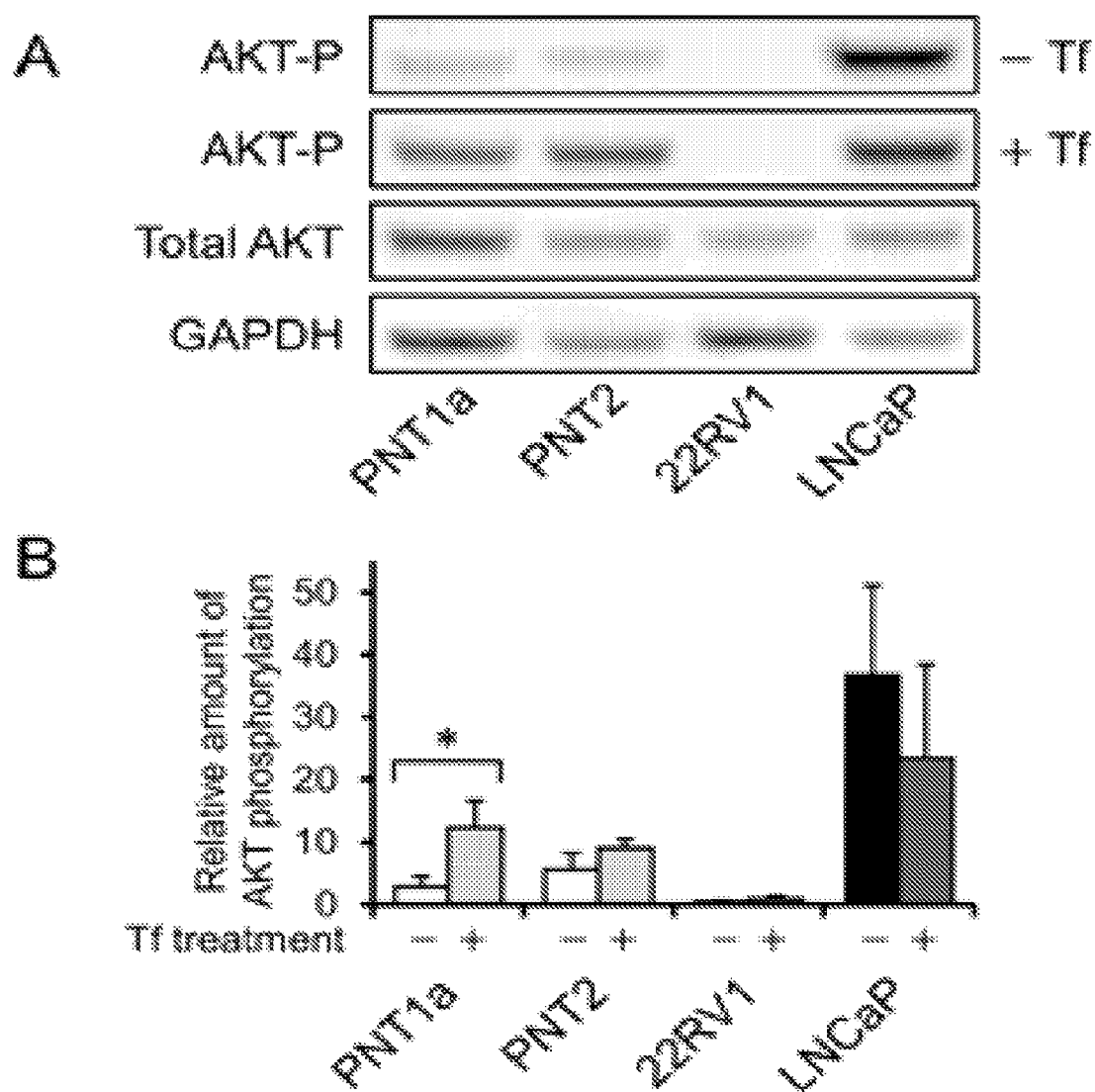
FIG. 8 shows AKT phosphorylation levels in non-malignant control and cancer cell lines before and subsequent to transferrin treatment.

The total amount of Akt protein detected in non-malignant control cells was similar to that detected in prostate cancer cells (FIG. 8). There were, however, differences in the amount of phosphorylated Akt in the prostate cancer lines, with 22RV1 showing a marked reduction in the amount of phosphorylated Akt whereas LNCaP had increased amount of phosphorylated Akt (FIG. 8). More importantly, following the addition of transferrin, there was a significant increase in the amount of phosphorylated Akt in non-malignant control cells, but no change in the amount of phosphorylated Akt in either of the cancer cells (FIG. 8B). Interestingly, the increased amount of phosphorylated Akt observed in the LNCaP cells (that had not been treated with transferrin), correlated with the amount of TfR2 detected in this cell line (FIG. 7A and FIG. 8).

(v) Distribution of LAMP-1 and APPL1 in Non-Malignant and Malignant Human Prostate Tissue.

Figure 9:
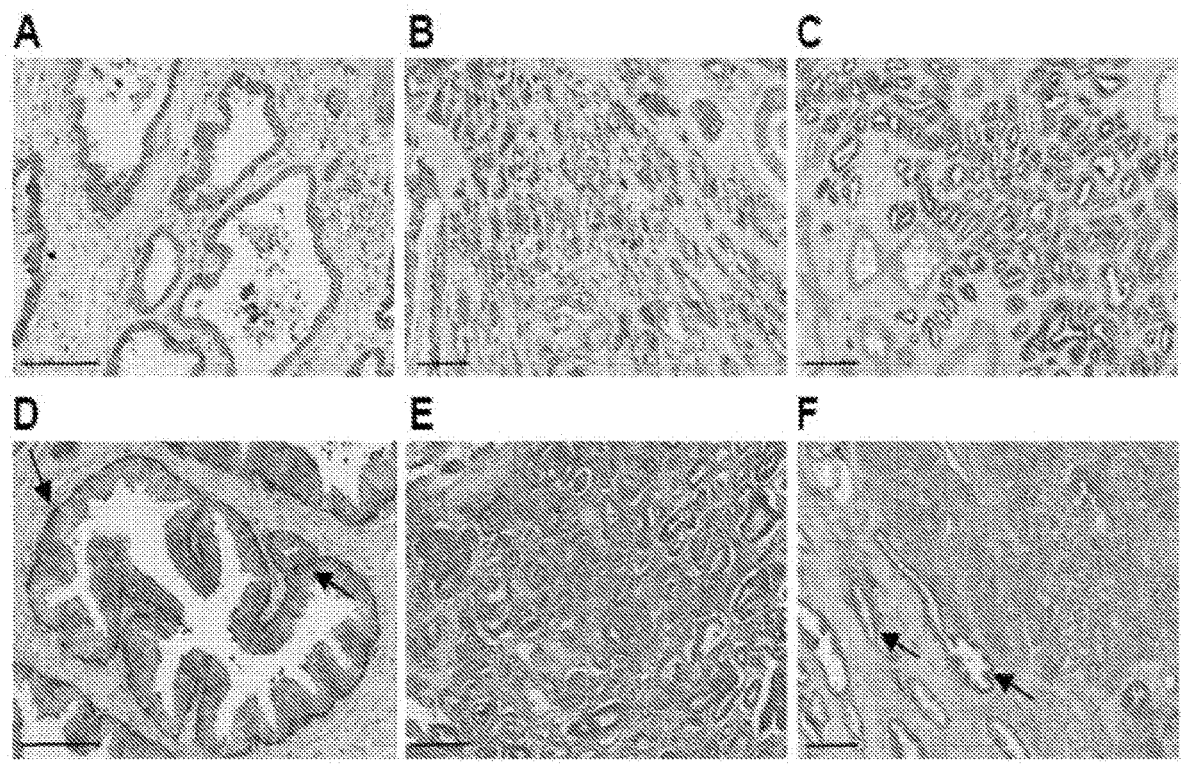
FIG. 9 shows LAMP-1 and APPL1 expression in prostate tissue isolated from different cases. LAMP-1 and APPL1 expression in matched human non-malignant (A, D) and tumour (B, E) prostate tissue. Both non-malignant and malignant tissue is stained for LAMP-1 (C) and APPL1 (F). The arrows in D & F show APPL1 staining the basement membrane in non-malignant prostate tissue. Scale bar=100 μM in A, B & D and 200 μM in C, E, F.

Immunohistochemistry was used to investigate the distribution of LAMP-1 and APPL1 in prostate cancer patient tissue samples. The lysosomal marker LAMP-1 showed some tumour specific staining in some patient samples (FIG. 9), but consistent with previous studies, there was variable results and some patient samples had little or no LAMP-1 staining (data not shown). APPL1, however, specifically delineated the cancer margins and showed dramatically increased staining within the tumour mass (FIG. 9). This APPL1 staining pattern was consistent for each of the 6 different patient samples examined.

Discussion

Prostate cancer is one of the most frequently diagnosed cancers in men and a leading cause of cancer related deaths world-wide, particularly in the United States and Australasian populations. The prostate specific antigen is still a commonly used test to detect prostate cancer, but has significant problems in terms of miss-diagnosis and prognostic prediction. Some promising adjunct tests have recently been developed including prostate cancer antigen 3 (PCA3), the analysis of cholesterol sulphate and a novel sequence of the gene protein kinase C-zeta (PRKCZ) which is translated to the protein PRKC-$\zeta$-$_{PrC}$. However, these biomarkers have a number of deficiencies that do not provide a useful method for the early and accurate detection of prostate cancer to enable appropriate therapeutic intervention.

There have been extensive protein and proteomic studies to delineate potential new prostate cancer biomarkers, but despite this, suitable markers have yet to be identified.

Here we observed altered distribution of endosome and lysosome vesicles into the cellular periphery of prostate cancer cells. Increases in $Na^+/H^+$ exchange activity (acidification), RhoA GTPase activity and PI3K activation have been shown to result in exocytosis from prostate cancer cells. The increased endosomal associated gene and protein expression, suggested that endosome related proteins may provide an important new focus for prostate cancer disease marker studies.

We observed increased gene and protein expression of the endosomal protein LIMP-2 in prostate cancer cell lines, prompting us to investigate endosomal biogenesis in prostate cancer cells. The early endosome associated proteins EEA1, APPL1, APPL2 and recycling endosome protein Rab4 were significantly upregulated in prostate cancer cells, supporting the hypothesis of altered endosome biogenesis in prostate cancer. Furthermore, the EEA1, APPL1 and APPL2 endosome sub-populations each displayed altered intracellular distribution consistent with altered endosome traffic and potentially function.

The significant changes that we observed in endosome associated gene and protein expression, together with the altered distribution of endosome populations prompted us to investigate transferrin receptor expression together with transferrin endocytosis, sorting and Akt signalling as measures of endosome function. Akt signalling is also essential for regulating cell growth and survival; and this controls the cell surface expression of transferrin and growth factor receptors. The transferrin receptor has previously been observed to colocalise with Rab5 and the motor protein myosin VI; the latter of which is involved in retrograde transport to the plasma membrane. This was consistent with our observations of endosome populations co-staining with labelled transferrin in the cellular periphery of prostate cancer cells. There also appeared to be a deregulation of Akt signalling in the prostate cancer cells, which may have altered the intracellular location of the transferrin receptor, routing it into the different populations of APPL1, APPL2 and Rab5 endosomes.

APPL1 has been shown to be directly involved in insulin signalling and the translocation of the glucose transporter GLUT-4, which is mediated by direct binding of APPL1 to PI3K and Akt. The increased gene and protein expression of APPL1 that we observed in prostate cancer cells might be expected to cause increased glucose uptake, due to its effect on GLUT-4 and this could have implications for energy metabolism in these cancer cells. Indeed, APPL1 also regulates other aspects of both lipid and glucose metabolism, activating AMP-activated kinase, p38 MAP kinase (MAPK) and PPARα. APPL2, a relation of APPL1, has been shown to function as a negative regulator of adiponectin signalling, by competitive binding with APPL1 for interaction with the adiponectin receptor, again regulating energy metabolism. The increased expression of both APPL1 and APPL2 could therefore impact heavily on prostate cancer cell metabolism, particularly as these proteins were not observed together, but rather on separate populations of endosomes. This could have direct significance for increased energy utilisation and prostate cancer cell survival. The altered APPL1 expression and effect on Akt signalling in prostate cancer cells would be expected to also have significant consequence for other aspects of prostate cancer biology, due to the importance of the APPL1/PI3K/Akt signalling pathway in leading cell adhesion and cell migration. Notably, APPL1 also acts as a mediator of other signalling pathways, by interaction with the cytosolic face of integral or membrane associated proteins either at the cell surface or in the endosome pathway; where it is directly involved in endosome traffic.

Rab GTPases are integrally involved in the control of endosome traffic, cycling between the cytoplasmic GDP bound state and the active membrane associated GTP bound state. Rab5 and Rab7 respectively define early and late endosome compartments and during endosome maturation Rab5 recruits the HOPS complex as a mechanism to activate and be replaced by Rab7. mVps39 is known to be a guanine nucleotide exchange factor (GEF), which promotes the GTP bound state on endosomal Rabs, while TBC-2/TBC$_1$D$_2$ is a Rab GTPase activating protein (GAP) that promotes the GDP bound state; which in combination is used to regulate the membrane localisation of Rab proteins. TBC-2/TBC$_1$D$_2$ is thought to act as a regulator of endosome to lysosome traffic and is required to maintain the correct size and distribution of endosomes. The altered distribution of endosome populations that we observed in prostate cancer cells suggests that TBC-2/TBC$_1$D$_2$ (GAP) and or mVps39 (GEF) might be functionally impaired. Interestingly, microarray analysis has detected increased expression of TBC-2/TBC$_1$D$_2$ and reduced Vps39 mRNA.

The Gleason grading system to define histological differentiation is used in conjunction with marker analysis to predict the course of disease in prostate cancer patients. We observed increased amounts of APPL1 protein in tissue biopsies from prostate cancer patients, confirming the increased gene and protein expression of APPL1 in prostate cancer cell lines.

We have demonstrated increased expression of early endosome markers and altered localisation of endosome and lysosome compartments in prostate cancer cells, which is associated with altered endocytosis and recycling of the transferrin receptor. We concluded that endosome biogenesis and function is altered in prostate cancer cells, opening a potentially new avenue of investigation, to develop markers that aid in the diagnosis and prognosis of prostate cancer.

Example 2—Lysosomal Enzymes as Potential Prostate Cancer Biomarkers

Materials and Methods (i) Antibody Reagents

The primary antibodies used in this study included rabbit polyclonal antibodies against hK2 (1 µg/mL, Abcam PLC, Cambridge, United Kingdom, cat #ab40948), hK3 (1 µg/mL, Abcam, cat #ab40949), hK4 (1 µg/mL, Abcam, cat #ab40950), hK15 (1 µg/mL, Abcam, cat #ab40961), acid ceramidase (1 µg/mL, Abcam, cat #ab74469). Mouse monoclonal antibodies against prostatic acid phosphatase (1 µg/mL, Abcam, cat #ab75704), cathepsin B (0.25 µg/mL, Abcam, cat #ab58802), cathepsin D (5 µg/mL, Abcam, cat #ab6313). Sheep polyclonal antibodies against α-glucosidase (1 µg/mL), β-glucosidase (1 µg/mL) and α-galactosidase A (1 µg/mL) were a kind gift from the Lysosomal Diseases Research Unit (Women's and Children's Hospital, SA Pathology Services, Adelaide, South Australia); and the LAMP-1 (1 µg/mL) mouse monoclonal BB6 was from Umea University, Umea, Sweden. The horseradish-peroxidase (HRP) conjugated secondary antibodies for Western blotting included anti-goat/sheep immunoglobulin (1/2000, Merck Millipore Pty. Ltd., Victoria, Australia), anti-rabbit immunoglobulin (1/2000, Sigma Aldrich Pty. Ltd., New South Wales, Australia), anti-mouse immunoglobulin (1/2000 Sigma Aldrich Pty. Ltd.), and HRP-conjugated anti-GAPDH (1/20000 Sigma Aldrich Pty. Ltd.).

(ii) Cell Lines and Culture Conditions

The cell lines PNT1a and PNT2, 22RV1 and LNCaP clone FCG were obtained from the European Collection of Cell Cultures via CellBank Australia (Children's Medical Research Institute, New South Wales, Australia). Cell lines RWPE-1, CaHPV10 and DU-145, were obtained from the American Tissue Culture Collection via Cryosite (Cryosite Ltd., New South Wales, Australia). These cell lines are absent from the list of cross-contaminated or misidentified cell lines, version 6.8 (9 Mar. 2012). Cell lines were maintained in culture media recommended by the ATCC and ECCC. PNT1a, PNT2 and 22RV1 cell lines were cultured in Roswell Park Memorial Institute (RPMI) 1640 media (Gibco®, Life Technologies Australia Pty Ltd., Victoria, Australia), supplemented with 10% foetal calf serum (FCS; In Vitro Technologies Pty Ltd., Victoria, Australia) and 2 mM L-glutamine (Sigma Aldrich Pty Ltd., New South Wales, Australia). The RWPE-1 and CaHPV10 cell lines were cultured in Keratinocyte Serum-Free Media (K-SFM) containing L-glutamine (Gibco®), supplemented with the supplied human recombinant epidermal growth factor 1-53 (EGF 1-53) and bovine pituitary extract (BPE). The DU-145 cell line was cultured in minimum essential medium (MEM) (Gibco®) and supplemented with 2 mM L-glutamine and 10% FCS. LNCaP was cultured in RPMI-1640 media supplemented with 2 mM L-glutamine, 10% FCS, 10 mM HEPES and 1 mM sodium pyruvate. Cells were incubated in a humidified incubator at 37° C. with 5% $CO_2$.

(iii) Cell Extract Preparation

The culture medium was aspirated from 80-90% confluent cell cultures, the cells washed once with PBS, and then incubated with 800 µL of a 20 mM Tris (pH 7.0), 500 mM sodium chloride and 2% SDS solution. Cells were harvested and a cell extract prepared by heating to 65° C. and sonication for one minute. The resulting lysate was then passaged 6 times through a 25-gauge needle. Total protein in the cell extracts was quantified using a bicinchoninic acid assay, according to the manufacturer's instructions (Micro BCA kit, Pierce, Rockford, IL, USA).

(iv) Western Blotting

Ten micrograms of cell lysate was heat-denatured (5 minutes at 100° C. in NuPAGE® LDS Sample Buffer and reducing agent) then electrophoresed at 120 V for 1.5 hours using pre-cast gels in an XCell SureLock Mini-Cell system (Life Technologies Australia Pty Ltd., Victoria, Australia). The protein was then transferred to polyvinylidene difluoride membranes (Polyscreen®, PerkinElmer, Victoria, Australia). The transfer membranes were blocked for 1 hour at room temperature using 5% (w/v) skim milk solution in 0.1% (v/v) TBS-tween and incubated with primary antibody overnight at 4° C. The membranes were washed 3×5 min in 0.1% (v/v) TBS-tween and then incubated with the appropriate HRP-conjugated secondary antibody diluted 1/2000 in block solution. The membranes were developed using a Novex® ECL chemiluminescent substrate reagent kit (Life Technologies Australia Pty Ltd., Victoria, Australia), and proteins visualised using an ImageQuant™ LAS 4000 imager (GE Healthcare Bio-Sciences Pty Ltd., New South Wales, Australia). Triplicate samples were analysed and images quantified relative to a reference GAPDH loading control using AlphaViewSA™ software v3.0.0.0 (ProteinSimple, Santa Clara, California). Kruskal-Wallis rank sum statistical analyses were performed using Stata/SE v11.2 (StataCorp LP, Texas, U.S.A) to determine significance between non-malignant control and cancer cell line groups (95% confidence limit; $p<0.05$).

Results (i) Detection of Current Prostate Cancer Biomarkers in Prostate Cancer Cell Extracts and Culture Media.

Figure 10:
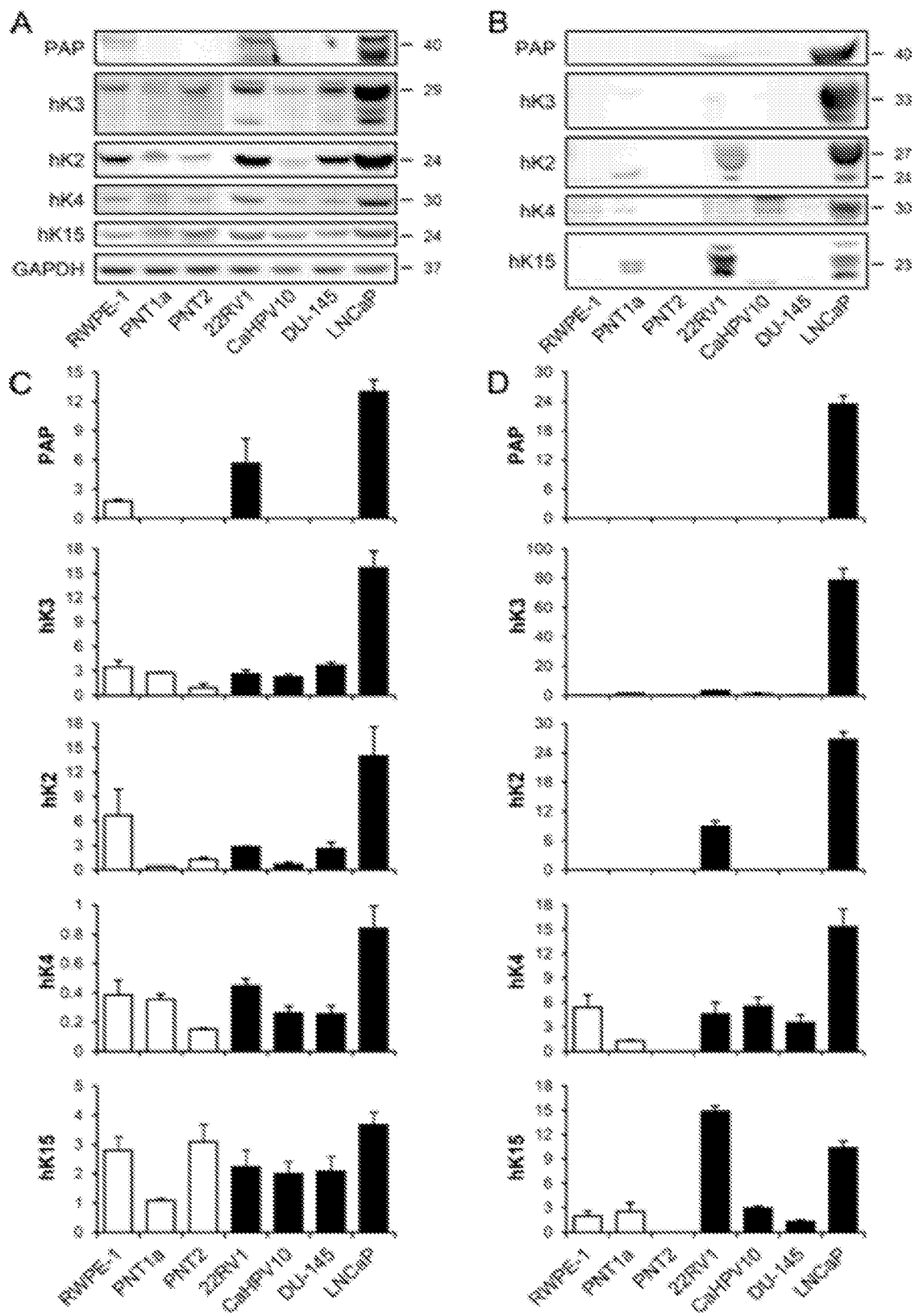
FIG. 10 shows detection and quantification of known prostate cancer biomarkers in non-malignant and prostate cancer cell lines. Western blots of biomarkers/GAPDH in cell extracts (A; 50 μg of whole cell lysate) and culture media (B; 3 mL culture media, collected after 48 hours incubation with confluent cells) from the non-malignant control cell lines RWPE 1, PNT1a and PNT2, and prostate cancer cell lines 22RV1, CaHPV10, DU 145 and LNCaP. Western blots are a representative of triplicates. The amount of each intracellular (C) or secreted (D) protein was quantified from the Western blots by densitometry relative to GAPDH (endogenous control). Non-malignant cell lines are depicted by white bars and prostate cancer cell lines by black bars and results represent the mean±SE (n=3).

Western blotting was used to define the amount of prostatic acid phosphatase (PAP), prostate-specific antigen (hK3) and other kallikreins (hK2, hK4 and hK15) in cell lysates and culture media from the non-malignant prostate cell lines (RWPE-1, PNT1a and PNT2) and the prostate cancer cell lines (22RV1, LNCaP, CaHPV10 and DU-145; FIG. 10). While the intracellular amount of PAP was higher in the prostate cancer cell lines 22RV1 and LNCaP, when compared to the non-malignant control cell lines, little or no protein was detected in the CaHPV10 and DU-145 prostate cancer cell lines. Similarly, hK2, hK3 and hK4 showed increased amounts of intracellular protein in LNCaP when compared to the non-malignant control cell lines, but minimal amounts were detected in the other prostate cancer cell lines. The amounts of intracellular hK15 were similar for all of the prostate cancer cell lines, as well as the non-malignant control cell lines RWPE-1 and PNT2, albeit with a lower amount detected in PNT1a. PAP, hK3, hK2, and hK4 were secreted from LNCaP cells and the amount was increased when compared to the other prostate cancer and non-malignant control cell lines. Notably, the secretion of hK15 from 22RV1 and LNCaP was elevated when compared to the other prostate cancer and non-malignant control cell lines. These findings indicated variable protein content, and PAP/kallikrein secretion for the prostate cancer cell lines and an inability of these markers to distinguish between a number of prostate cancer and non-malignant control cell lines.

The detection of hK2, hK4 and hK15 in cell extracts revealed single molecular forms that could not be used to discriminate between non-malignant control and prostate cancer cell lines. Prostatic acid phosphatase was variably processed in the 22RV1 and LNCaP prostate cancer cell lines (40 and 38 kDa molecular forms) compared to the non-malignant cell line RWPE-1 (38 kDa form), but was absent from the other cell lines. Similarly, two molecular forms of hK3 were detected in 22RV1 and LNCaP prostate cancer cell lines (29 and 25 kDa), while the other control and cancer cell lines only expressed the 29 kDa molecular form. The detection of secreted hK2 and hK15 revealed molecular forms (27 kDa for hK2; 21 kDa and 25 kDa for hK15) that were similar to PNT1a but these molecular forms were not detected in the other non-malignant control and cancer cell lines. This indicated variable proteolytic processing in some prostate cancer cell lines when compared to the non-malignant control cell lines.

The secretion of kallikreins appeared to correlate with the androgen-receptor status of prostate cancer cell lines and the amounts secreted generally appeared to be independent of the amounts detected in the cell extracts. An increased secretion of hK3, hK2 and hK15 was observed from 22RV1 and LNCaP prostate cancer cell lines. However, the amount of hK2 was elevated in cell extracts from the RWPE-1 non-malignant cells when compared to 22RV1; while there was increased secretion of this marker from the 22RV1 cancer cell line compared to the RWPE-1 non-malignant control cell line. Elevated amounts of kallikreins are expected in cell lines that are responsive to androgen, or possessing activated androgen receptor, thereby activating genes containing androgen-response elements (AREs).

(ii) Detection of Lysosomal Proteins in Non-Malignant Control and Prostate Cancer Cell Extracts and Culture Media.

Figure 11:
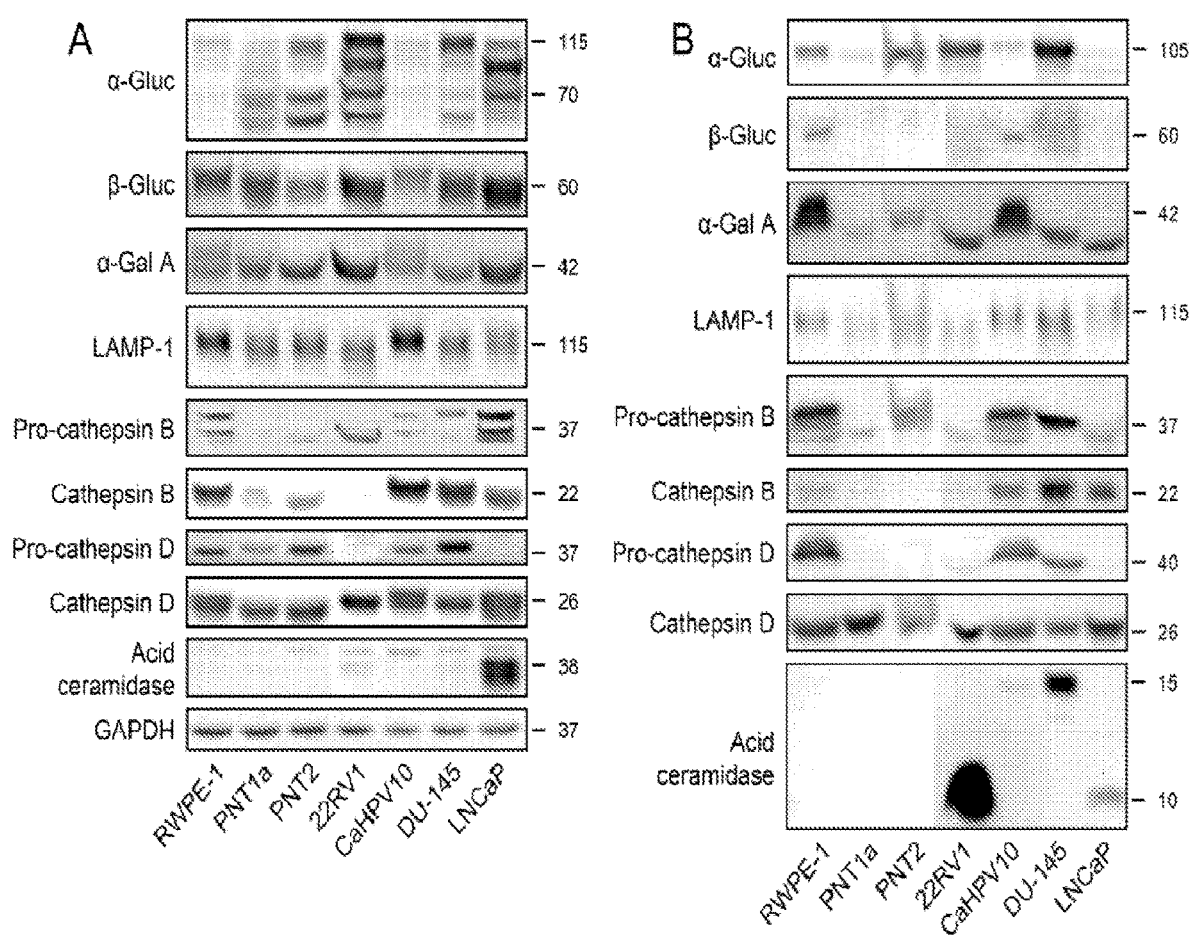
FIG. 11 shows detection of lysosomal proteins in non-malignant and prostate cancer cell lines. Western blots of lysosomal proteins/GAPDH in cell extracts (A; 50 μg of whole cell lysate) and culture media (B; 3 mL culture media, collected after 48 hours incubation with confluent cells) from the non-malignant control cell lines RWPE 1, PNT1a and PNT2, and prostate cancer cell lines 22RV1, CaHPV10, DU 145 and LNCaP. Western blots are representative of triplicate experiments.
Figure 12:
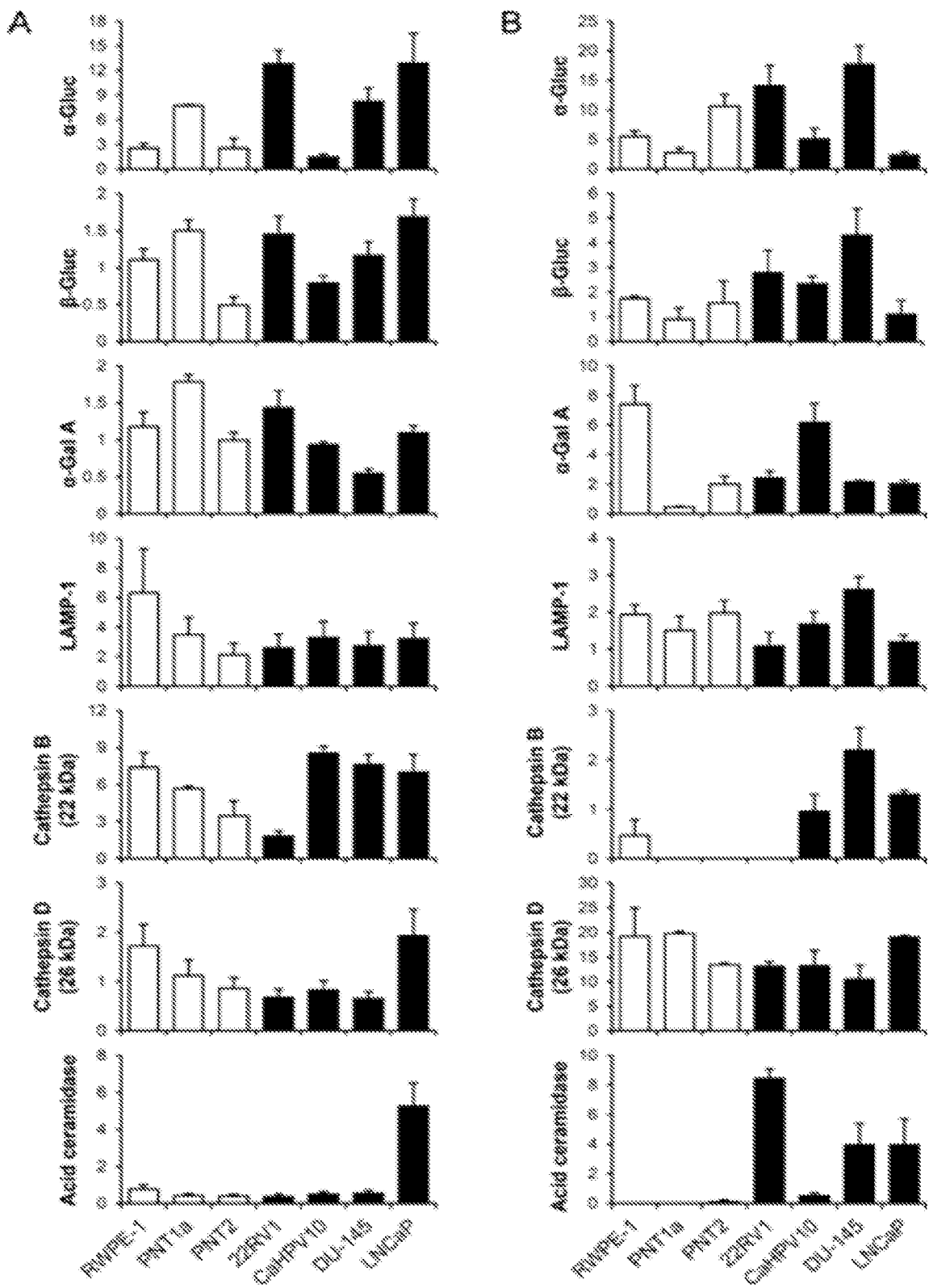
FIG. 12 shows quantification of lysosomal proteins in non-malignant and prostate cancer cell lines. The amount of each intracellular (A) or secreted (B) lysosomal protein was quantified from the Western blots (FIG. 12.2) by densitometry relative to GAPDH (endogenous control). Non-malignant cell lines are depicted by white bars and prostate cancer cell lines by black bars and results represent the mean±SE (n=3).

Western blotting was used to define the amount of different lysosomal proteins in cell lysates and culture media from non-malignant control and prostate cancer cell lines (FIG. 11, FIG. 12). The amounts of intracellular α-glucosidase (α-Gluc), β-glucosidase (β-Gluc), α-galactosidase A (α-Gal A), LAMP-1 and cathepsin D (26 kDa) was variable between the cell lines and could not differentiate non-malignant controls from the prostate cancer cell lines. The amount of pro-cathepsin D in cell extracts was similar for non-malignant control, CaHPV10 and DU-145 cancer cell lines, however there was no detectable protein in the cell extract of 22RV1 and LNCaP prostate cancer cell lines. The secretion of β-glucosidase, α-galactosidase, pro-cathepsin B and D was elevated in RWPE-1 when compared to the other non-malignant cell lines PNT1a and PNT2. The amount of α-galactosidase secreted from RWPE-1 was similar to that from the CaHPV10 prostate cancer cell line. The amount of LAMP-1 and cathepsin D (26 kDa) secretion was similar for each of the non-malignant control and prostate cancer cell lines. The 22RV1 and DU-145 prostate cancer cell lines had elevated secretion of α-glucosidase and β-glucosidase when compared to the other prostate cancer and non-malignant control cell lines. Limited amounts of Cathepsin B (22 kDa) was detected in the 22RV1 prostate cancer cell line when compared to the other prostate cancer and non-malignant control cell lines. The amount of pro-cathepsin B was elevated in LNCaP when compared to the other prostate cancer cell lines. RWPE-1 had an increased amount of pro-cathepsin B when compared to the PNT1a and PNT2 non-malignant control cell lines. The secretion of cathepsin B (22 kDa) was higher for CaHPV10, DU-145 and LNCaP prostate cancer cell lines compared to the non-malignant control cell lines and the 22RV1 prostate cancer cell line. Minimal amounts of acid ceramidase were detected in the non-malignant control cell lines and the prostate cancer cell lines 22RV1, CaHPV10 and DU-145. In contrast, large amounts of acid ceramidase were detected in cell extracts from the LNCaP cancer cell line. Acid ceramidase (10-15 kDa) was not secreted from the non-malignant control cell lines, but elevated amounts were secreted from the 22RV1, DU-145 and LNCaP prostate cancer cell lines when compared to CaHPV10 and the non-malignant control cell lines. These findings indicated variable intracellular content and secretion of lysosomal proteins for non-malignant control and prostate cancer cell lines, with a potential for cathepsin B and acid ceramidase to distinguish between non-malignant control and prostate cancer cell lines. The secretion of acid ceramidase and cathepsin B may therefore afford some capacity to distinguish between non-malignant and cancer cell lines.

Multiple molecular forms of α-glucosidase were detected in the cell extracts of non-malignant and prostate cancer cell lines. A 110 kDa molecular form of α-glucosidase was detected in 22RV1 and LNCaP cancer cell lines, but only minimal amounts were detected in the other prostate cancer and non-malignant control cell lines. The molecular weight of β-glucosidase and LAMP-1 varied between prostate cancer and non-malignant cell lines and was unable to discriminate between these types of cell lines. Two molecular forms of α-galactosidase A (42 and 43 kDa) were present in both CaHPV10 and RWPE-1 cell lines, but not in other prostate cancer or non-malignant cell lines. Both CaHPV10 and RWPE-1 displayed low amounts of the 70 kDa molecular form of α-glucosidase when compared to the other non-malignant and prostate cancer cell lines. Interestingly, in both RWPE-1 and CaHPV10 cell lines there was similar protein processing for α-glucosidase and α-galactosidase A, elevated molecular weight of β-glucosidase and elevated secretion amounts of α-galactosidase A, which differed from the other non-malignant and prostate cancer cell lines; and this correlated with the different technique used to immortalise these two cell lines. Two molecular forms of pro-cathepsin B (37 and 39 kDa) were detected in the cell extract of CaHPV10, DU-145 and LNCaP prostate cancer and RWPE-1 non-malignant control cell lines. A 60 kDa molecular form of β-glucosidase was secreted from RWPE-1 and CaHPV10 cells, which was more diffuse from the other cell lines and suggested variable glycosylation. The molecular weight of the secreted form of α-galactosidase A was lower in the prostate cancer cell lines 22RV1, DU-145 and LNCaP when compared to the non-malignant control cell lines and CaHPV10 prostate cancer cell line. The variable processing and increased secretion of some lysosomal proteins may have some capacity to distinguish between prostate cancer and non-malignant cell lines.

Example 3—Microarray Expression Profiling of Endosome and Lysosome Genes In Vivo The observations of altered endosome biology in prostate cancer cells suggested that the increased expression of specific endosomal gene and proteins might critically influence the development and or progression of prostate cancer. Altered endosome biogenesis may therefore provide a new avenue for the investigation of biomarkers that can be used for prostate cancer diagnosis and prognosis. However, it was important to correlate the in vitro observations with patient data, to establish that the novel changes are biologically relevant. Verifying that there was altered endosome-related gene expression in prostate cancer microarray databases was viewed as an important first step in this process.

Gene microarray databases enable the investigation of biomarker expression in patients and to determine any relation to known clinical parameters, which may then be used to predict clinical outcome.

To analyse endosome-lysosome gene expression in relation to patient outcome a range of prostate cancer microarray databases were selected for investigation. Multiple microarray cohorts are available for analysis from Oncomine (Life Technologies Pty., Ltd.) or the Gene Expression Omnibus. A recent cohort of patients treated by radical prostatectomy at the Memorial Sloan-Kettering Cancer Center (MSKCC) was also selected and herein referred to as the Taylor cohort. This cohort comprised 150 primary prostate cancer and 29 matched non-malignant control samples. For the Taylor cohort, specimens were collected and snap-frozen prior to the identification of cancer regions; RNA extraction was performed on samples containing greater than 70% cancer-cell content, based on histological assessment. Analysis was performed using an Affymetrix Human Exon 1.0 ST array with the resulting microarray data obtained from the cBio Cancer Genomics Pathway Portal. This cohort was also selected because it contained expression data for all of the relevant endosome and lysosome genes that were analysed in vitro. Further, the Affymetrix GeneChip® used in this cohort was created from sequences derived from the RefSeq database build 34 (July 2003), which provides greater sequence accuracy than previous microarrays using the Affymetrix GeneChip® HGU95. An additional microarray by Tomlins et al. was also analysed and herein referred to as the Tomlins cohort, which was generated using alternative microarray technology; specifically, a non-commercial custom-made array. This cohort comprised of non-malignant prostate tissue (n=27), prostatic intraepithelial neoplasia (PIN; n=13), primary cancer (n=32) and metastatic cancer tissue (n=20). Thus, in addition to confirming the results obtained for the Taylor cohort, the Tomlins cohort enabled the assessment of gene expression during disease progression from PIN through to metastatic cancer, which may be diagnostically relevant. Prostate samples for the Tomlins cohort were collected using laser-capture micro-dissection (LCM) with approximately 10,000 cells collected from each sample. This method of sample collection was advantageous since specificity to specific sample type can be increased, with tissue surrounding the cancer excluded from capture, leading to cleaner RNA preparation and analysis. The prostate cancer patient tissue analysed by Glinsky et al. included cancer patients that were monitored over the course of five years from initial cancer detection, to determine recurrence based on PSA levels post-therapy; and therefore provided a capacity to determine the prognostic capability of endosome or lysosome genes, by analysing expression during cancer progression. The analysis of these different microarray databases aimed to verify the altered gene expression, observed in vitro using cultured cells, as well as to provide some indication of the consistency for marker expression in patient samples.

Results (i) Expression of Lysosome-Related Genes in Prostate Cancer are Altered Independently of TFEB Expression.

Figure 13:
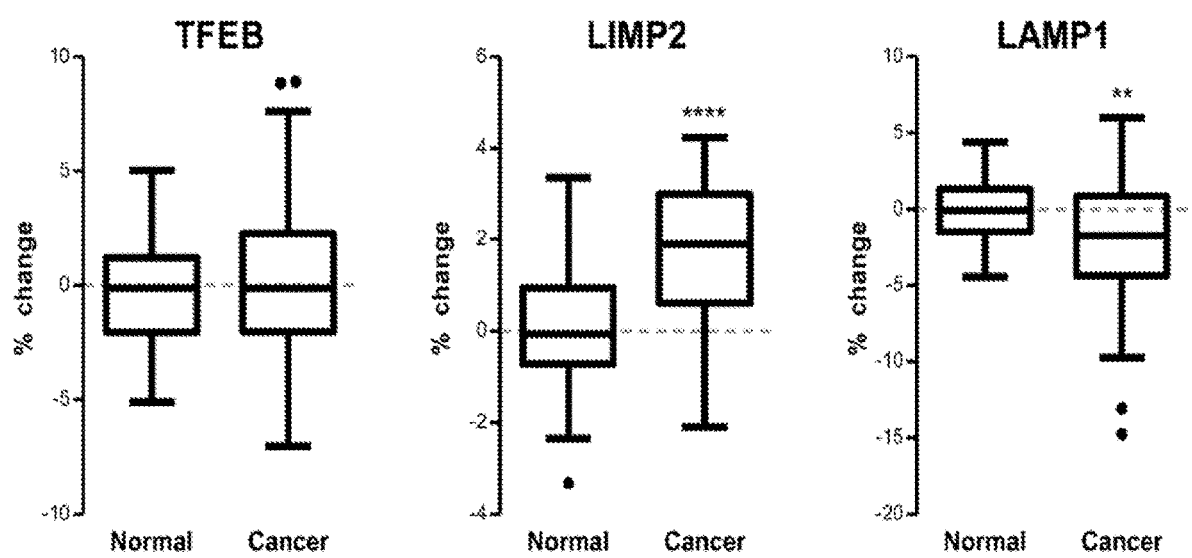
FIG. 13 shows LIMP2 and LAMP1 gene expression is altered independently of TFEB expression in prostate cancer. Expression profiling data derived from Affymetrix Human Exon 1.0 ST arrays of 150 primary prostate cancers and 29 non-malignant tissues {Taylor, 2010 #976} were quantitated to show percentage change of gene expression of TFEB, LIMP2 and LAMP1. Box-and-whisker graphs were plotted with Tukey outliers (black points). Statistical significance is represented by an asterisk ( P≤0.01; ** P≤0.0001).
Figure 14:
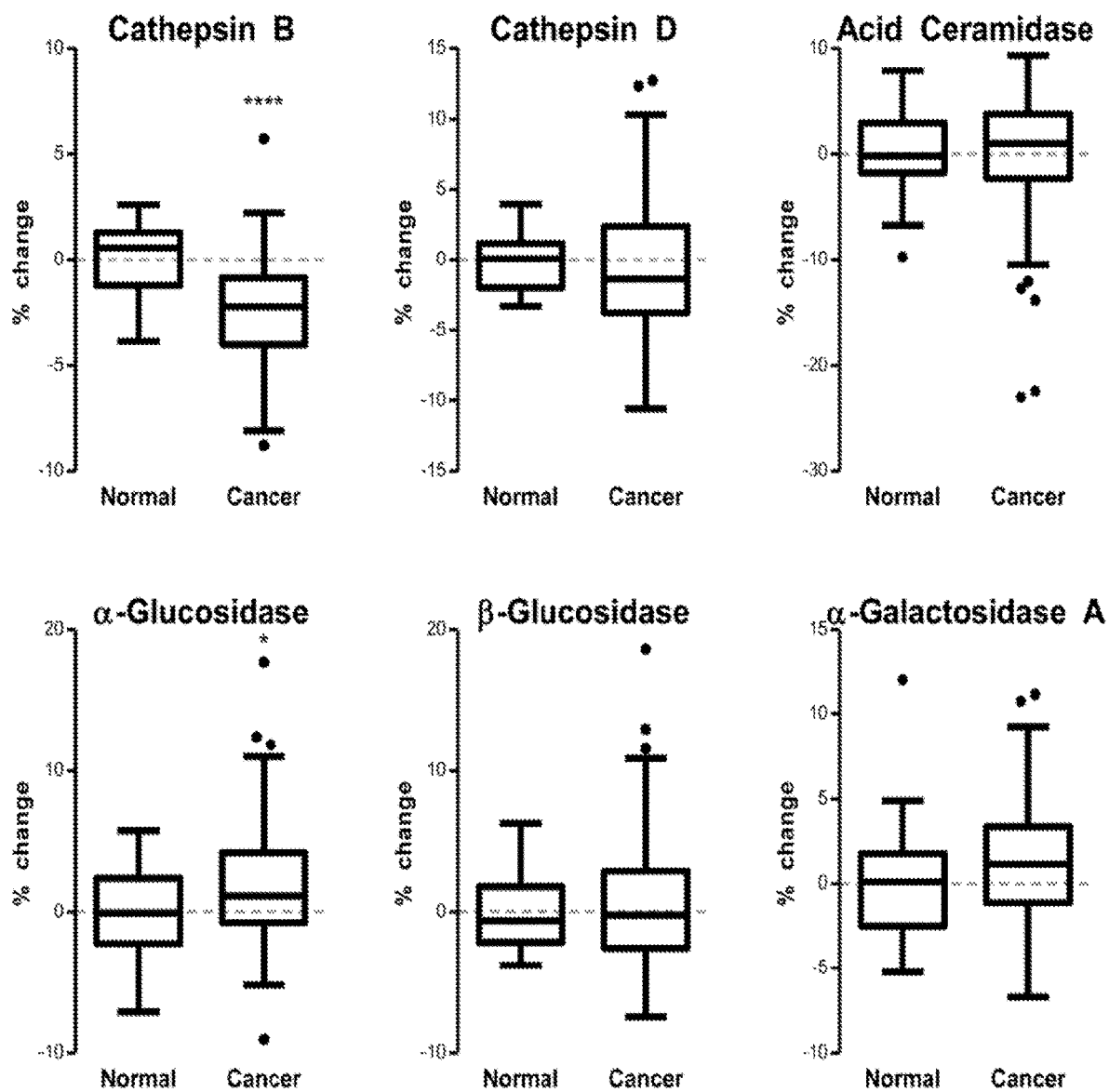
FIG. 14 shows TFEB-regulated lysosomal genes with variable expression in prostate cancer; cathepsin B had significantly reduced expression whilst α glucosidase had increased expression in prostate cancer. Expression profiling data derived from Affymetrix Human Exon 1.0 ST arrays of 150 primary prostate cancers and 29 non-malignant tissues {Taylor, 2010 #976} were quantitated to show percentage change of expression of lysosome-related genes. Box-and-whisker graphs were plotted with Tukey outliers (black points). Statistical significance is represented by an asterisk (* P≤0.05; **** P≤0.0001).

The transcription of lysosome-related genes such as LIMP2 that influence endosome and lysosome biogenesis is regulated by transcription factor EB (TFEB). Thus, TFEB gene expression may provide evidence of altered endosome and lysosome biology in vivo. Expression of TFEB was unchanged in prostate cancer compared to non-malignant control prostate tissue (FIG. 13), whilst expression of LIMP2 was significantly elevated in prostate cancer compared to non-malignant tissue ($P \leq 0.0001$). Conversely, LAMP1, which is also a target of TFEB, had significantly reduced expression in prostate cancer compared to non-malignant control tissue ($P \leq 0.01$). Other TFEB-regulated lysosomal genes were analysed to determine if their expression was altered independently of this transcription factor (FIG. 14). Cathepsin B (CTSB) showed significantly reduced expression in prostate cancer tissue when compared to non-malignant control tissue using the Taylor cohort ($P \leq 0.0001$), whilst α Glucosidase (GAA) had significantly elevated expression in prostate cancer compared to non-malignant control tissue ($P \leq 0.05$). The expression of acid ceramidase, β glucosidase (GBA) and a galactosidase A (GLA) were not significantly altered in prostate cancer tissue in the Taylor cohort when compared to non-malignant control tissue.

(ii) APPL1 had Significantly Elevated Expression in Primary Prostate Cancer Tissue.

Figure 15:
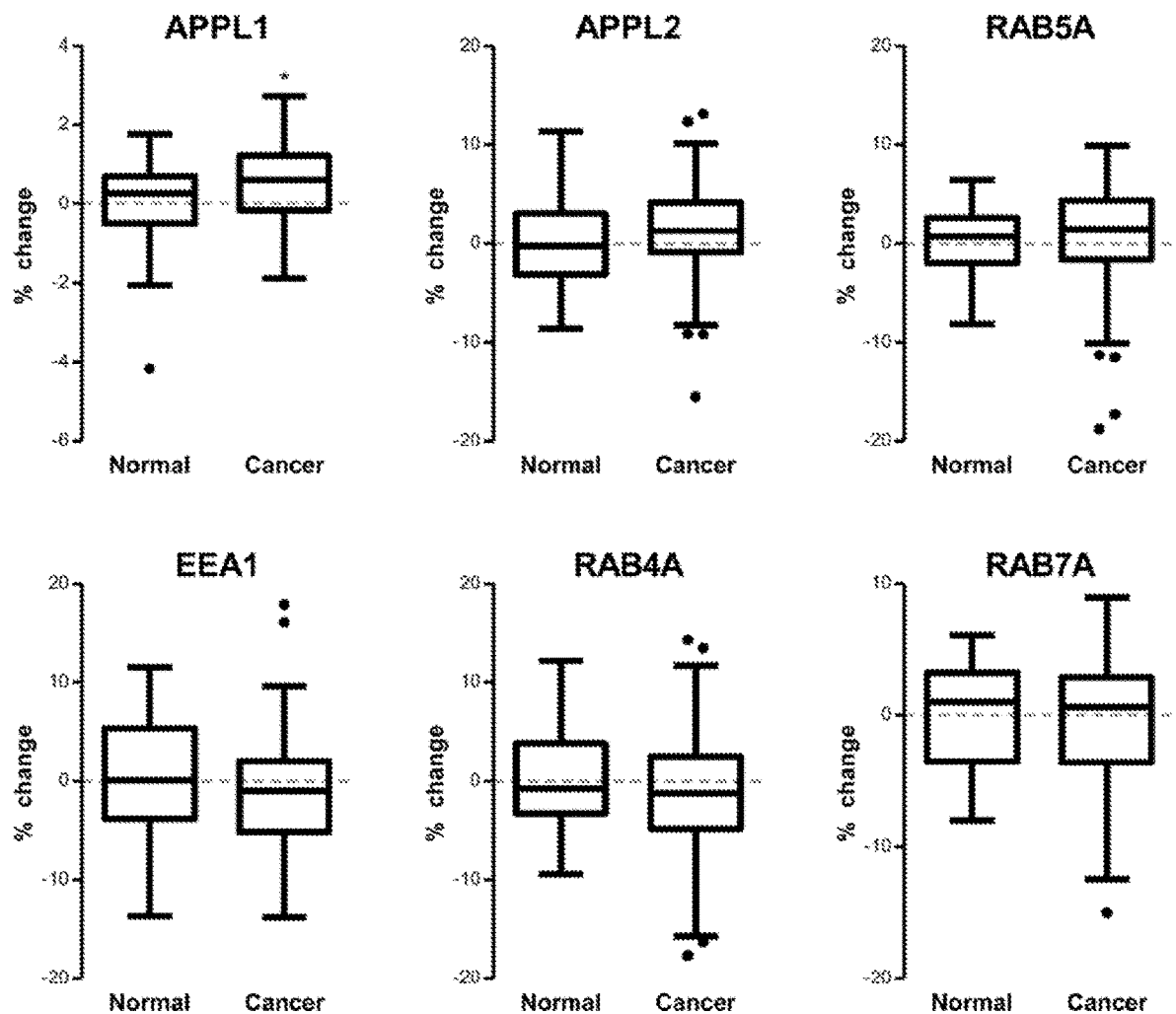
FIG. 15 shows APPL1 gene expression was significantly increased in prostate cancer whilst other endosome-related markers showed variable expression. Expression profiling data derived from Affymetrix Human Exon 1.0 ST arrays of 150 primary prostate cancers and 29 non-malignant tissues {Taylor, 2010 #976} were quantitated to show percentage change of expression of endosome-related genes. Box-and-whisker graphs were plotted with Tukey outliers (black points). Statistical significance is represented by an asterisk (* P≤0.05).

APPL1 gene expression was significantly elevated in prostate cancer tissue from the Taylor cohort when compared to non-malignant control tissue ($P \leq 0.05$; FIG. 15). However, while elevated expression of APPL2, RAB5A, EEA1, RAB4A and RAB7A were observed in vitro, there was no significant difference in expression of these endosome related genes in primary prostate cancer compared to non-malignant prostate tissue (FIG. 15).

(iv) Lysosomal Gene Expression (FIG. 16) and Early Endosome-Related Gene Expression (FIG. 17) was Altered During Cancer Progression.

Figure 16:
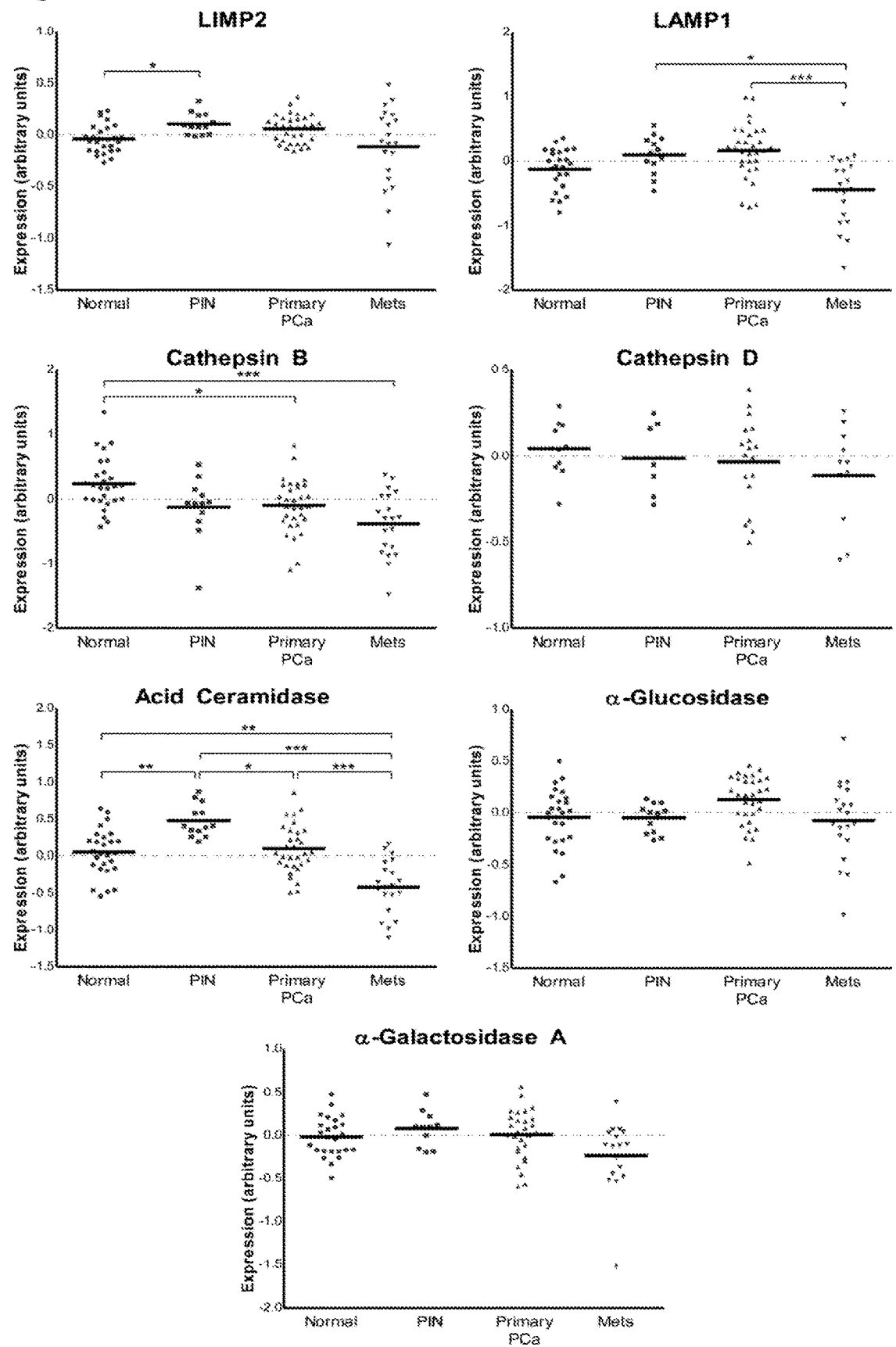
FIG. 16 shows lysosome gene expression data from the cohort by Tomlins et al. that mirror findings from the Taylor cohort. Detailed analysis of prostate cancer tissue revealed altered endosomal gene expression during prostate cancer progression. Expression profiling data derived from the Chinnaiyan Human 20K Hs6 array of 27 nonmalignant tissues, 13 prostatic intraepithelial neoplasia's, 32 primary prostate cancer and 22 metastatic cancer tissue samples {Tomlins, 2007 #974} were quantitated to show relative amount of expression of lysosome-related genes. Statistical significance is represented by an asterisk (* P≤0.05;  P≤0.01; * P≤0.001).

The expression of endosome and lysosome related mRNA transcripts was also analysed from the Tomlins cohort enabling the analysis of prostatic intraepithelial neoplasia (PIN) and metastatic cancer tissue in addition to primary cancer and non-malignant tissue. The expression data for some genes such as TFEB was unavailable due to the custom microarray technology used and more limited probe-set compared to the commercial microarray used by Taylor et al. The gene expression of LIMP2 and LAMP1 in the Tomlins cohort showed no significant change between non-malignant control and primary prostate cancer tissue (FIG. 16). Other TFEB-regulated genes displayed differential expression in the prostate cancer tissue when compared to non-malignant control tissue; cathepsin B was significantly reduced in primary cancer tissue compared to non-malignant tissue ($P \leq 0.05$), however there was no significant change in the expression of cathepsin D, acid ceramidase, a glucosidase or a galactosidase A between non-malignant tissue and primary cancer tissue from the Tomlins microarray (FIG. 16). No expression data was available for β glucosidase in this cohort.

Analysis of gene expression through the progressive disease states revealed a significant increase in LIMP2 expression in prostatic intraepithelial neoplasia (PIN) ($P \leq 0.05$; FIG. 16); variations of LIMP2 expression were observed in metastatic tissue, however the mean reduction was not statistically significant. LAMP1 expression was elevated in PIN and primary cancer compared to non-malignant tissue, with expression in metastatic tissue significantly reduced when compared with PIN ($P \leq 0.05$) and primary prostate cancer tissue ($P \leq 0.001$). Cathepsin B expression in primary prostate cancer and metastatic tissue was significantly downregulated when compared to non-malignant control tissue ($P \leq 0.05$ and $P \leq 0.001$ respectively). Cathepsin D expression showed some reduction through PIN, primary cancer and metastatic disease states, however this was not statistically significant when compared with non-malignant control tissue. In primary cancer tissue acid ceramidase displayed similar expression to that observed in non-malignant control tissue; however, PIN tissue expression was significantly elevated when compared to non-malignant control and primary cancer tissue ($P \leq 0.01$ and $P \leq 0.05$ respectively). The expression of ASAH1 was significantly reduced in metastatic prostate tissue when compared to non-malignant control ($P \leq 0.01$), PIN ($P \leq 0.001$) and primary cancer tissue ($P \leq 0.001$).

Figure 17:
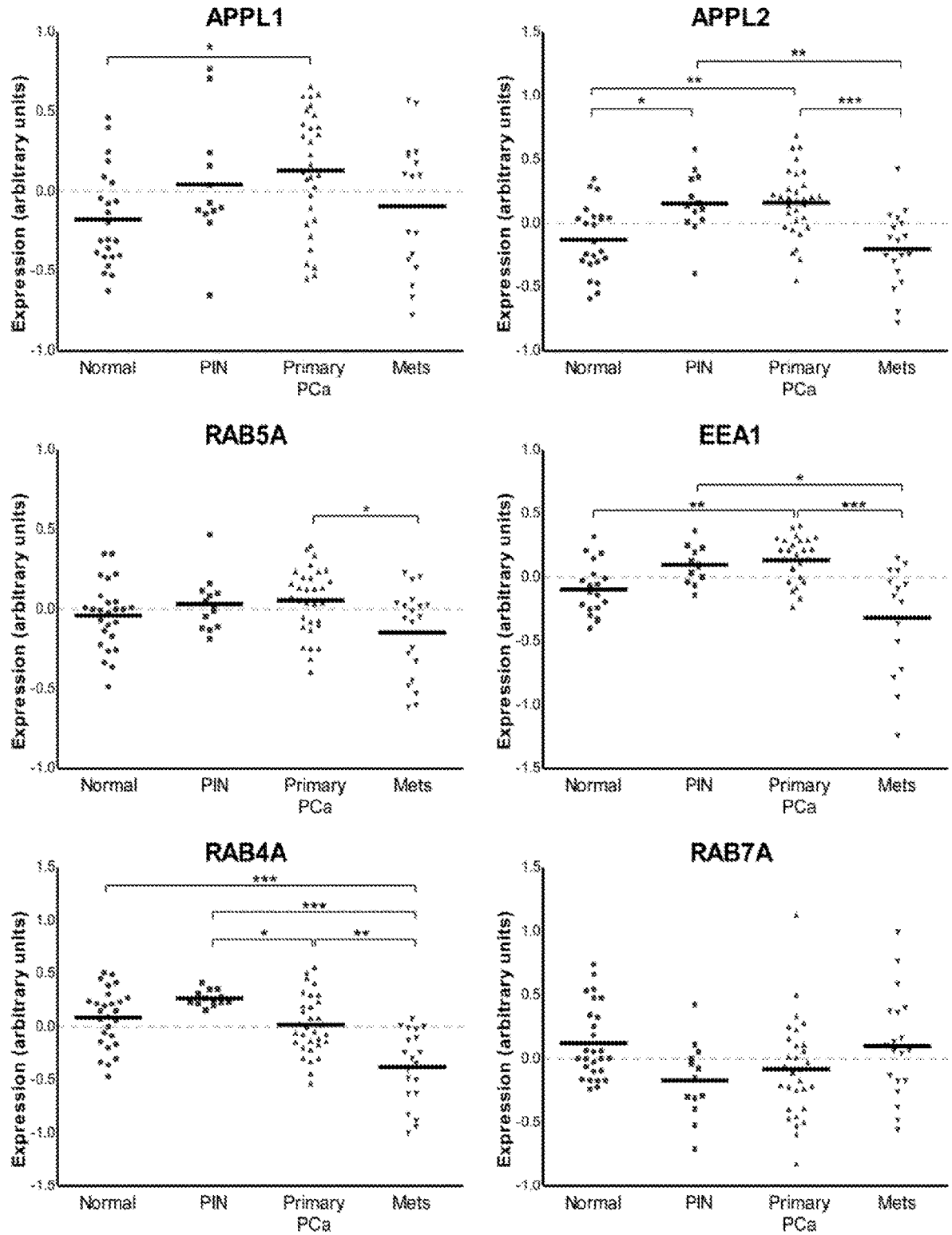
FIG. 17 shows expression of endosomal genes in the Tomlins cohort with significant increases, while metastatic prostate cancer tissue showed variable endosomal gene expression. Expression profiling data derived from the Chinnaiyan Human 20K Hs6 array of 27 nonmalignant tissues, 13 prostatic intraepithelial neoplasia's, 32 primary prostate cancer and 22 metastatic cancer tissue samples {Tomlins, 2007 #974} were quantitated to show relative amount of endosome gene expression. Statistical significance is represented by an asterisk (* P≤0.05;  P≤0.01; * P≤0.001)

APPL1 expression was significantly increased in primary prostate cancer compared to non-malignant control tissue ($P \leq 0.05$; FIG. 17); although there was no significant change in expression of APPL1 between metastatic prostate tissue and non-malignant tissue. The expression of APPL2 was significantly elevated in PIN and primary prostate cancer compared to non-malignant control tissue ($P \leq 0.05$ and $P \leq 0.01$ respectively); while metastatic tissue expressed similar amounts of APPL2 to non-malignant tissue, and this was significantly reduced when compared to PIN and primary prostate cancer tissue ($P \leq 0.01$ and $P \leq 0.001$ respectively). The expression of RAB5A was significantly reduced in metastatic prostate tissue when compared to primary prostate cancer tissue ($P \leq 0.05$), however there was no significant change in expression between non-malignant, PIN or primary prostate cancer tissue. The expression of EEA1 was significantly elevated in primary cancer compared to non-malignant tissue ($P \leq 0.01$); whereas a significant reduction was observed in EEA1 expression for metastatic tissue compared to primary prostate cancer ($P \leq 0.001$) and PIN tissue ($P \leq 0.05$). The expression of RAB4A was similar in primary prostate cancer compared to non-malignant control tissue; and the expression of RAB4A in PIN tissue was significantly elevated when compared to primary prostate cancer tissue ($P \leq 0.05$). There was a significant reduction in the expression of RAB4A in metastatic prostate tissue when compared to non-malignant control ($P \leq 0.001$), PIN ($P \leq 0.001$) and primary prostate cancer tissue ($P \leq 0.01$). There was no significant change in the expression of RAB7A observed in PIN, primary cancer or metastatic cancer from the Tomlins microarray when compared to non-malignant control tissue.

(v) Cathepsin B Appeared to Show Some Prognostic Value in Determining Survival Outcome for Prostate Cancer Patients.

Figure 18:
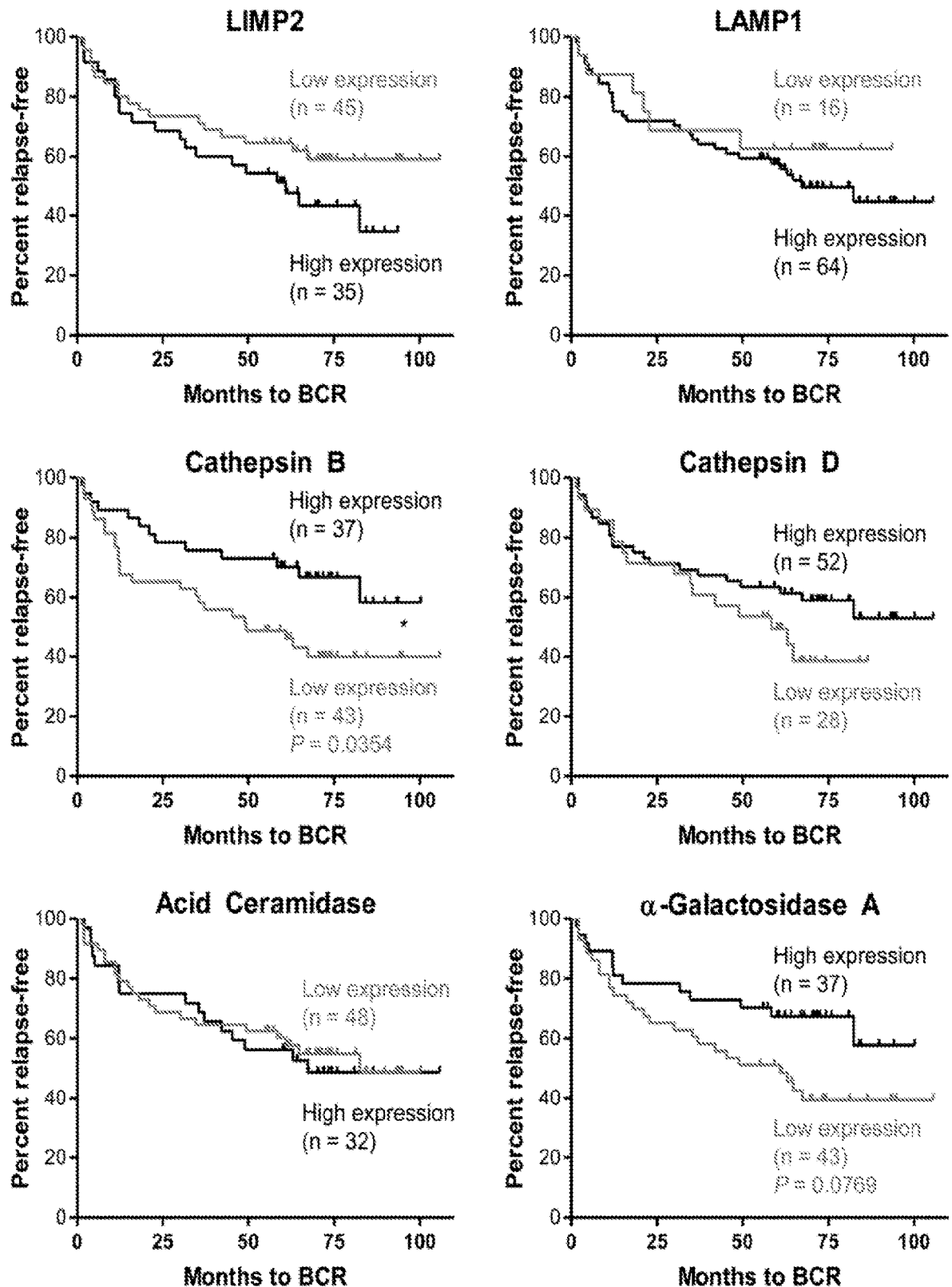
FIG. 18 shows Kaplan-Meier analysis of lysosomal genes and revealed cathepsin B as a candidate gene for patient stratification based on BCR. Cathepsin B differentiated patients at risk of relapse based on the amount of gene expression. Expression of lysosomal genes that have previously been observed to be significantly altered in primary cancer showed trends for differences between high and low-risk patients, but were not significant. Patients from the Glinsky cohort {Glinsky, 2004 #979} were stratified into two groups by K means clustering based on gene expression level (high—black line, low—grey line). Statistical analysis was performed using Gehan-Breslow-Wilcoxon test.
Figure 19:
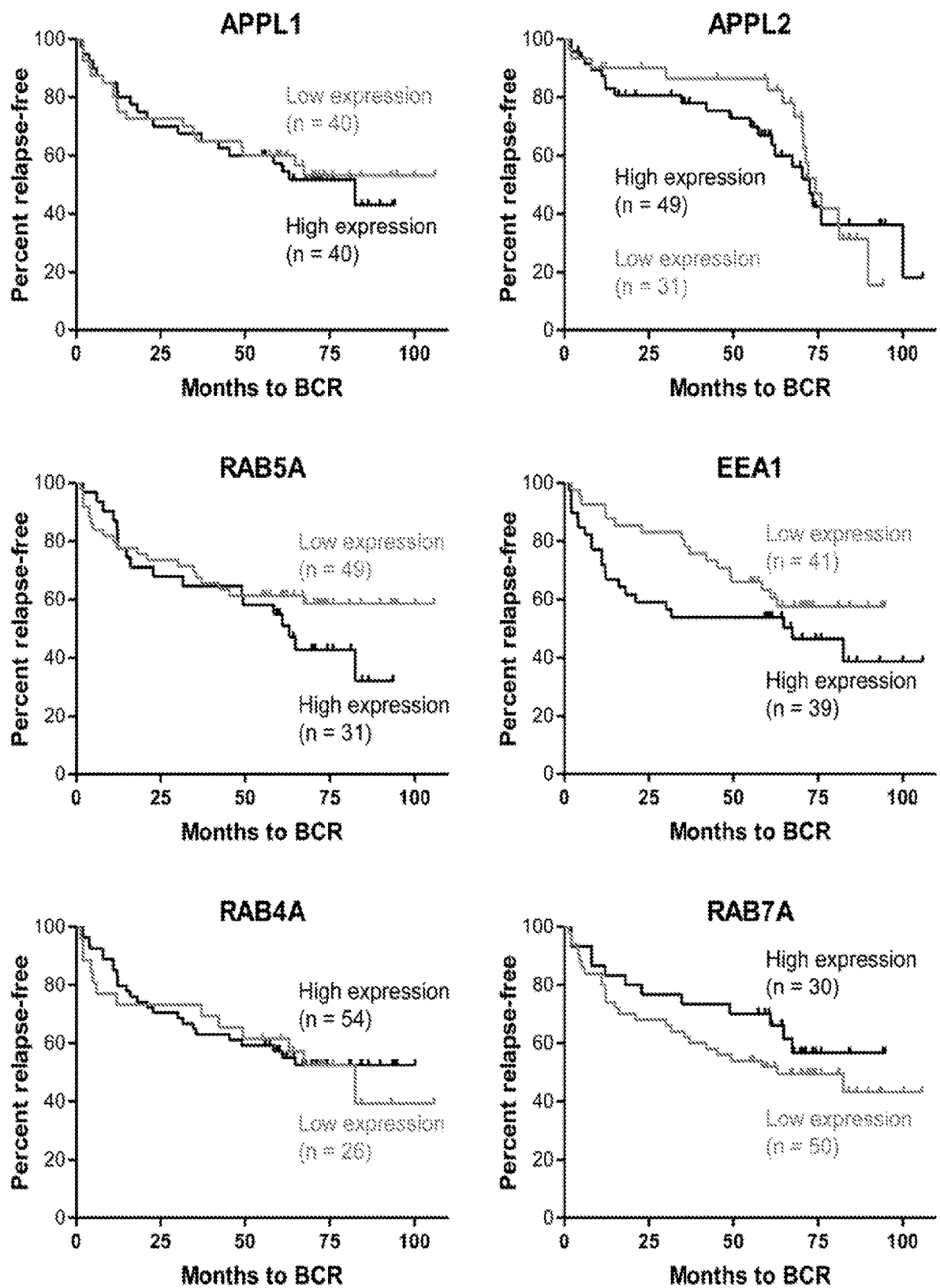
FIG. 19 shows endosomal gene expression did not stratify patients into significant prognostic groups. Patients from the Glinsky cohort were stratified into two groups by K means clustering based on amount (high—black line, low—grey line) of APPL1, APPL2, RAB5A, EEA1, RAB4A and RAB7A gene expression. Analysis was performed using Gehan-Breslow-Wilcoxon test; and no statistical significance was observed between the expression groups.

The quantification of gene expression may be a valuable tool for prostate cancer prognosis, as expression of some lysosome and endosome genes vary through PIN, primary cancer and metastatic cancer progression. To assess the prognostic potential of lysosomal genes, we classified patients from the Glinsky cohort into two groups using K means clustering based on gene expression. The Glinsky cohort microarray provides data of initial PSA levels detected upon biopsy, and information on relapse subsequent to therapy. Clustering of high or low cathepsin B expression, revealed patients with low amounts of cathepsin B expression who had significantly increased risk of biochemical recurrence (BCR). (FIG. 18). The grouping by high or low expression for LIMP2, LAMP1, cathepsin D, acid ceramidase or a galactosidase A genes did not stratify patients significantly into prognostic groups, however there was a trend observed for a galactosidase A ($P=0.077$; FIG. 18). From the increased expression of early endosome-related genes observed in the Taylor and Tomlins cohorts, we analysed the potential of these early endosome-related genes to stratify patients into prognostic groups (FIG. 19). However, classifying patients into two groups based on expression of individual early endosome genes by K means clustering did not significantly separate patients into prognostic groups.

(vi) Kaplan-Meier Analysis of Lysosome and Endosome Gene Expression Showed Significant Prognostic Value in Cancer Patients Expressing Low PSA Protein Levels.

Figure 20:
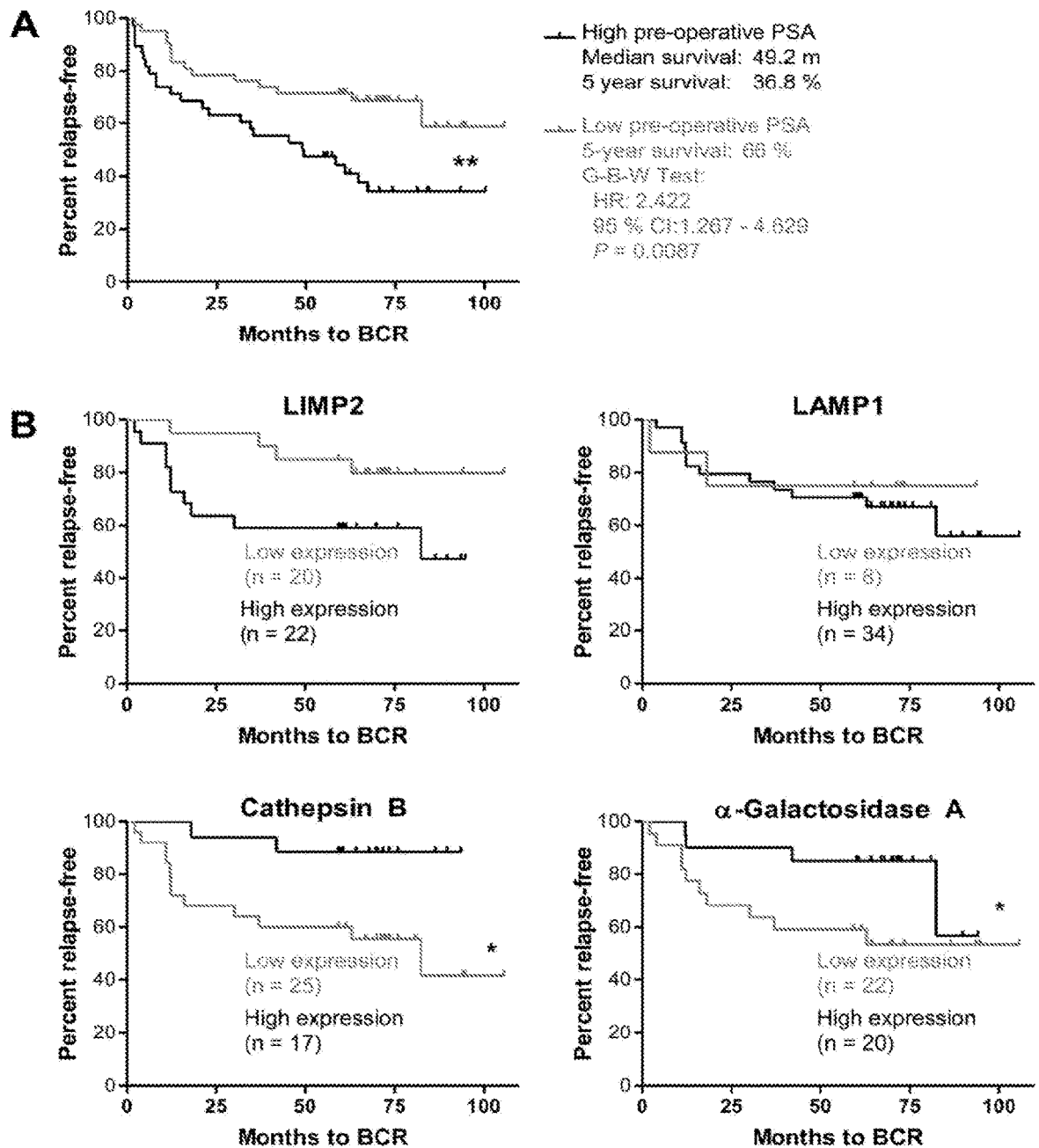
FIG. 20 shows Kaplan-Meier analysis of lysosomal gene expression showed significant capability for prognosis in patients expressing low PSA protein based on cathepsin B and a galactosidase A expression. (A) Pre-operative PSA level of 7.8 ng/mL was used as a cut-off discrimination level for patient's stratification into poor- and good-prognosis subgroups. (B) From the good-prognosis subgroup of PSA ≤7.8 ng/mL, patients were further stratified into two groups by K-means clustering based on gene expression of LIMP2, LAMP1, cathepsin B or a galactosidase A (high expression—black line, low expression—grey line). Statistical analysis was performed using Gehan-Breslow-Wilcoxon test. Statistical significance is marked by an asterisk (* P≤0.05; ** P≤0.01). (C) Multivariate analysis of gene expression in prostate cancer recurrence. BCR: biochemical recurrence; G-B-W: Gehan-Breslow-Wilcoxon test; HR: hazard ratio; CI: confidence interval.

Patients expressing PSA protein greater than 7.9 ng/mL at the time of diagnosis had a significantly increased risk of BCR when compared to the low-expression group (HR 2.422, $P=0.0087$; FIG. 20); however there was a proportion of patients (34%) with BCR that expressed low PSA that would benefit from improved diagnostic and prognostic assays. Stratification of patients with PSA $\leq 7.8$ ng/mL into high and low gene expression groups revealed a trend of high LIMP2 expression to result in increased BCR (FIG. 20B). The expression of LAMP1 did not appear to show any prognostic value. Clustering by cathepsin B expression indicated that patients in the low expression group were at significant risk of BCR when compared to those in the high expression group (HR 0.2752, $P=0.019$; FIG. 20 B). Low expression of a galactosidase A was also able to stratify patients into a group with higher risk of BCR (HR 0.3859, $P=0.0396$; FIG. 20 B).

Figure 21:
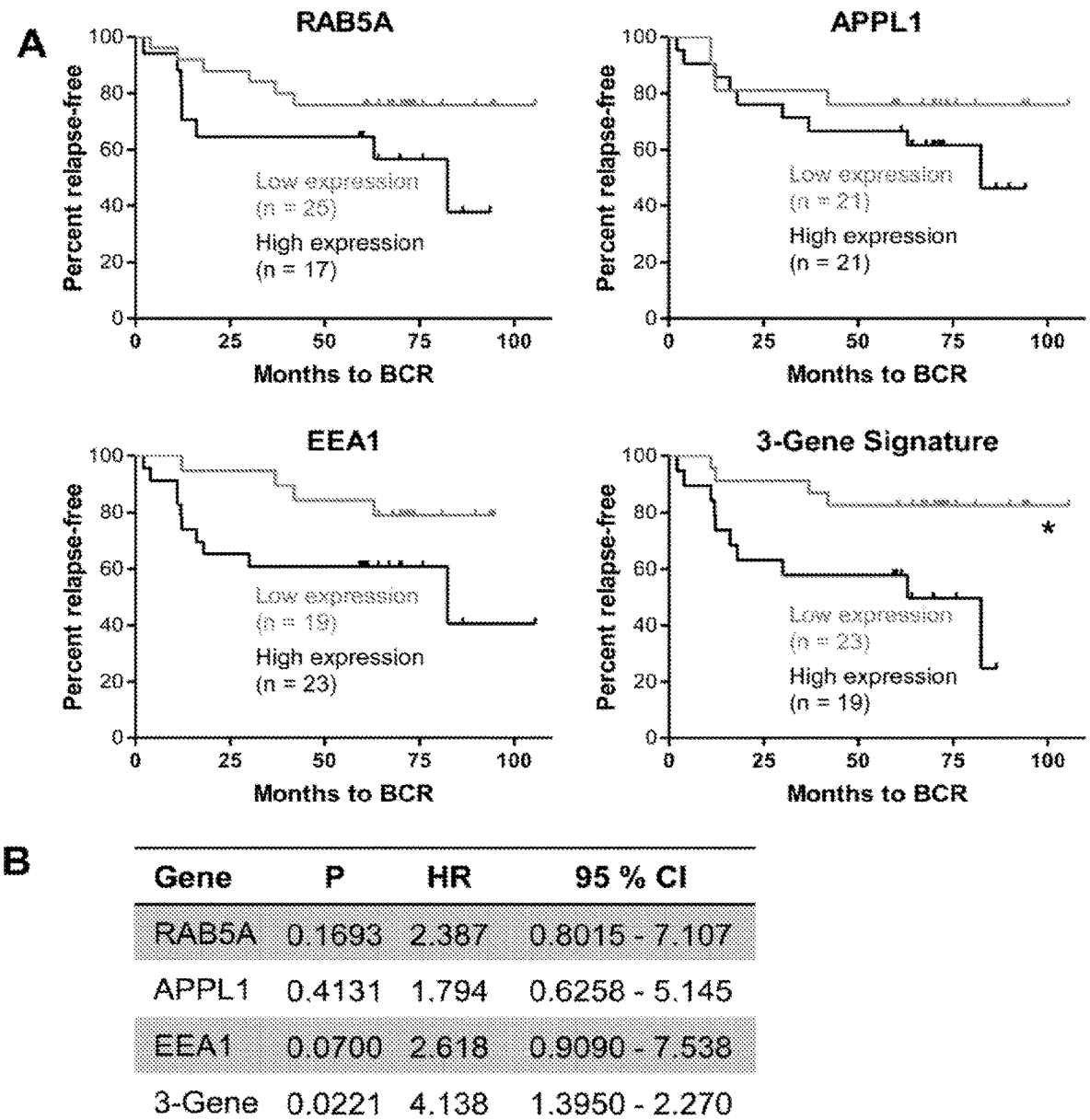
FIG. 21 shows the combined gene signature of RAB5A, APPL1 and EEA1 could stratify low PSA-expressing patients into prognostic subgroups based on BCR. (A) Patients from the Glinsky cohort expressing PSA ≤7.8 mg/mL were stratified into groups by K-means clustering based on RAB5A, APPL1 and EEA1 gene expression; the three-gene combined signature of RAB5A, APPL1 and EEA1 stratified patients based on BCR (P≤0.0221, Gehan-Breslow-Wilcoxon test; high expression—black line, low expression—grey line). (B) Multivariate analysis of gene expression in prostate cancer recurrence. BCR: biochemical recurrence; G-B-W: Gehan-Breslow-Wilcoxon test; HR: hazard ratio; CI: confidence interval.
Figure 22:
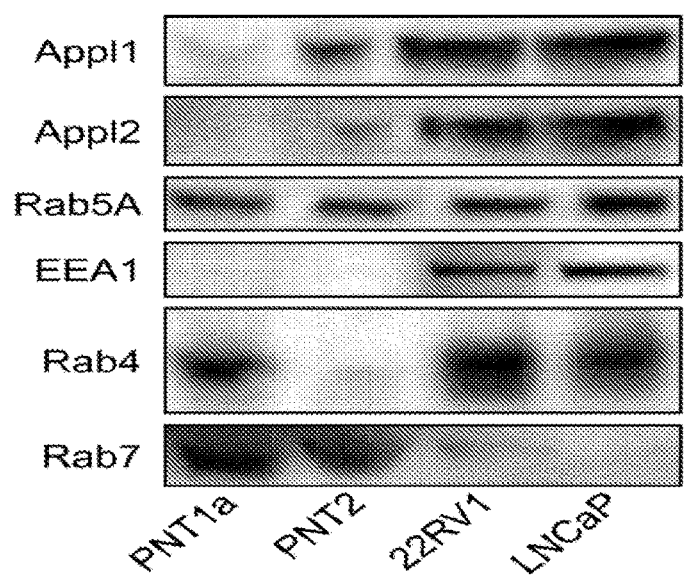
FIG. 22 shows detection and quantification of secreted endosome-related proteins from non-malignant control and prostate cancer cell lines. (A) Representative Western blots of protein secreted from non-malignant control cell lines PNT1a and PNT2, and prostate cancer cell lines 22RV1 and LNCaP. (B) The amount of each protein in non-malignant control cells (white bars) and prostate cancer cells (black bars) was quantified by densitometry from triplicate Western blots and significant differences denoted by an asterisk (* P≤0.05; ** p≤0.01).
Figure 22:
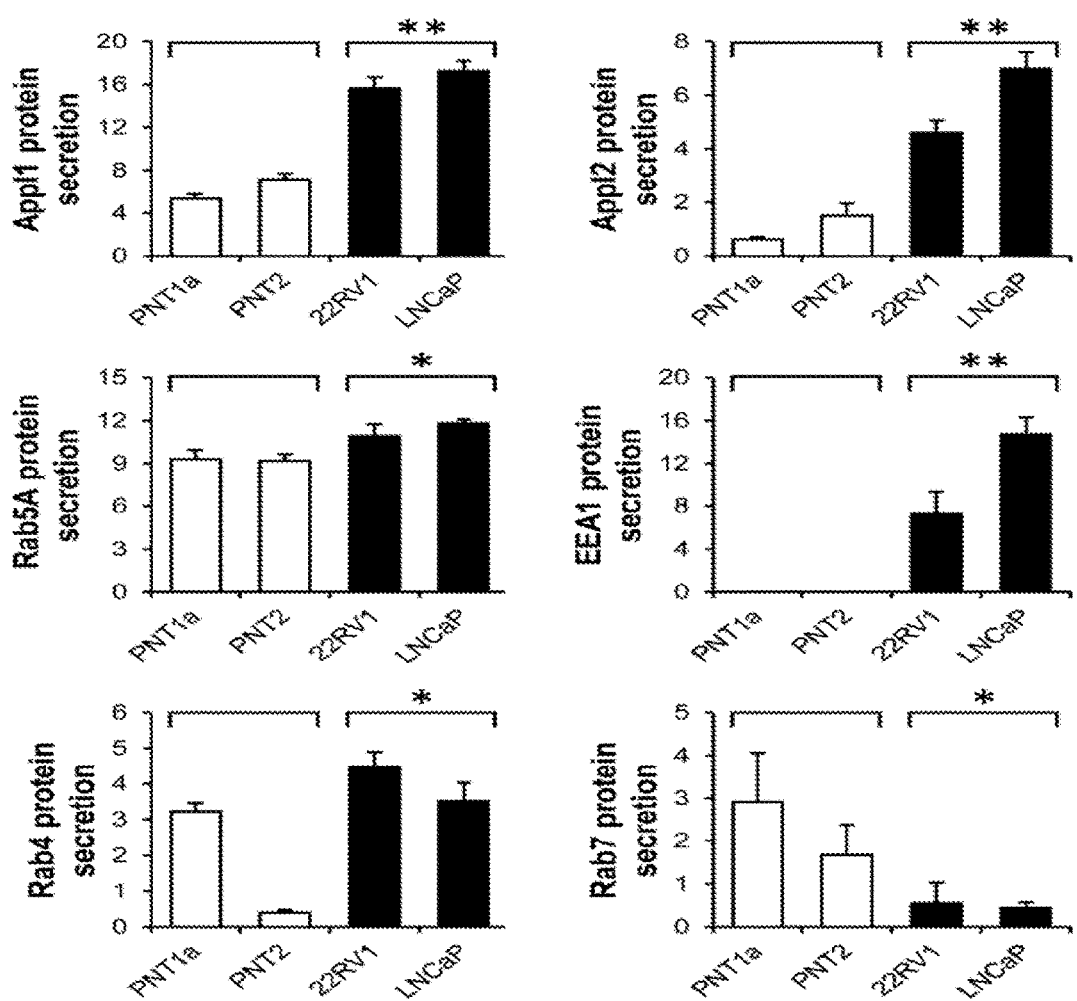

Individual RAB5A, APPL1 and EEA1 gene expression was not able to stratify patients into statistically significant risk groups (FIG. 21 A). However, stratification of patients based on expression of a three-gene signature using K means clustering methodology robustly separated patients into two groups with low or high expression of combined RAB5A, APPL1 and EEA1 (FIG. 21 A). Kaplan-Meier survival analysis indicated patients in the high expression group of the three-gene signature were at significantly higher risk of BCR when compared to those in the lower-expression group (HR 4.138, $P=0.0221$, 95% CI 1.3950-2.270; FIG. 21 B).

Discussion

Endosomal and lysosomal biogenesis is normally regulated by the transcription factor "EB" (TFEB), via control over the transcription factor of lysosomal genes containing "CLEAR elements". Target genes of TFEB include LIMP2 and LAMP1, which had differential expression in prostate cancer cell lines. Whilst we also observed elevated LIMP2 and reduced LAMP1 gene expression in prostate cancer tissue from these microarrays, there was no change in TFEB expression, suggesting that the normal action of TFEB may be altered in prostate cancer.

Altered gene expression during cancer development may be a valuable prognostic indicator. Increased expression of acid ceramidase (ASAH1) may be effective for the diagnosis of pre-cancerous PIN lesions and may be associated with improved prognosis following intervention.

Multivariate risk analysis and stratification of patients into low- and high-risk groups may provide a more individualised approach to prostate cancer detection and therapy, reducing over-diagnosis and over-treatment and thereby reducing patient morbidity and mortality. Active-surveillance is often used for patients deemed to have low-risk prostate cancer (e.g. clinical category T1c, Gleason score ≤6, and PSA ≤10 ng/mL), however older men are at an increased risk of mortality from prostate cancer despite these low scores and PSA serum levels. Examination of the survival curves of prostate cancer patients expressing low PSA, that represent a watchful-waiting group, reveals prostate cancers that are aggressive and result in more rapid recurrence, however additional factors such as Gleason score can improve patient stratification. Through quantitation of a gene signature of the three endosome genes, APPL1, EEA1 and Rab5A, in prostate cancer patients expressing PSA ≤7.8 ng/mL, led to patient stratification into high and low-risk recurrence groups. The capacity of these endosomal genes to stratify patients into prognostic risk groups suggested that they play an important role in the development and progression of prostate cancer and may therefore provide a new therapeutic target.

Example 4—Evaluation of Endosome Marker Secretion for the Detection of Prostate Cancer Results (i) Extracellular endosome proteins differentiate non-malignant and prostate cancer cell lines (FIG. 2). There was a significant increase in the amount of APPL1 and APPL2 detected in the culture media from prostate cancer compared to non-malignant control cell lines ($P \leq 0.01$). There was also a significant increase in the amount of Rab5A (approximately 20%; $P \leq 0.05$) detected in the culture media from prostate cancer cell lines when compared to non-malignant controls. EEA1 was detected in the culture media from LNCaP and 22RV1 prostate cancer cell lines, but was not detected in the culture media from the non-malignant control cell lines PNT1a or PNT2 ($P \leq 0.01$). There was a significant increase in the amount of Rab4 detected in the culture media from prostate cancer compared to non-malignant control cell lines ($P \leq 0.05$), although the amount detected in the latter, PNT1a and PNT2 cell lines, was variable. There was a significant reduction in the amount of Rab7 detected in the culture media from the prostate cancer compared to the non-malignant control cell lines ($P \leq 0.05$).

Discussion

Currently the prostate specific antigen (PSA) is used as a diagnostic marker, but this has reliability issues and still requires an invasive biopsy to further determine the expected course for the cancer development. There is therefore an urgent need for new biomarkers to enable accurate detection and prognosis of prostate cancer and to avoid unnecessary, invasive and costly procedures. We have observed significant increases in the amount of early endosome markers detected in the culture media from prostate cancer cell lines. In particular, the vesicular machinery associated with early endosomes, including APPL1, APPL2, Rab5A and EEA1 and recycling endosome protein Rab4, were markedly elevated in the culture media from prostate cancer cell lines, whilst the late endosome protein Rab7 showed a significant reduction in prostate cancer cells, when compared to non-malignant controls.

The secretion of early endosome markers APPL1, APPL2 and EEA1, but not late endosome marker Rab7 from prostate cancer cell lines implied that the maturation of endosome compartments into multivesicular bodies and exosome vesicles is altered in prostate cancer and may therefore be used to distinguish prostate cancer from non-malignant tissue.

A possible mechanism by which exosome formation may be disturbed in prostate cancer involves the vesicular GTPase Rab5. The over-expression of Rab5 allows simultaneous exposure of PI3P and APPL binding domains on the Rab5 protein, which would effectively reduce APPL1 dissociation and enable concurrent binding of EEA1. This could therefore result in endosomes that are Rab5-, EEA1- and APPL1-positive. Initiation of endosome membrane collapse and invagination to form exosomes is initiated by PI3P and the recruitment of Hrs and ESCRT complexes. The unusual composition of endosome vesicular machinery on prostate cancer endosomes may predispose exosome formation in early endosomes. The release of these exosomes from early endosomes would then account for the apparent secretion of early endosome vesicular machinery observed from the prostate cancer cell lines. This Rab5, EEA1 and APPL1 secretion may provide the basis of an assay to enable the detection of prostate cancer.

Blood and urine are ideal patient samples for the detection of vesicular machinery secreted in exosomes, as they represent potential analytes for a non-invasive diagnostic assay.

The altered secretion of early endosome and late endosome markers observed when comparing non-malignant control and prostate cancer cell lines provides a new avenue for investigation of diagnostic and prognostic markers that may lead to more accurate detection and prognosis of prostate cancer. The data here supports the notion that endosome biology is disturbed in prostate cancer, resulting in increased secretion of early-endosome markers and reduced secretion of late endosome markers from prostate cancer cell lines. Taken together, these results suggest that alterations in the secretion of early versus late endosome markers may provide the discrimination required for the early detection of prostate cancer.

Example 5—General Materials and Methods

Materials

Antibodies and Fluorescent Probes

Table 1 below details the properties of fluorescent-conjugate antibodies used in confocal microscopy analysis. Where dual labelling is performed using two primary antibodies of the same host-species, Zenon® IgG labelling kits (Life Technologies Australia Pty Ltd., Victoria, Australia) were used to label the primary antibodies directly, with the labelling protocol carried out as per manufacturers' instructions. Specific concentrations of primary antibodies and secondary conjugates used for Western blotting and immune fluorescence are detailed in the Tables below.

TABLE 1

Fluorescent probes used in laser-scanning confocal microscopy

| Fluorophore | Excitation maxima ($\lambda$) | Emission maxima ($\lambda$) | Detection spectrum (nm) |
|---|---|---|---|
| DAPI | 358 | 461 | 407-471 |
| Phalloidin Alexa Fluor® 488 | 495 | 518 | 500-560 |
| Alexa Fluor® 488 | 495 | 519 | 500-550 |
| Zenon® 488 | 495 | 519 | 500-550 |
| LysoTracker® Green DND-26 | 504 | 511 | 505-560 |

TABLE 1-continued

Fluorescent probes used in laser-scanning confocal microscopy

| Fluorophore | Excitation maxima (λ) | Emission maxima (λ) | Detection spectrum (nm) |
|---|---|---|---|
| LysoTracker ® Red DND-99 | 577 | 590 | 590-700 |
| Zenon ® 568 | 578 | 603 | 570-630 |
| Cy3 | 550 | 570 | 570-630 |
| Alexa Fluor ® 633 | 632 | 647 | 650-730 |
| Transferrin Alexa Fluor ® 633 | 632 | 647 | 650-730 |

TABLE 2

Primary and secondary antibodies used in Western blot analysis

| Antibody | Working concentration | Source cat# |
|---|---|---|
| M- Cathepsin B | 0.25 µg/mL | ab58802 |
| M- Cathepsin D | 5 µg/mL | ab6313 |
| Rb- Acid ceramidase | 1 µg/mL | ab74469 |
| Sh- α-Glucosidase | 1 µg/mL | In-house |
| Sh- β-Glucosidase | 1 µg/mL | In-house |
| Sh- α-Galactosidase A | 1 µg/mL | In-house |
| M- Prostatic acid phosphatase | 1 µg/mL | ab75704 |
| Rb- KLK2 | 1 µg/mL | ab40948 |
| Rb- KLK3 | 1 µg/mL | ab40949 |
| Rb- KLK4 | 1 µg/mL | ab40950 |
| Rb- KLK15 | 1 µg/mL | ab40961 |
| M- TFEB | 1 µg/mL | ab56330 |
| Rb- TfR1 | 1 µg/mL | ab108985 |
| Rb- TfR2 | 1 µg/mL | ab80194 |
| Sh- LIMP2 | 5 µg/mL | In-house |
| Rb- APPL1 | 0.4 µg/mL | ab95195 |
| Rb- APPL2 | 0.4 µg/mL | ab95196 |
| G- RAB5A | 1 µg/mL | R9704 |
| G- EEA1 | 1 µg/mL | sc-6415 |
| Rb- RAB4 | 1 µg/mL | ab13252 |
| G- RAB7A | 1 µg/mL | Sc-6563 |
| M- LAMP1 BB6 | 1 µg/mL | In-house |
| Rb- AKT | 2 µg/mL | In-house |
| Rb- AKT-P | 2 µg/mL | In-house |
| M- GAPDH HRP | 1/20000 | G9295 |
| G- α-Rabbit HRP | 1/2000 | A6154 |
| G- α-Mouse HRP | 1/2000 | A4416 |
| D- α-Sheep/Goat HRP | 1/2000 | AB324P |

TABLE 3

Primary antibodies and fluorophores used in immune fluorescence assays

| Antibody | Working concentration | Source cat# |
|---|---|---|
| Rb- TfR1 | 5 µg/mL | ab108985 |
| Rb- TfR2 | 5 µg/mL | ab80194 |
| Sh- LIMP2 | 10 µg/mL | in-house |
| Rb- APPL1 | 2 µg/mL | ab95195 |
| G- RAB5A | 4 µg/mL | R9704 |
| G- EEA1 | 4 µg/mL | sc-6415 |
| Rb- RAB4 | 4 µg/mL | ab13252 |
| G- RAB7A | 4 µg/mL | Sc-6563 |
| M- LAMP1 BB6 | 5 µg/mL | In-house |
| Rb- TGN46 | 10 µg/mL | ab50595 |
| LysoTracker ® 488 | 5 µM (1/200) | L7535 |
| Transferrin 633 | 5 µg/mL | T23362 |
| Phalloidin 488 | 1/100 | A12379 |
| D- α-Mouse Alexa fluor ® 488 | 1/250 | A11055 |
| D- α-Sheep Alexa fluor ® 488 | 1/250 | A11015 |
| D- α-Goat Cy3 | 1/750 | AP180C |

Cell Culture and Extract Preparation

Cell Lines

The cell lines PNT1a and PNT2, 22RV1 and LNCaP clone FCG were obtained from the European Collection of Cell Cultures via CellBank Australia (Children's Medical Research Institute, New South Wales, Australia). Cell lines RWPE 1, CaHPV10 and DU 145, were obtained from the American Tissue Culture Collection via Cryosite (Cryosite Ltd., New South Wales, Australia). These cell lines are absent from the List of Cross-Contaminated or Misidentified Cell Lines, version 6.8 (9 Mar. 2012).

Any study of prostate cancer should equally be studied on normal non-cancerous prostate. Analysing cell lines derived from primary or metastatic prostate cancer results in a need for cell lines derived from healthy prostate tissue. This presents a problem for cell culture regarding the normal division and replication cycle of a healthy cell. Unlike the majority of cancer cell lines, which will multiply at a regular rate, to generate a non-carcinoma cell line, a healthy cell must be developed to invoke a constant cell cycle and rate of division.

As such, the cell lines RWPE 1, PNT1a and PNT2 used in this study to represent normal epithelial-cell phenotypes, have been adapted and immortalised with viruses. Specifically, human papilloma virus-18 (HPV 18) was used to immortalise the RWPE 1 cell line, and Simian vacuolating virus 40 (SV40) to immortalise PNT1a and PNT2 cell lines. The cancer cell line CaHPV10 was derived from a primary adenocarcinoma of the prostate immortalised with HPV 18. This cell line is not androgen responsive.

The 22RV1 cancer cell line was derived from a xenograft that had been serially propagated in mice after castration-induced regression and relapse of a parental, androgen-dependent xenograft. The cell line expresses androgen receptor however its proliferation is unresponsive to androgen stimulation.

The cancer cell line LNCaP was previously derived from a lymph node metastasis of prostate adenocarcinoma. The LNCaP cell line is androgen responsive.

Cancer cell line DU 145 was previously derived from a moderately-differentiated brain metastasis of prostate adenocarcinoma. They are epithelial cells, and unresponsive to androgen stimulation.

Culture Conditions

PNT1a, PNT2 and 22RV1 cell lines were maintained in Roswell Park Memorial Institute (RPMI) 1640 media (Gibco®, Life Technologies), supplemented with 10% foetal calf se-rum (FCS) (In Vitro Technologies Pty Ltd., Victoria, Australia) and 2 mM L-glutamine (Sigma Aldrich Pty Ltd., New South Wales, Australia). RWPE 1 and CaHPV10 cell lines were maintained in Keratinocyte Serum-Free Media containing L-glutamine (K-SFM) (Gibco®), supplemented with the supplied human recombinant Epidermal Growth Factor 1 53 (EGF 1 53) and Bovine Pituitary Extract (BPE). The DU 145 cell line was maintained in Minimum Essential Medium (MEM) (Gibco®) and supplemented with 2 mM L-glutamine and 10% FCS. Cancer cell line LNCaP was maintained in RPMI 1640 media supplemented with 2 mM L-glutamine, 10% FCS, 10 mM HEPES (Life Technologies) and 1 mM sodium pyruvate (Sigma Aldrich). Cells were incubated in a humidified incubator at 37° C. with 5% $CO_2$ in a Sanyo MCO-17AI $CO_2$ Incubator (Sanyo Electric Biomedical Co., Ltd., Osaka, Japan).

Cells were passaged at approximately 90% confluence, washed with sterile dPBS (Sigma Aldrich) and trypsinised using 1× Trypsin-EDTA solution containing 0.12% trypsin, 0.02% EDTA (SAFC®, Sigma Aldrich) until dissociated from the culture flask surface. Trypsin was neutralised with growth media containing 10% RWPE 1 and CaHPV10 cell lines cultured in serum-free media were pelleted at 250 g for five minutes and washed with dPBS to remove foetal calf serum. Cells were passaged at a 1:10 to 1:20 ratio for general maintenance.

For long-term storage, cell lines were stored in liquid nitrogen. For cryopreservation, cell cultures were passaged as normal. After trypsin inactivation using 10% FCS, cells were pelleted by centrifugation at 250 g for five minutes and resuspended in their respective culture media containing 10% FCS and 10% DMSO (Sigma Aldrich). 1 mL aliquots of cell suspension were stored at −80° C. overnight in an isopropanol freezing container (Nalgene, Thermo Fisher Scientific Australia Pty Ltd., Victoria, Australia) prior to long-term storage in liquid nitrogen.

Sample Preparation
Cell Extract Preparation for Immune Blotting

Cell lines were seeded in T75 flasks and incubated at 37° C. and 5% CO2. At a confluence of 80-90%, culture media was aspirated, cells washed once with dPBS, and cells incubated for 48 hours with serum-free media.

Total cell protein was extracted using a TNS buffer containing 20 mM Tris (pH 7.0), 500 mM sodium chloride and 2% SDS solution, diluted in Milli-Q H2O. A solution containing Tris and sodium chloride was prepared to 80% of the final volume, with the remaining 20% volume comprising 10% SDS, added within 30 minutes prior to use. Following 48 hours of incubation, cell culture media was aspirated and cells washed twice with room-temperature dPBS. 800 μL of TNS buffer was added to the culture flask and rotated to cover cell-layer in its entirety. Cells were harvested by using a rubber cell scraper, and the resulting extract transferred to a 1.5 mL tube. Extract was immediately heated to 65° C. for five minutes and sonicated at high-frequency for one minute.

To obtain a more homogenous lysate, cell material was passed through a 25-gauge (0.65 mm) syringe needle, a total of 6 times. Additional TNS buffer was added, where required, to produce a less viscous lysate. Samples were stored at −20° C.

Total protein was quantified using a bicinchoninic acid assay (Micro BCA kit, Pierce, Thermo Scientific Pty Ltd., Rockford, IL, USA) according to the manufacturer's instructions. Samples were quantified using a Wallac Victor™ optical plate-reader and Workout software v2.0 (Perkin-Elmer Pty Ltd., Victoria, Australia) using a 5-point parameter standard-fit curve.

Conditioned media collected at time of cell harvesting and previously stored at −80° C. was thawed, and 33 mL aliquots centrifuged at 1000 g for 10 minutes at 4° C. to remove any cell debris. 30 mL of supernatant was transferred to a 50 mL conical tube and sodium deoxycholate (DOC) (Sigma Aldrich) added to a final 0.02% v/v concentration. Following a brief vortex, the samples were kept on ice for 30 minutes.

A 100% w/v solution of trichloroacetic acid (TCA) (Sigma Aldrich) was added to a final concentration of 15% v/v, agitated by vortex for 30 seconds, and incubated on ice for two hours to precipitate protein from the culture media. Precipitated protein was collected by centrifugation of samples at 5,500 g for 30 minutes, with supernatant containing TCA and contaminant waste aspirated. The protein pellet was washed with 4 mL ice-cold (−20° C.) acetone by vortex and incubated at room temperature for five minutes. The sample underwent a further centrifugation at 5,500 g for 30 minutes and the acetone wash repeated. After a final centrifuge step, the supernatant was aspirated, and conical tube containing protein pellet was dried under a slow stream of nitrogen gas. Each protein pellet, produced from 30 mL media, was resuspended in a 135 μL 1×SDS-sample buffer/PBS solution, and stored at −20° C. for use at a later time in Western blot assays.

Cell Extract Preparation for Quantitative Analysis of Gene Expression

Cell lines were cultured in triplicate in 75 $cm^2$ flasks as described for Western blotting, with serum deprivation for 48 hours. Media was aspirated and flasks washed with dPBS. 1 mL TRI Reagent® (Applied Biosystems Pty Ltd., Victoria, Australia) was added to each T75 flask and scraped using a rubber cell-scraper and transferred to a 1.5 mL flip-top tube. Samples were stored at −80° C. until further required.

Cell Culture Preparation for Immune Fluorescence Analysis by Confocal Microscopy Cell cultures were passaged as normal, seeded at low density on 22 mm, "Number 1", glass coverslips (Menzel-Glaser, Thermo Fisher Scientific Australia Pty Ltd., Victoria, Australia) and incubated in culture media for 48 hours at 37° C. and atmosphere of 5% $CO_2$. After 48 hours, culture media was aspirated and cells fixed using 4% formaldehyde (v/v) PBS solution for 20 minutes at room temperature. Fixed cells were further permeabilised with 0.1% Triton-X (v/v) in PBS for 10 minutes.

Quantitative Analysis of Protein Expression
SDS-PAGE and Transfer

10 μg of total protein from cell lysates were heat-denatured for five minutes at 100° C. in sample buffer (Nu-PAGE® LDS Sample Buffer (4×), Life Technologies) and reducing agent containing 50 mM dithiothreitol (NuPAGE® Sample Reducing Agent (10×)). Prepared samples were separated using a 10% 15-well, or 12% 17-well SDS-PAGE pre-cast gel in an XCell SureLock™ Mini-Cell electrophoresis system, buffered with SDS-PAGE running-buffer (Life Technologies) at 120 V (fixed, with variable current), for 1.5 hours. Following electrophoresis, separated protein was transferred to polyvinylidene difluoride (PVDF) membranes (Polyscreen®, Perkin-Elmer) at 35 V for one hour.

Immunoblotting and Detection

Membranes were blocked for 1 hour at room temperature using 5% w/v skim-milk solution in TBS-tween (0.1%) and incubated with the appropriate antibody (Table 2.2) diluted in 5% skim-milk overnight at 4° C. with gentle agitation. Following incubation with the primary antibody, membranes were washed thrice with TBS-tween for five minutes at room temperature. A horseradish-peroxidase conjugate secondary antibody (Table 2.2), diluted to 1/2000 in 5% skim-milk solution, was incubated with the PVDF membrane for one hour at room temperature with gentle agitation.

Membranes were washed three times with TBS-tween for five minutes, followed by antibody detection using electro chemiluminescence (ECL). Membranes were incubated for one minute in the dark using Novex® ECL chemiluminescent substrate reagent kit (Life Technologies), and visualised using an ImageQuant™ LAS 4000 imager, software version 1.2.0.101 (GE Healthcare Bio-Sciences Pty Ltd., New South Wales, Australia). GAPDH loading control was detected using a goat a GAPDH HRP conjugate (Sigma Aldrich) at a 1:20,000 dilution in 5% skim-milk. Detection of GAPDH was performed concurrently, where molecular weights would allow for detection, with secondary-HRP detection of primary antibody, at room temperature for one hour. Where molecular weights of GAPDH and marker protein would potentially conflict, PVDF membranes were stripped of primary antibody and re-probed with a GAPDH HRP conjugate.

Blots were performed in triplicate and images quantified using AlphaViewSA™ software v3.0.0.0 (ProteinSimple, Santa Clara, California). Lane-analysis was performed using the software to determine molecular weights of detected protein. The amount of protein was quantified based on signal density and size of band and normalised to GAPDH signal that was derived from band analysis. Clustered linear regression or Kruskal-Wallis rank sum statistical methods were used depending on sample and group sizes to determine significance of detected protein amounts between control and cancer cell lines. Tests were performed using Stata/SE v11.2 (StataCorp LP, Texas, U.S.A). Significant results were greater than 95% confidence ($P \leq 0.05$).

Membrane Stripping

Proceeding primary antibody detection, PVDF membranes were stripped and probed for GAPDH, used as a loading control for total protein amount. PVDF membranes were washed twice in a stripping buffer containing 0.02 M Tris, 0.5 M NaCl, 2% SDS and 100 mM mercaptoethanol in Milli-Q H2O. Membranes were agitated vigorously with the buffer at 55° C. for 30 minutes and further washed with vigorous agitation three times with TBS-tween for 15, 20 and 30 minutes at room temperature. The PVDF membranes were blocked with 5% skim-milk in TBS-tween for 1 hour at room temperature and detection of GAPDH performed using 1:20,000 dilution of HRP-conjugated a GAPDH antibody.

Quantitative Analysis of Gene Expression

RNA Extraction

Cells frozen with TRI Reagent® were thawed and incubated at room temperature for five minutes. 200 µL chloroform was added to each millilitre of TRI Reagent® used in cell harvesting. Samples were shaken vigorously for one minute, and stood at room temperature for three minutes. Samples were then centrifuged for 15 minutes at 16,000 g, at 4° C.

RNA extraction was performed using an RNeasy® mini kit (Qiagen Pty Ltd., Victoria, Australia) following manufacturer's instructions. The upper aqueous phase was transferred to a fresh tube and mixed in an equal volume with 70% ethanol, diluted in RNase-free $H_2O$. 700 of sample was transferred to an RNeasy® purification column (Qiagen) and centrifuged for 20 seconds at 16,000 g. After centrifugation, flow-through was discarded and the remaining sample/ethanol mix loaded onto the column and centrifuged at 16,000 g for 20 seconds. 350 RW1 buffer was pipetted onto the spin-column membrane and column centrifuged for 15 seconds at 16,000 g.

Samples were treated with DNAse I to remove genomic DNA following manufacturer's instructions (Life Sciences Pty Ltd., Victoria, Australia). DNAse I stock solution was diluted 1:7 with buffer RDD of which 80 µL DNAse I solution was then directly applied to the spin-column membrane and incubated for 15 minutes at room temperature.

A further 350 µL buffer RW1 was added onto the column and centrifuged for 15 seconds at 16,000 g followed by two washes using 500 µL RPE buffer. To remove any remaining buffer, the column was centrifuged for 2 minutes at 16,000 g followed by a further one minute at 16,000 g. Elution of each sample was achieved by application of 50 µL of RNase-free $H_2O$ directly to the spin-column membrane, followed by centrifugation for one minute at 16,000 g. Eluted RNA samples were stored at −80° C.

The concentration of extracted RNA was determined using a NanoDrop™ 2000 spectrophotometer (Thermo Fisher Scientific Australia Pty Ltd., Victoria, Australia) at 260 nm. 260/280 nm and 260/230 nm ratios were assessed to ensure samples were free from protein and DNA contamination, where a ratio greater than 1.6 indicates a sample free of contamination.

cDNA Synthesis

Complementary DNA (cDNA) for use in qRT-PCR was prepared using the High Capacity RNA-to-cDNA Kit (Life Technologies) following manufacturer's instructions. For a 20 reaction containing 2 µg of RNA, 10 µL master-mix buffer and 1 µL of reverse transcriptase enzyme were added, with the volume made to 20 µL with RNase-free $H_2O$. Amplification was performed using a DNA Engine® Peltier Thermal Cycler (Bio-Rad Laboratories Pty, Ltd., New South Wales, Australia), with incubation of reaction mixes for one hour at 37° C. followed by 95° C. for five minutes and then chilled to 4° C. cDNA samples were stored at −20° C. until required.

Primer Design

Primer sequences, detailed in Table 2.4 below, were obtained from either published literature, Harvard PrimerBank, or designed using NCBI Primer BLAST. Primers selected from the Harvard PrimerBank were chosen based on criteria of the final amplicon size being less than 150 base-pairs, that their melting temperature be near 60° C. and that, where possible, they extended across an exon-exon junction. Primers designed using Primer-BLAST also had these criteria. Oligonucleotides were purchased from GeneWorks Pty Ltd, South Australia.

Quantitative RT-PCR

10 µL reaction mixtures were set up containing 5 µL Power SYBR® Green PCR Master Mix (Life Technologies), 0.5 µL each of 10 nM forward and reverse primer, 2 µL cDNA sample diluted to 1:25 with DEPC-treated H2O, and made up to 10 µL with 2 µL DEPC-treated H2O. Reactions were plated onto 96-well plates (Life Technologies) in triplicate, with each plate containing serial dilutions of a reference cDNA sample (from the LNCaP cell line) for target gene and endogenous gene standard curves, to control for reaction efficiency.

qPCR was performed using a 7500 Fast Real-Time PCR System (Life Technologies) using ABI 7500 software v2.0.2.

Cycling conditions for all targets comprised; 50° C. for 2 minutes, 95° C. for 10 minutes to activate enzyme and denature cDNA, followed by 40 cycles of a 95° C. 15-second denaturation step and a 60° C. 60-second extension and signal acquisition step. Melt curves were produced following each run to confirm absence of primer-dimers or product and other contaminants.

Cycle threshold (CT) values were derived at a threshold level of 0.35, in the exponential phase of amplification and above baseline noise. The relative amount of gene expression from each sample was derived by calculation of CT values vs. standard curves produced from serially diluted standard material. Reaction efficiencies, calculated from the slope of a linear trend line plotted from diluted standards, were between 90 and 110%. Each target was assessed in triplicate on a single plate, with triplicate biological replicates run independently. Mean gene expression was derived from the mRNA amount on each replicate plate, with each single plate providing a mean CT and mRNA level from replicate wells.

TABLE 5

Primer sequences used in qPCR

| Gene | | Sequence (5'-3') | GeneBank ID (NM_) | Primer position | Source |
|---|---|---|---|---|---|
| GAPDH | F | TGCACCACCAACTGCTTAGC (SEQ ID NO. 14) | 002046.3 | 556-575 | {Sardiello, 2009} |
| | R | GGCATGGACTGTGGTCATGAG (SEQ ID NO. 15) | | 642-622 | |
| LAMP1 | F | ACGTTACAGCGTCCAGCTCAT (SEQ ID NO. 16) | 005561.3 | 608-628 | {Sardiello, 2009} |
| | R | TCTTTGGAGCTCGCATTGG (SEQ ID NO. 17) | | 685-667 | |
| SCARB2 (LIMP-2) | F | AAAGCAGCCAAGAGGTTCC (SEQ ID NO. 18) | 005506.3 | 1488-1506 | Primer-BLAST |
| | R | GTCTCCCGTTTCAACAAAGTC (SEQ ID NO. 19) | | 1556-1536 | |
| TFRC | F | GGCTACTTGGGCTATTGTAAAGG (SEQ ID NO. 20) | 003234.2 | 250-272 | PrimerBank |
| | R | CAGTTTCTCCGACAACTTTCTCT (SEQ ID NO. 21) | | 405-383 | |
| TFR2 | F | CGTGCGGAGACTCTGTGTT (SEQ ID NO. 22) | 003227.3 | 329-347 | PrimerBank |
| | R | ATCCAGGTCAGGCTCATAGTT (SEQ ID NO. 23) | | 387-367 | |
| APPL1 | F | ACTTGGGTACATGCAAGCTCA (SEQ ID NO. 24) | 012096.2 | 747-767 | PrimerBank |
| | R | TCCCTGCGAACATTCTGAACG (SEQ ID NO. 25) | | 863-843 | |
| APPL2 | F | AGCTGATCGCGCCTGGAACG (SEQ ID NO. 26) | 018171.3 | 1543-1562 | Primer-BLAST |
| | R | GGGTTGGTACGCCTGCTCCCT (SEQ ID NO. 27) | | 1636-1616 | |
| EEA1 | F | CCCAACTTGCTACTGAAATTGC (SEQ ID NO. 28) | 003566.3 | 497-518 | PrimerBank |
| | R | TGTCAGACGTGTCACTTTTTGT (SEQ ID NO. 29) | | 591-570 | |
| RAB5A | F | AGACCCAACGGGCCAAATAC (SEQ ID NO. 30) | 004162.4 | 22-41 | PrimerBank |
| | R | GCCCCAATGGTACTCTCTTGAA (SEQ ID NO. 31) | | 164-143 | |
| RABEP1 (Rabaptin5) | F | ATTAAGGCGATTGCCACAGTC (SEQ ID NO. 32) | 004703.4 | 486-506 | PrimerBank |
| | R | TGGTGCTCATAGTCACGAACT (SEQ ID NO. 33) | | 616-596 | |
| RAB4A | F | GGGGCTCTCCTCGTCTATGAT (SEQ ID NO. 34) | 004578.2 | 470-490 | PrimerBank |
| | R | AGCGCATTGTAGGTTTCTCGG (SEQ ID NO. 35) | | 519-499 | |
| RAB11 | F | CAACAAGAAGCATCCAGGTTGA (SEQ ID NO. 36) | 004663.4 | 146-167 | PrimerBank |
| | R | GCACCTACAGCTCCACGATAAT (SEQ ID NO. 37) | | 260-239 | |
| RAB25 | F | TCGGCGAATCAGGTGTGGGGA (SEQ ID NO. 38) | 020387.2 | 279-299 | Primer-BLAST |
| | R | ATGGTGGTGCGGCTGTCGTG (SEQ ID NO. 39) | | 360-341 | |
| RAB7A | F | GTGTTGCTGAAGGTTATCATCCT (SEQ ID NO. 40) | 004637.5 | 19-41 | PrimerBank |
| | R | GCTCCTATTGTGGCTTTGTACTG (SEQ ID NO. 41) | | 128-106 | |

TABLE 5-continued

Primer sequences used in qPCR

| Gene | | Sequence (5'-3') | GeneBank ID (NM_) | Primer position | Source |
|---|---|---|---|---|---|
| RAB9 | F | CCTCATTGCGCCCAGACGGG (SEQ ID NO. 42) | 004251.4 | 108-127 | Primer-BLAST |
| | R | AGTGCAAGAGTGTCTCGCGGC (SEQ ID NO. 43) | | 181-161 | |

Confocal Microscopy

Immune Fluorescence Labelling

Non-specific antibody reactivity was reduced via incubation of fixed cells in a 5% (w/v) bovine serum albumin (BSA) PBS solution for two hours at room temperature with slow agitation. Cells were then incubated with the appropriate concentration of primary antibody (Table 2.3) diluted in 5% BSA for two hours at room temperature followed by secondary antibody incubation for one hour at room temperature. Unbound antibody was removed by three PBS washes and coverslips mounted on 1 mm microscope slides with ProLong® Gold Antifade Reagent containing DAPI nuclear stain (Life Technologies).

Image Acquisition and Processing

Confocal microscopy was performed using a Zeiss LSM 710 META NLO laser scanning microscope (University of South Australia, Australia) and associated Carl Zeiss Zen 2009 software. Laser lines of 370, 488, 543 and 633 nm were utilised for DAPI, Alexa Fluor® 488, Cy3 and Alexa Fluor® 633 fluorescence. Laser intensities were set between 5% and 25% depending on fluorescent target. To eliminate signal cross over between fluorophores, emission fluorescence was filtered with a 20 nm gap between each channel. Each channel was captured by between frame sequential scanning with a 4-line average with a pixel-dwell of 3.15 µs. Pinhole diameters for each laser were set to 1 Airy unit. Cells were observed under a 1.4-aperture 63× oil-immersion objective lens, with 2× optical zoom applied. Images were captured at a resolution of 1024 px2 with a 16 bit greyscale depth. Based on image capture resolution of 1024 pixels and lens and zoom factor, each pixel is equivalent to 0.066 µM in dimension. At least four cells were randomly selected on each coverslip, and a representative image processed for creation of figures. Images were exported as grayscale 16 bit TIFF files, and further processing performed using Adobe® Photoshop® CS5 (Adobe Systems Inc., San Jose, California, U.S.A).

Visualisation of Intracellular Trafficking and Endocytosis

LysoTracker® positive vesicles were visualised by live cell confocal microscopy to prevent leakage of LysoTracker® that can occur in fixed cells. Cells were cultured in standard conditions in DKSH hydrophobic chamber slides (DKSH Australia Pty Ltd., Victoria, Australia). Subsequently, LysoTracker® was diluted 1/200 in culture media and added to cells. At five minutes of incubation at 37° C., cell cultures were visualised.

Transferrin endocytosis assays was performed on cells cultured in normal conditions detailed herein. At 48 hours, culture media was replaced with fresh media containing a 1/1000 dilution of transferrin-633 conjugate. Cells were incubated for a period of 5, 15 or 30 minutes, following which the media was aspirated, cells washed briefly in dPBS, and fixed with 4% PFA. Fixed cells were blocked for two hours with 5% BSA before a 90 minute incubation with phalloidin-488 conjugate. Unbound antibody was removed by three PBS washes and coverslips mounted on 1 mm microscope slides with ProLong® Gold Antifade Reagent containing DAPI nuclear stain (Life Technologies).

Co-Fluorescence of Transferrin and Endosome Markers.

Cells were incubated in normal conditions as detailed herein. At 48 hours, culture media was replaced with fresh media containing a 1/1000 dilution of transferrin-633 conjugate. Cells were incubated with transferrin-633 media for a period of 20 minutes. Subsequently, media was aspirated, washed briefly with dPBS, fixed and permeabilised. Labelling with primary and secondary antibodies proceeded as detailed herein.

Public Prostate Cancer Cohorts

The Taylor cohort consisted of patients treated by radical prostatectomy at Memorial Sloan-Kettering Cancer Center (MSKCC), profiling 150 prostate cancer and 29 nonmalignant tissues was performed using Affymetrix Human Exon 1.0 ST arrays. Data was obtained from the cBio Cancer Genomics Pathway Portal. The Chandran cohort is composed of 18 normal tissues, 65 primary, 25 metastatic and 63 normal adjacent non-malignant tissues. Expression profiling of these tissues was carried out using Affymetrix U95Av2 human gene arrays. Data was retrieved from NCBI GEO (accession number GSE6919). A cohort by Tomlins was retrieved from NCBI GEO (accession number GSE6099) and is comprised of 32 primary, 20 metastatic, 13 prostatic intraepithelial neoplasia (PIN), and 27 normal tissue samples. Analysis of samples was previously performed using a Chinnaiyan Human 20K Hs6 array. An additional cohort from MSKCC, the Glinsky cohort was composed of 79 malignant prostate tissues with clinical follow-up data to 106 months that was used to assess for biochemical recurrence of prostate cancer (BCR). This comprised 29 patients with BCR as defined by a PSA level ≥0.2 ng/mL and 50 with no progression.

Statistical analysis between normal and prostate cancer tissue was performed using a two-tailed unpaired t test with Welch's correction. To evaluate differences in expression between multiple groups in the Chandran and Tomlins cohort, Kruskal-Wallis with Dunn's multiple comparison test was performed. Data from the Glinsky cohort was analysed using a two-tailed unpaired t test with Welch's correction to determine differences between Gleason grade 3 and 4 groups. K means clustering was implemented using Stata/SE v11.2 (Stata Corp LP, Texas, U.S.A) to determine high and low gene expression groups and evaluated using Kaplan-Meier survival curves with Gehan-Breslow-Wilcoxon test to determine difference between the curves. All statistical tests were performed using GraphPad Prism 5.03 (GraphPad Software Inc., California, U.S.A).

Example 6—Generation of Antibodies to APPL1 and RAB7

Epitopes with a length of 15 amino acids were selected from the protein sequence of human APPL1 or RAB7 that were predicted to have strong antigenic properties suitable for detection following synthesis of antibodies to these specific sequences:

```
APPL1:
Epitope #1 Position 145-159 (human):
                                (SEQ ID NO. 7)
NRYSRLSKKRENDKV.

Epitope #2 Position 265-279 (human):
                                (SEQ ID NO. 8)
DPDPTKFPVNRNLTR.

Epitope #3 Position 691-705 (human):
                                (SEQ ID NO. 9)
SQSEESDLGEGGKKR.

RAB7:
Epitope #1 Position 103-117 (human):
                                (SEQ ID NO. 10)
RDEFLIQASPRDPEN.

Epitope #2 Position 124-138 (human):
                                (SEQ ID NO. 11)
GNKIDLENRQVATKR.

Epitope #3 Position 183-197 (human):
                                (SEQ ID NO. 12)
YNEFPEPIKLDKNDR.
```

Peptides were synthesized and used to immunise rabbits to generate polyclonal antibodies.

Figure 23:
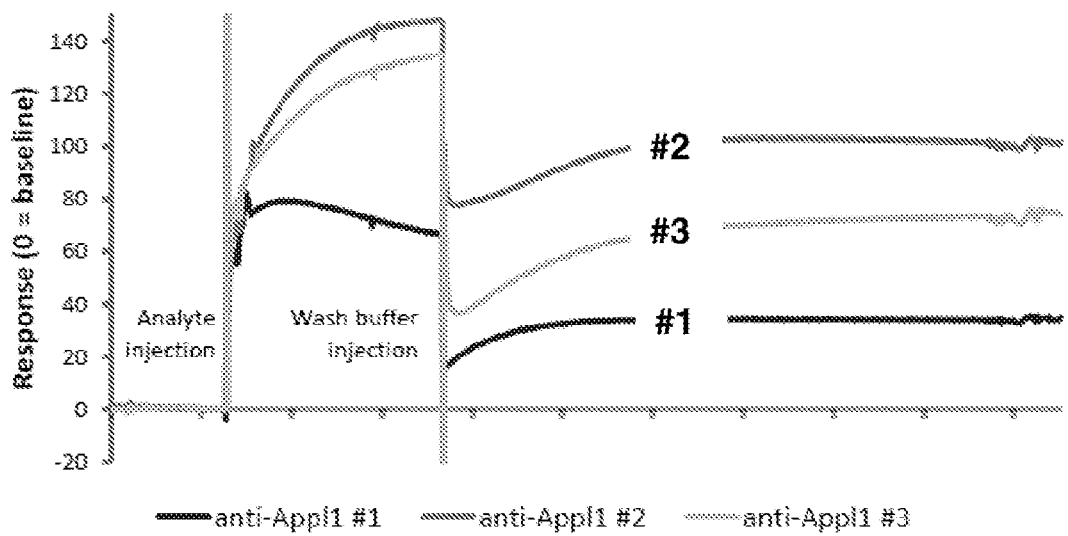
FIG. 23 shows rabbit anti-Appl1 polyclonal antibody affinities to Appl1 recombinant protein (Panel A) and rabbit anti-Rab7 polyclonal antibody affinities to Rab7 recombinant protein (Panel B).
Figure 23:
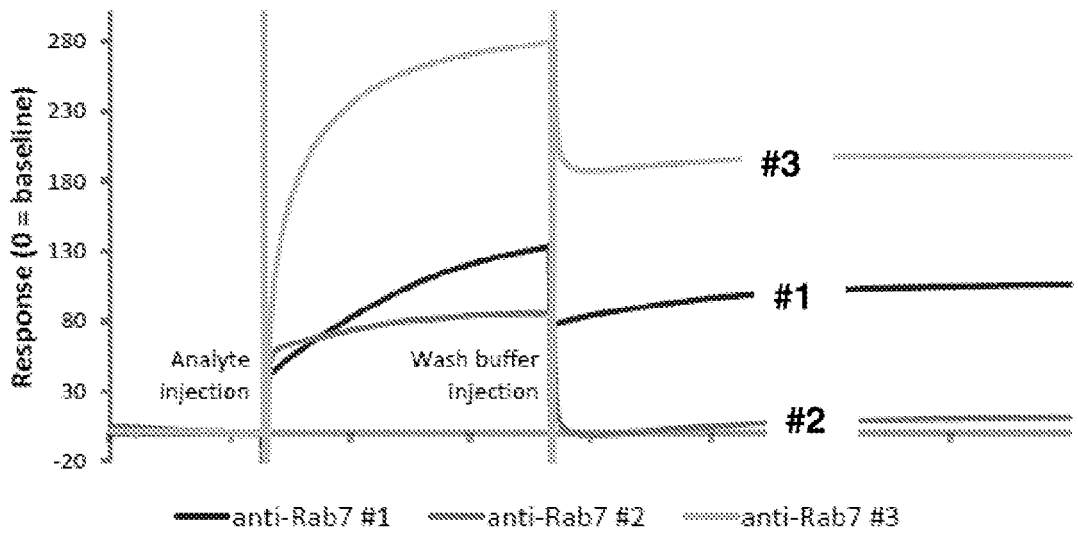

FIG. 23A shows rabbit anti-Appl1 polyclonal antibody affinities to Appl1 recombinant protein. FIG. 23B shows rabbit anti-Rab7 polyclonal antibody affinities to Rab7 recombinant protein. The affinity of the polyclonal antibodies produced to the peptides detailed above were measured using surface-plasmon resonance (BiaCore T100) to purified APPL1 or RAB7 protein. The results are shown in FIG. 23. The Affinity of Appl1 #2 (FIG. 23A) and Rab7 #3 (FIG. 23B) were highest, with greatest binding and affinity post-wash, suggesting that these would bind more of their respective protein in downstream assays and be suitable as a capture antibody for DELFIA and sandwich ELISAs. Appl1 #3 and Rab7 #1 showed good affinities to the purified protein and would be suitable for Europium-labelling to use in DELFIA assays for detection of their respective target proteins.

Figure 24:
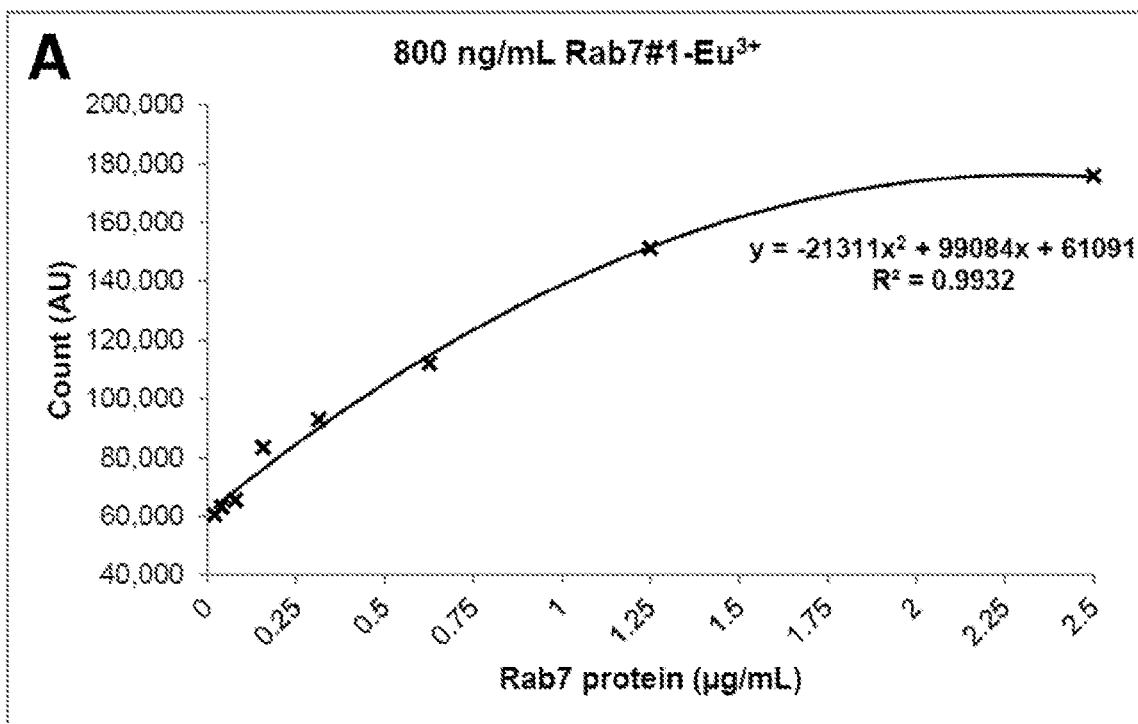
FIG. 24 shows in Panel A standard curve for europium-labelled rabbit anti-Rab7 polyclonal antibody (raised to epitope #1) and Panel B shows standard curve for europium-labelled rabbit anti-Appl1 polyclonal antibody (raised to epitope #3).
Figure 24:
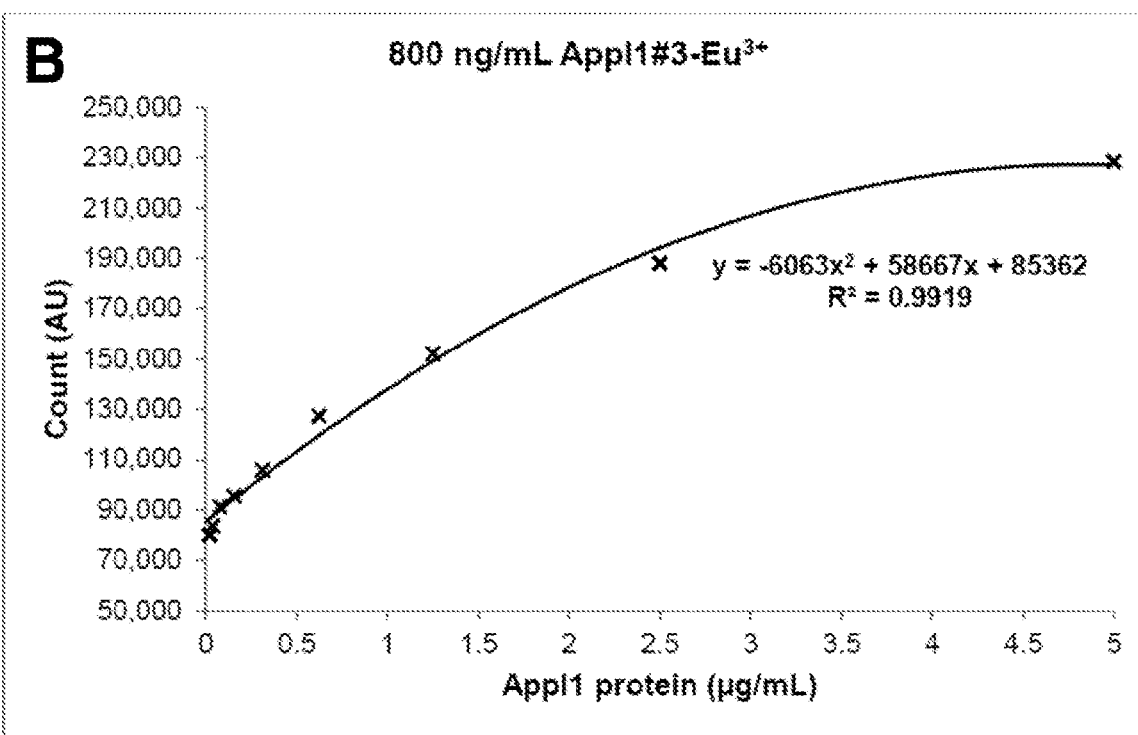

FIG. 24A shows a standard curve for europium-labelled rabbit anti-Rab7 polyclonal antibody (raised to epitope #1) for Rab7 protein in a direct DELFIA assay. 3.9 mL labelled antibody was previously obtained at 0.13 mg/mL (0.51 mg total Ab), with an approximate Europium-label yield of 1.6. FIG. 24B shows a standard curve for europium-labelled rabbit anti-Appl1 polyclonal antibody (raised to epitope #3) for Appl1 protein in a direct DELFIA assay. 4.8 mL labelled antibody was previously obtained at 0.11 mg/mL (0.53 mg total Ab), with an approximate Europium-label yield of 3.8.

Example 7—Diagnostic and Prognostic Value of Additional Markers (i) Altered Endosome-Related Gene Expression During Cancer Progression The expression of endosome-related mRNA transcripts was analysed from the Tomlins cohort enabling the analysis of prostatic intraepithelial neoplasia (PIN) and metastatic cancer tissue in addition to primary cancer and non malignant tissue.

Figure 25:
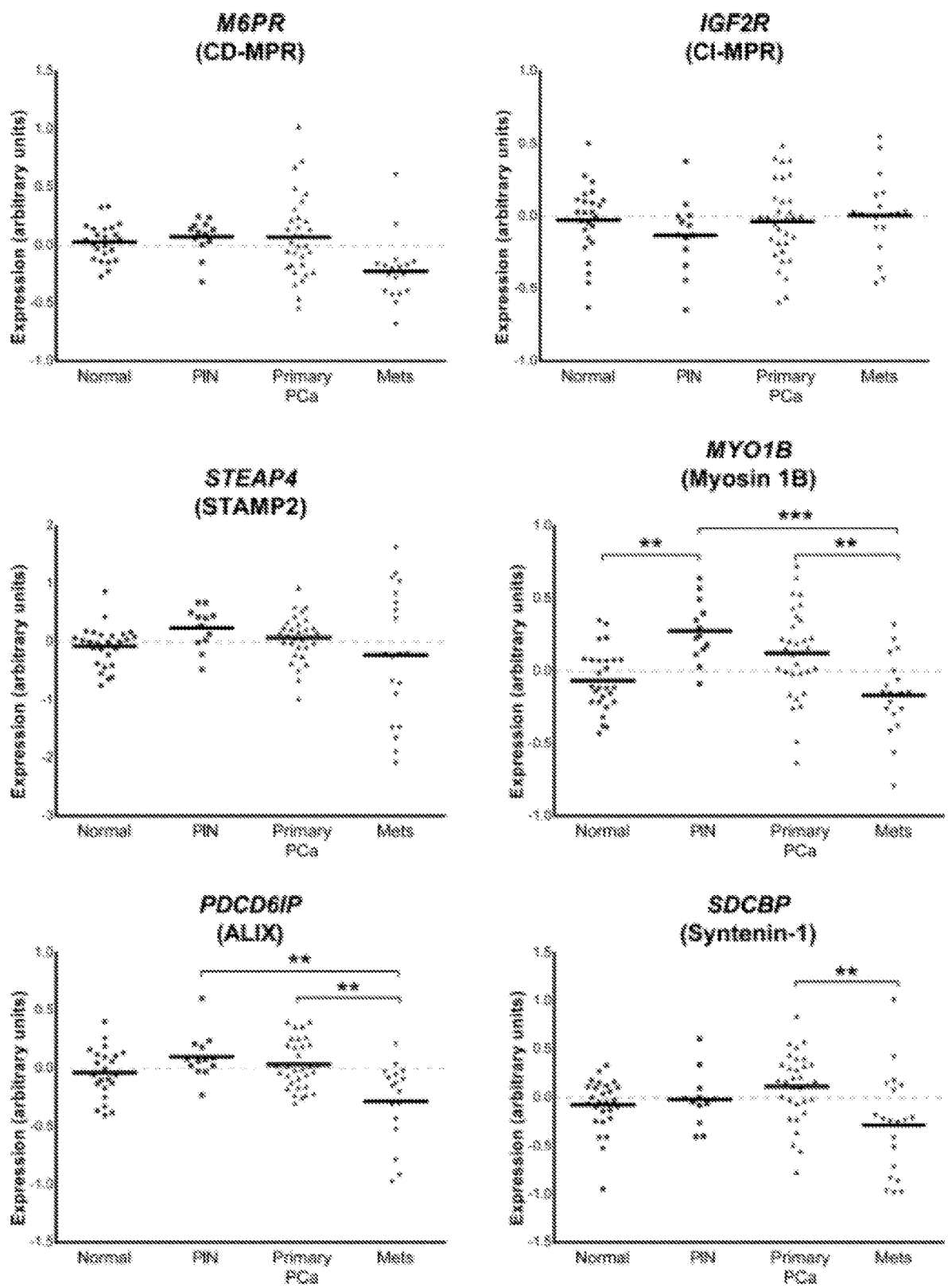
FIG. 25 shows vertical scatter plots of endosomal-lysosomal gene expression data from the cohort by Tomlins et al.

The data is shown in FIG. 25. Vertical scatter plots of lysosomal gene expression data from the cohort by Tomlins et al. Analysis of prostate cancer tissue revealed altered gene expression during prostate cancer progression. Expression profiling data derived from the Chinnaiyan Human 20K Hs6 array of 27 non-malignant tissues, 13 prostatic intraepithelial neoplasias, 32 primary prostate cancer and 22 metastatic cancer tissue samples (Tomlins et al. 2007) were quantitated to show relative expression of endosome-related genes. Statistical significance is represented by an asterisk ( $P \leq 0.01$; * $P \leq 0.001$).

The gene expression of M6PR and IGF2R and STEAP4 in the Tomlins cohort showed no significant change between normal, PIN, primary or metastatic cancer tissue. MYO1B, ALIX and SDCBP displayed differential expression in the prostate cancer tissue when compared to metastatic tissue ($P \leq 0.01$). Significant reductions in expression were observed between PIN and metastatic tissue for MYO1B ($P \leq 0.001$) and PDCD6IP ($P \leq 0.01$) but not for SDCBP. Expression of MYO1B was significantly increased in PIN tissue compared to non malignant prostate tissue ($P \leq 0.01$).

(ii) Prognostic Potential for Endosome-Related Genes to Stratify Patients at Risk of Biochemical Recurrence To assess the prognostic potential of expression of endosome-related genes, we classified patients from the Glinsky cohort into two groups using K means clustering based on gene expression. The Glinsky cohort microarray provides data of initial PSA levels detected upon biopsy, and information on relapse subsequent to therapy.

Figure 26A:
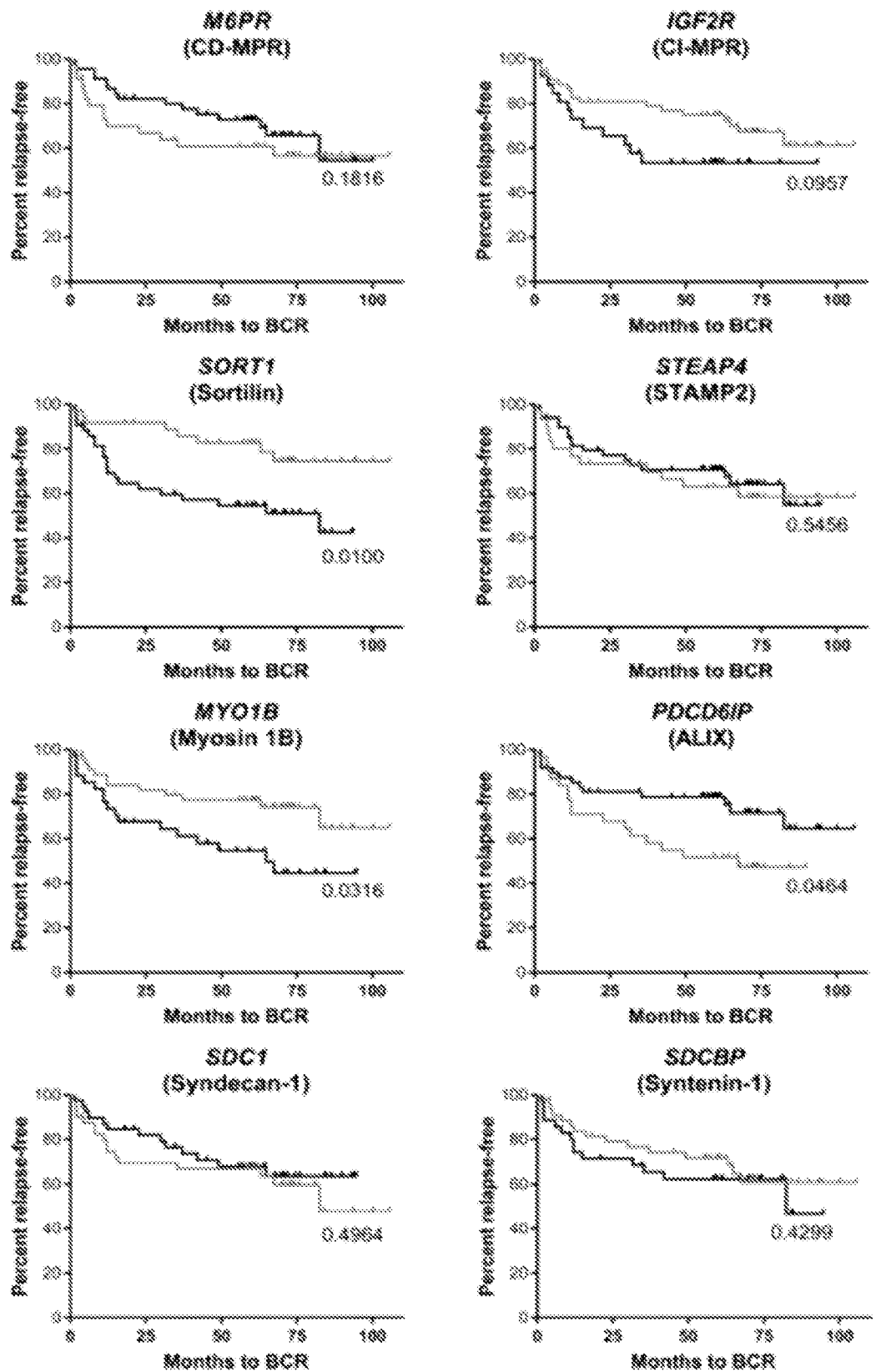

FIGS. 26A-26B show Kaplan-Meier analysis of endosome/lysosome-related genes and patient stratification based on biochemical recurrence (BCR). Gene expression of SORT1, MYO1B and PDCD61P stratified patients into prognostic risk groups. Patients from the Glinsky cohort (Glinsky et al. 2004) were stratified into two groups by K means clustering based on amount (high—black line, low—grey line) of M6PR, IGF2R, SORT1, STEAP4, MYO1B, PDCD61P, SDC1 and SDCBP gene expression. Analysis was performed using Gehan-Breslow-Wilcoxon test). BCR: biochemical recurrence; HR: hazard ratio; CI: confidence interval.

Clustering of high (black line) or low (grey line) SORT1 and MYO1B gene expression revealed patients with high expression had significantly increased risk of biochemical recurrence (BCR) ($P \leq 0.01$ and $P \leq 0.05$, respectively). Patients expressing lower amounts of PDCD6IP were at a significantly higher risk of BCR ($P \leq 0.05$). The grouping by high or low expression for M6PR, STEAP4, SDC1 and SDCBP genes did not stratify patients significantly into prognostic groups, however there was a trend observed for IGF2R ($P = 0.096$). The associated Table shows Kaplan-Meier analysis of endosome/lysosome-related genes and patient stratification based on biochemical recurrence (BCR). Gene expression of SORT1, MYO1B and PDCD61P stratified patients into prognostic risk groups. Patients from the Glinsky cohort (Glinsky et al. 2004) were stratified into two groups by K means clustering based on amount (high—black line, low—grey line) of M6PR, IGF2R, SORT1, STEAP4, MYO1B, PDCD61P, SDC1 and SDCBP gene expression. Analysis was performed using Gehan-Breslow-Wilcoxon test).

(iii) Prognostic Potential for Endosome-Related Genes in Patients Expressing PSA $\leq 7.8$ ng/.

Figure 27A:
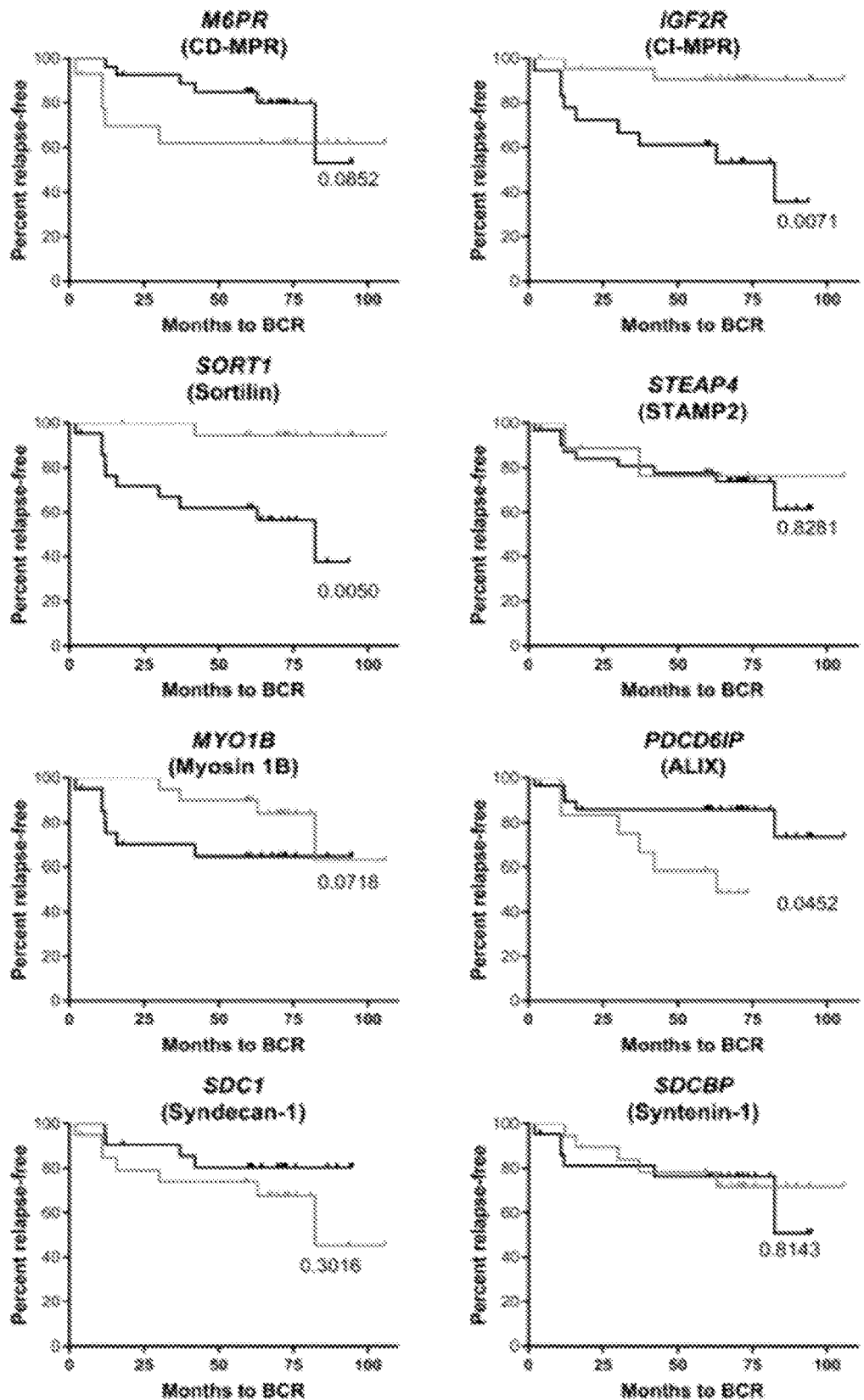

FIGS. 27A-27B show Kaplan-Meier survival and multivariate analysis of lysosomal gene expression for cancer patients expressing $\leq 7.8$ ng/mL PSA. Kaplan-Meier analysis of lysosome-related gene expression showed significant capability for prognosis in patients expressing $\leq 7.8$ ng/mL PSA based on IGF2R, SORT1 or PDCD61P expression.

From the good prognosis subgroup of PSA ≤7.8 ng/mL, patients were further stratified into two groups by K-means clustering based on gene expression of M6PR, IGF2R, SORT1, STEAP4, MYO1B, PDCD61P, SDC1 and SDCBP (high expression—black line, low expression—grey line). Statistical analysis was performed using Gehan-Breslow-Wilcoxon test. BCR: biochemical recurrence; HR: hazard ratio; CI: confidence interval.

Stratification of patients with PSA ≤7.8 ng/mL into high and low gene expression groups revealed that increased expression of IGF2R (P≤0.01), SORT1 (P≤0.01) or ALIX (P≤0.05) resulted in a significantly increased risk of BCR (FIGS. 27A-27B). There was a trend for low expression of M6PR and SDC1, and higher expression of MYO1B to stratify at-risk patients who expressed low PSA. The expression of STEAP4 or SDCBP did not appear to show any prognostic potential for those patients expressing low levels of PSA.

(iv) Gene Expression of Syntaxin 7 (STX7) and Syntaxin 12 (STX12) is Reduced Significantly in Prostate Cancer Tissue.

The expression of Syntaxin 7 and Syntaxin 12 mRNA transcripts was analysed from the Taylor cohort in prostate cancer tissue compared to non malignant tissue.

Figure 28:
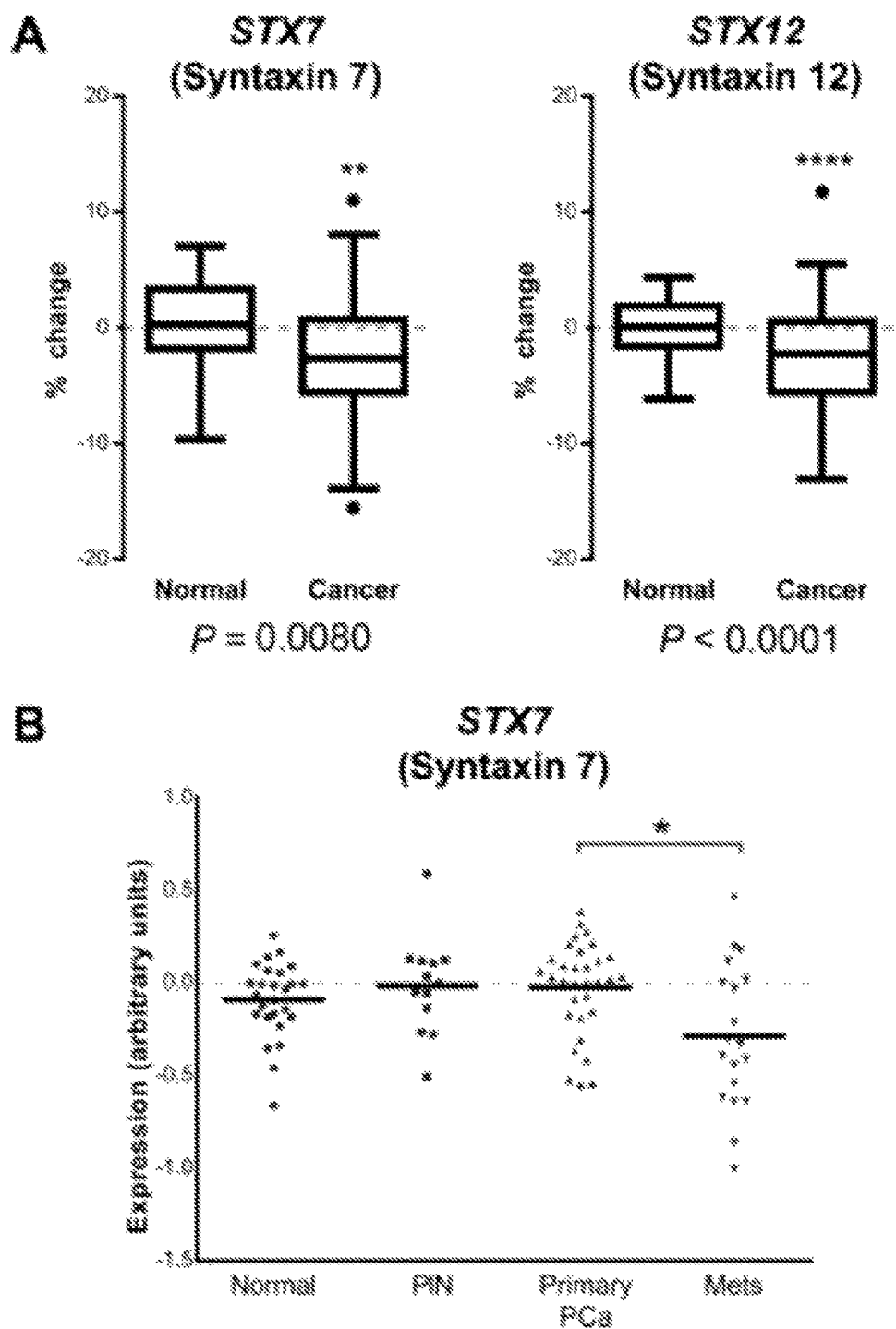
FIG. 28 shows (A) Box-and-whisker graphs showing percentage change in gene expression of Syntaxin 7 and Syntaxin 12. (B) Vertical scatter plots of gene expression data from the cohort by Tomlins et al.

FIG. 28 in Panel A shows box-and-whisker graphs showing percentage change in gene expression of Syntaxin 7 and Syntaxin 12. Panel B shows vertical scatter plots of gene expression data from the cohort by Tomlins et al. Panel A shows expression profiling data derived from Affymetrix Human Exon 1.0 ST arrays of 150 primary prostate cancers and 29 non-malignant tissues (Taylor 2010) were quantitated to show percentage change of gene expression of STX7 and STX12. Box-and-whisker graphs were plotted with Tukey outliers (black points). Statistical significance is represented by an asterisk ( P≤0.01; ** P≤0.0001). Panel B shows analysis of prostate cancer tissue revealed altered STX7 gene expression during prostate cancer progression. Expression profiling data derived from the Chinnaiyan Human 20K Hs6 array of 27 non-malignant tissues, 13 prostatic intraepithelial neoplasias, 32 primary prostate cancer and 22 metastatic cancer tissue samples (Tomlins et al. 2007) were quantitated to show relative expression of endosome-related genes. Statistical significance is represented by an asterisk (* P≤0.05).

There was a statistically significant reduction in the expression of STX7 (P≤0.01) and STX12 (P≤0.0001; FIG. 28 A) in primary cancer tissue compared to non malignant tissue. Analysis of STX7 gene expression during prostate cancer progression from the Tomlins cohort showed a significant reduction in gene expression of metastatic tissue compared to primary cancer tissue (P≤0.05; FIG. 28 B).

(v) Prognostic Potential of Syntaxin 7 and 12 to Stratify Patients at Risk of Biochemical Recurrence.

To assess the prognostic potential of expression of Syntaxin 7 and 12 gene expression, we classified patients from the Glinsky cohort into two groups using K means clustering based on gene expression.

Figure 29:
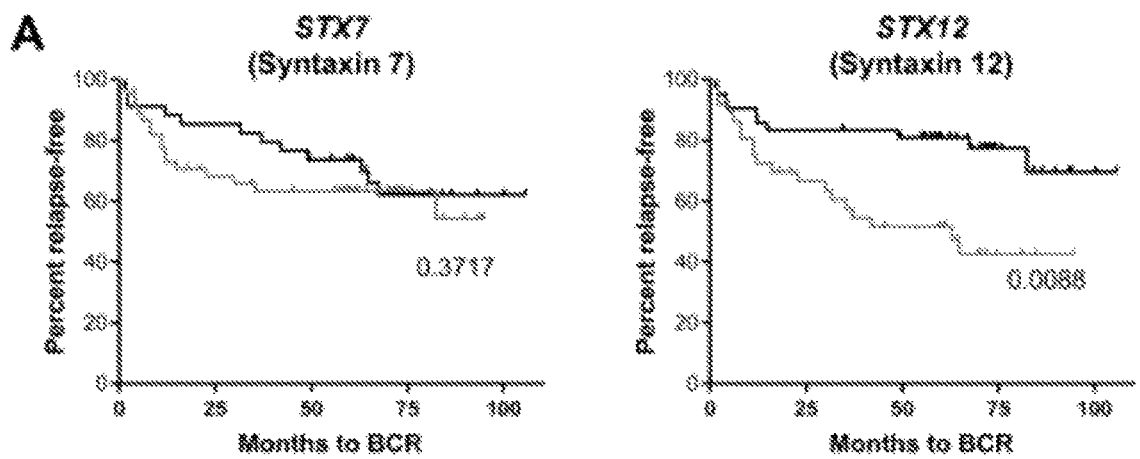
FIG. 29 shows Kaplan-Meier survival analysis of Syntaxin 7 and Syntaxin 12 gene expression.
Figure 29:
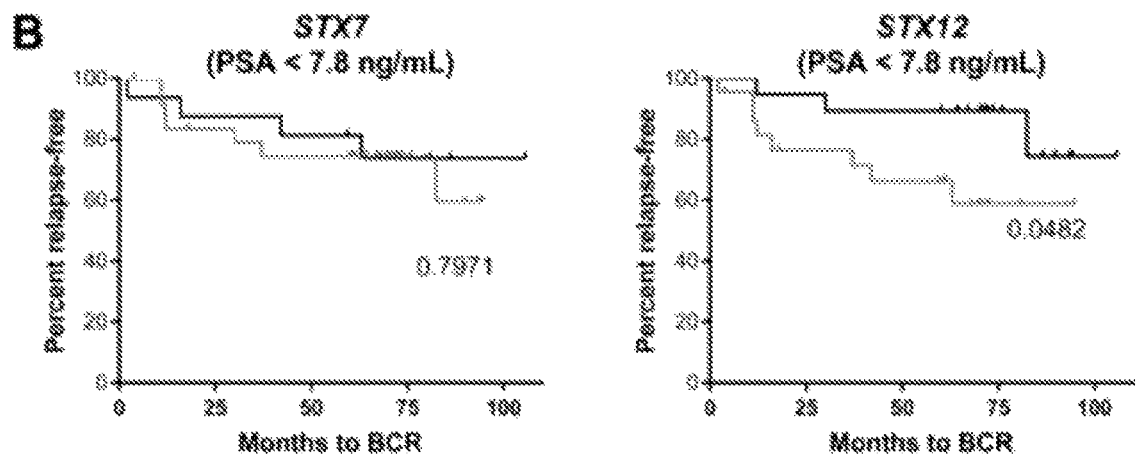

FIG. 29 shows Kaplan-Meier survival analysis of Syntaxin 7 and Syntaxin 12 gene expression. (A) Kaplan-Meier analysis of lysosome-related gene expression showed significant capability for prognosis based on STX12 expression. (B) From the "good-prognosis" subgroup of PSA ≤7.8 ng/mL, patients were further stratified into two groups by K-means clustering based on gene expression of STX7 and STX12 (high expression—black line, low expression—grey line). Statistical analysis was performed using Gehan-Breslow-Wilcoxon test. BCR: biochemical recurrence; HR: hazard ratio; CI: confidence interval.

Clustering of high (black line) or low (grey line) STX12 gene expression revealed patients with low expression had significantly increased risk of biochemical recurrence (BCR) (P≤0.01), however there was no prognostic capacity of STX7 (FIG. 29 A). Stratification of patients with PSA ≤7.8 ng/mL into high and low gene expression groups revealed that decreased expression of STX12 resulted in a significantly increased risk (P≤0.05) of BCR (FIG. 29 B), whilst there was no capacity of STX7 to stratify patients.

(vi) Secreted, but not Intracellular, Amounts of Endosome-Related Machinery are Significantly Altered in Prostate Cancer Cells.

Figure 30:
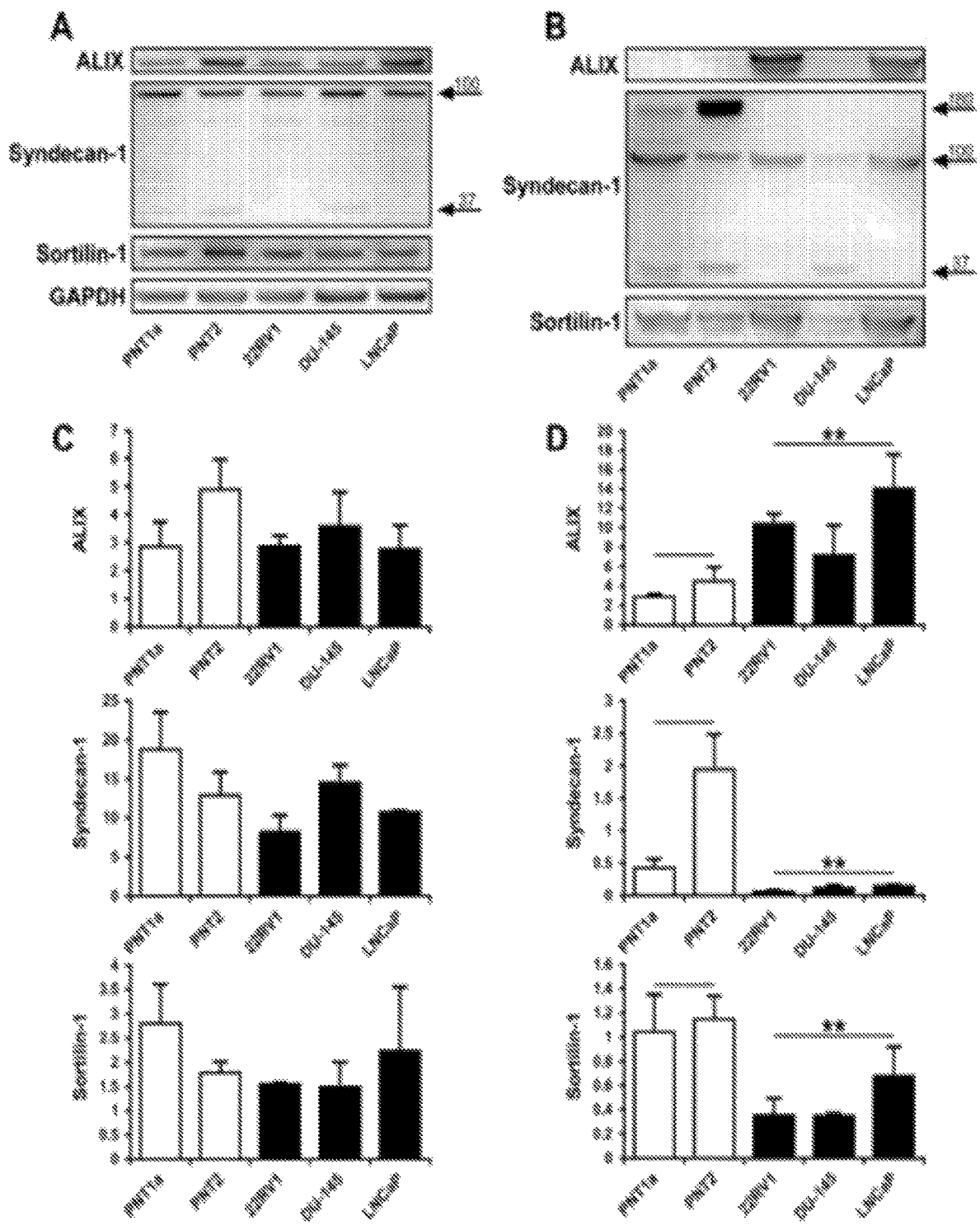
FIG. 30 shows detection and quantification of intracellular and secreted endosome-related proteins.

Western blotting was used to define the amount of ALIX, Syndecan-1 and Sortilin-1 in cell lysates and culture media from the non-malignant prostate cell lines (PNT1a and PNT2) and the prostate cancer cell lines (22RV1, DU-145 and LNCaP). FIG. 30 shows detection and quantification of intracellular and secreted endosome-related proteins. (A) Representative images from Western blot analysis of endosome-related proteins/GAPDH in cell extract (A; 10 μg whole cell lysate) and culture media (B; 3 mL culture collected after 48 hours incubation with confluent cells and corrected for cell number) from non-malignant control cell lines PNT1a and PNT2, and cancer cell lines 22RV1, DU-145 and LNCaP, examined in triplicate.

Western blotting was used to define the amount of ALIX, Syndecan-1 and Sortilin-1 in cell lysates and culture media from the non-malignant prostate cell lines (PNT1a and PNT2) and the prostate cancer cell lines (22RV1, DU-145 and LNCaP). While the intracellular amounts of these proteins was unaltered in cancer cells compared to nonmalignant cells (FIG. 30 A, C), there was a significant increase in the amount of ALIX detected in the culture media from prostate cancer compared to nonmalignant control cell lines (P≤0.01; FIG. 30 C, D). Syndecan-1 and Sortilin-1 was detected in the culture media from prostate cancer cell lines at a significantly reduced level (P≤0.01) compared to non malignant cells.

(vii) FGF1 Gene Expression is Reduced in Prostate Cancer Tissue.

Figure 31:
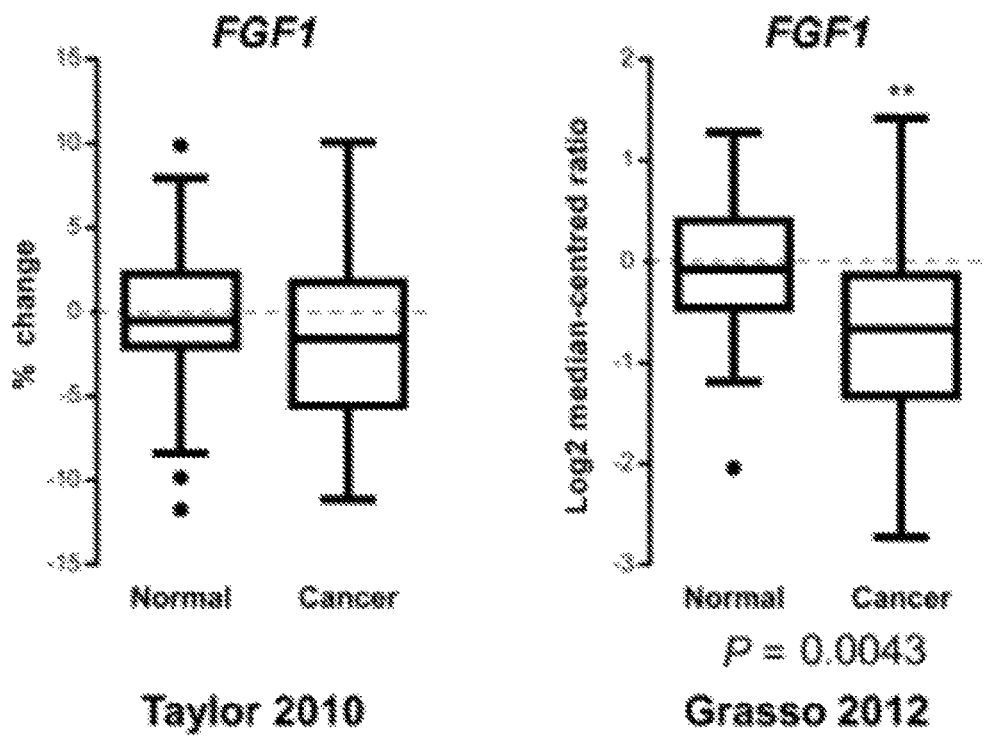
FIG. 31 shows box-and-whisker graphs showing percentage change in gene expression of FGF1 (Taylor cohort) and Log 2 median-centred ratio (Grasso cohort) and vertical scatter plot of gene expression data from the cohort by Tomlins et al.
Figure 31:
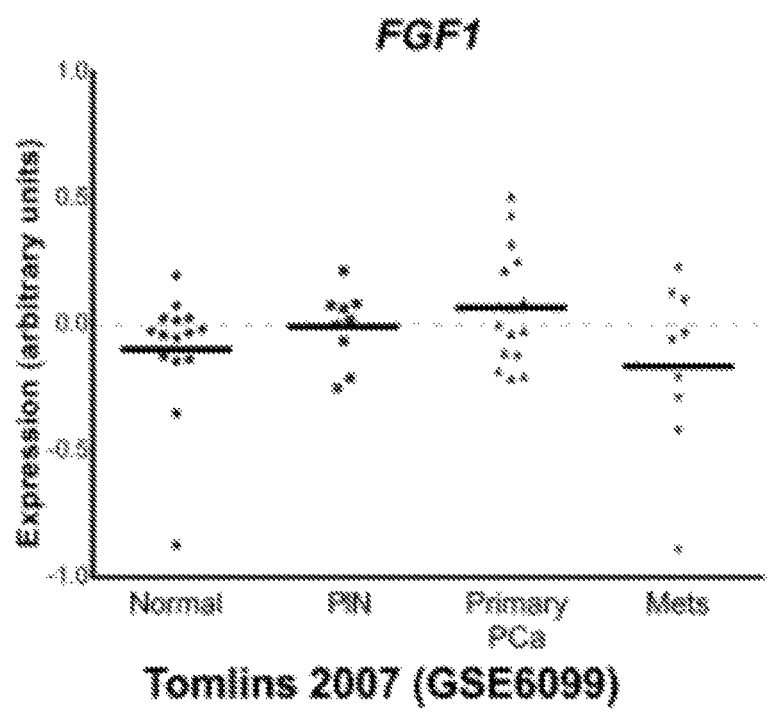

FIG. 31 shows box-and-whisker graphs showing percentage change in gene expression of FGF1 (Taylor cohort) and Log 2 median-centred ratio (Grasso cohort) and vertical scatter plot of gene expression data from the cohort by Tomlins et al. Box-and-whisker graphs were plotted with Tukey outliers (black points). Statistical significance is represented by an asterisk (** P≤0.01).

Analysis of FGF1 gene expression in microarrays showed a reduction that was statistically significant in the Grasso cohort (P≤0.01). There was evidence of a reduction in the Taylor cohort however this was not statistically significant. Expression of FGF1 from the Tomlins cohort showed variability between tissue disease stages.

(viii) FGF2 Gene Expression is Reduced in Prostate Cancer Tissue.

Figure 32:
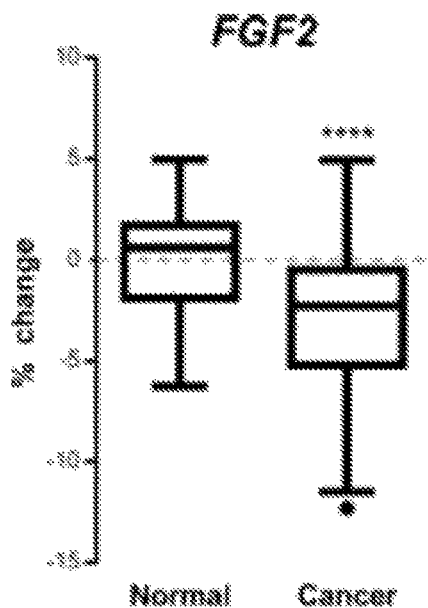
FIG. 32 shows box-and-whisker graphs showing percentage change in gene expression of FGF2 (Taylor cohort) and Log 2 median-centred ratio (Grasso cohort) and vertical scatter plot of gene expression data from the cohort by Tomlins et al.
Figure 32:
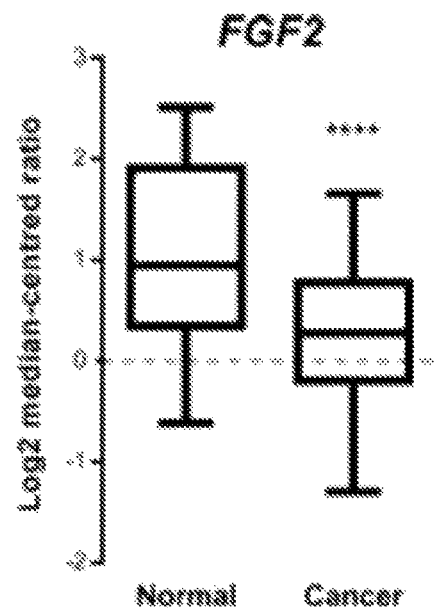
Figure 32:
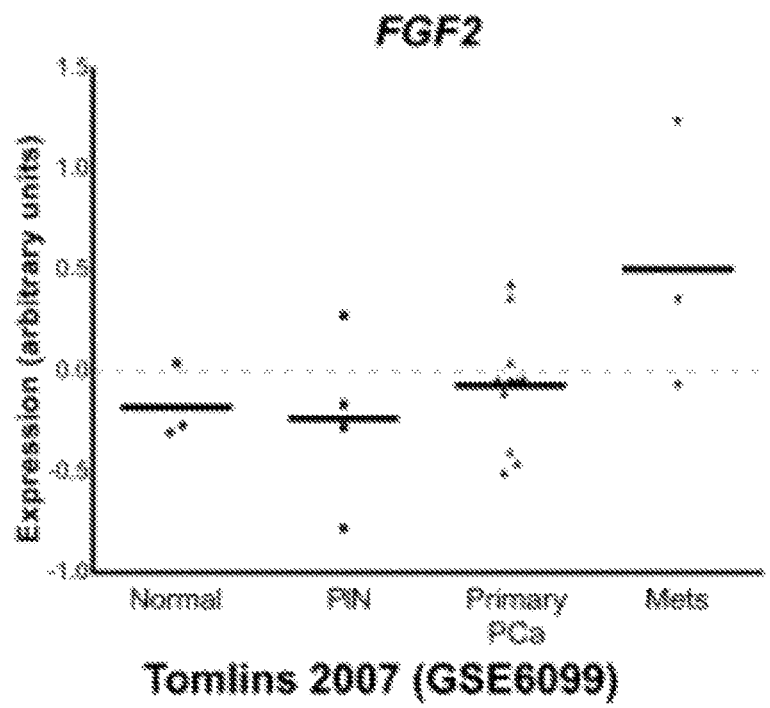

FIG. 32 shows box-and-whisker graphs showing percentage change in gene expression of FGF2 (Taylor cohort) and Log 2 median-centred ratio (Grasso cohort) and vertical scatter plot of gene expression data from the cohort by Tomlins et al. Box-and-whisker graphs were plotted with Tukey outliers (black points). Statistical significance is represented by an asterisk (**** P≤0.0001).

Analysis of FGF2 gene expression in microarrays showed a reduction that was statistically significant in both the Taylor and Grasso cohort (P≤0.0001). There was variability in tissue types from the Tomlins cohort that may be attributed to the limited data available for this gene in the cohort.

(ix) FGF3 Gene Expression is Reduced in Prostate Cancer Tissue.

Figure 33:
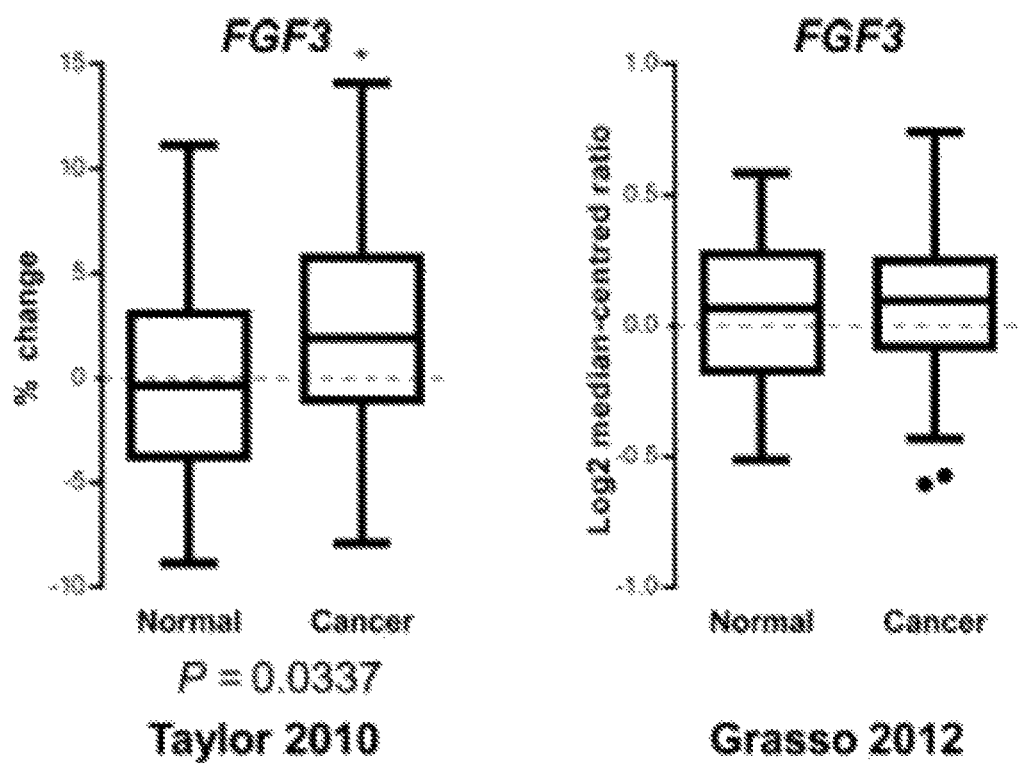
FIG. 33 shows box-and-whisker graphs showing percentage change in gene expression of FGF3 (Taylor cohort) and Log 2 median-centred ratio (Grasso cohort) and vertical scatter plot of gene expression data from the cohort by Tomlins et al.

FIG. 33 shows box-and-whisker graphs showing percentage change in gene expression of FGF3 (Taylor cohort) and Log 2 median-centred ratio (Grasso cohort) and vertical scatter plot of gene expression data from the cohort by Tomlins et al. Box-and-whisker graphs were plotted with Tukey outliers (black points). Statistical significance is represented by an asterisk (* P≤0.05).

Analysis of FGF3 gene expression in microarrays showed a significant increase in the Taylor cohort (P≤0.05), however there was not a significant increase in FGF3 expression in the Grasso cohort.

(x) Kaplan-Meier Analysis of FGF2 Suggests a Trend for Increased Risk of Relapse in Patients with Lower FGF2 Expression.

Figure 34:
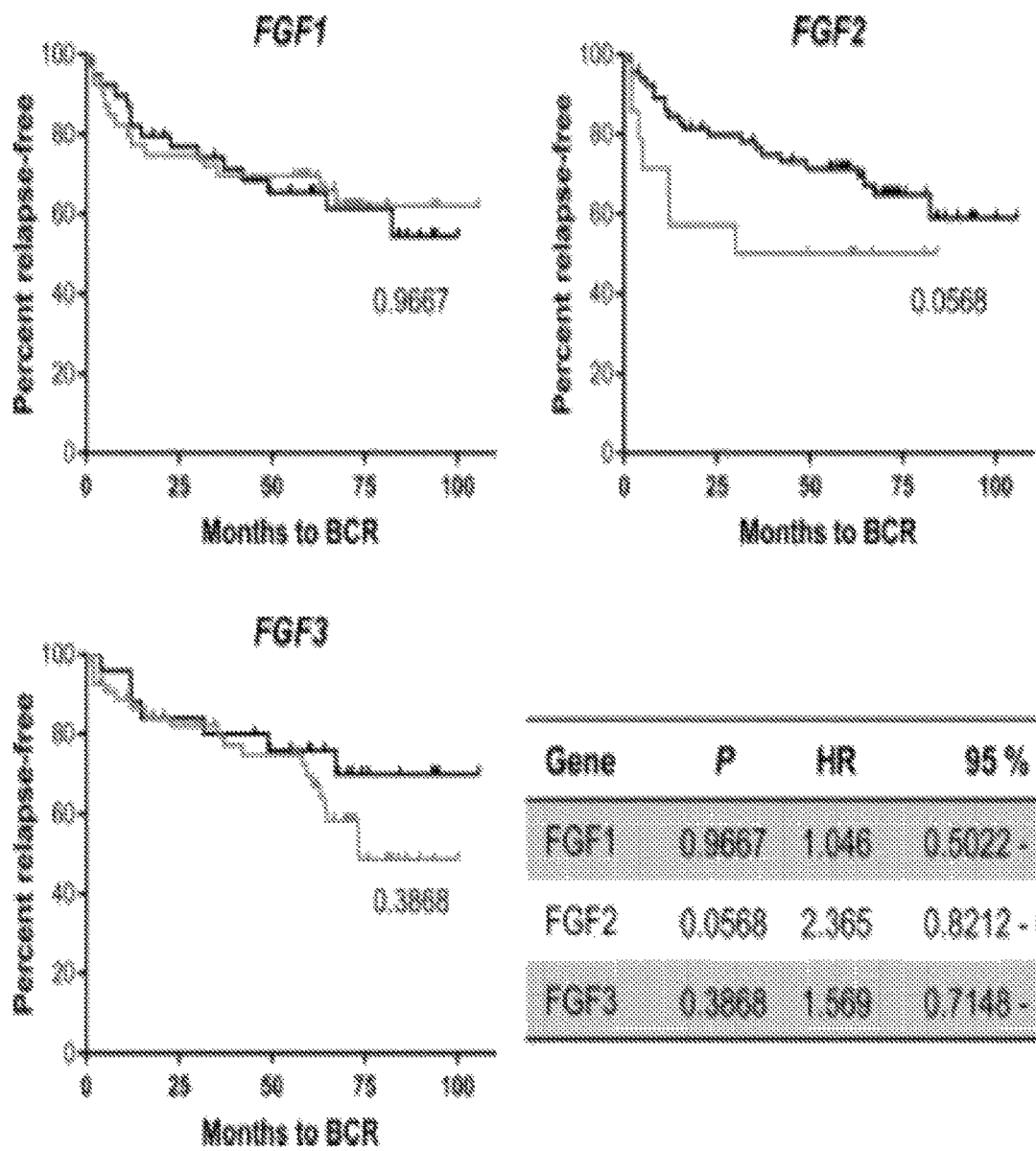
FIG. 34 shows Kaplan-Meier survival analysis of FGF1, FGF2 and FGF3 gene expression.

FIG. 34 shows Kaplan-Meier survival analysis of FGF1, FGF2 and FGF3 gene expression. The Kaplan-Meier analysis of FGF-related gene expression showed some potential capability for prognosis based on FGF2 expression.

Kaplan-Meier analysis of FGF-related gene expression showed some capability for prognosis based on FGF2 expression however this was not statistically significant. Patients were not stratified into 'high' or 'low' FGF1 or FGF3 groups.

(xi) Kaplan-Meier Analysis of FGF-Related Genes Showed Prognostic Value in Patients Expressing PSA ≤7.8 ng/mL.

Figure 35:
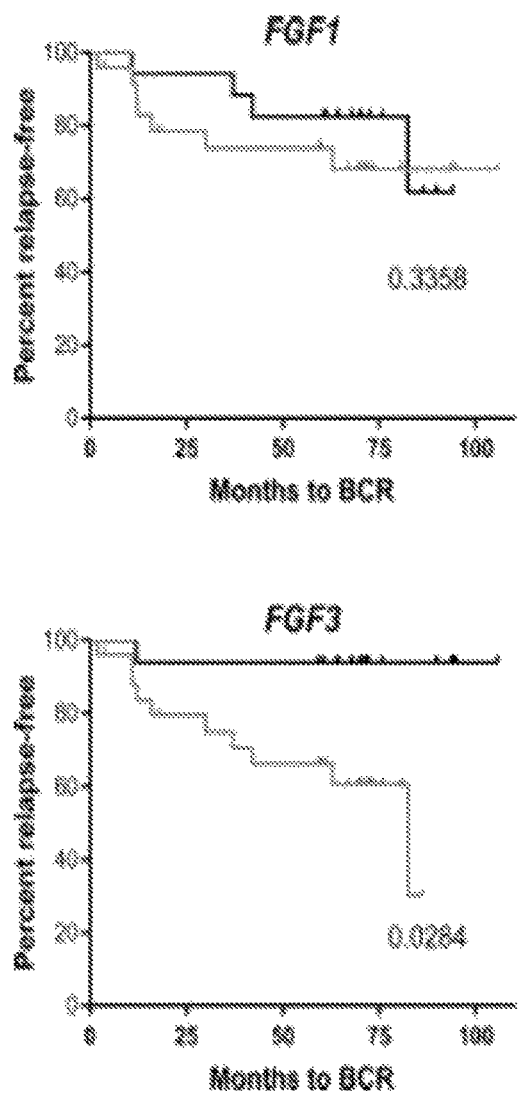
FIG. 35 shows Kaplan-Meier survival analysis of FGF1, FGF2 and FGF3 gene expression.

FIG. 35 shows Kaplan-Meier survival analysis of FGF1, FGF2 and FGF3 gene expression. From the "good-prognosis" subgroup of PSA ≤7.8 ng/mL, patients were further stratified into two groups by K-means clustering based on gene expression of FGF1, FGF2 and FGF3 (high expression—black line, low expression—grey line). Statistical analysis was performed using Gehan-Breslow-Wilcoxon test. BCR: biochemical recurrence; HR: hazard ratio; CI: confidence interval.

Clustering of high (black line) or low (grey line) gene expression of FGF genes revealed patients that expressed low PSA protein that had low expression of FGF2 or FGF3 had significantly increased risk of biochemical recurrence (P≤0.05), however there was no apparent prognostic capacity for FGF1.

(xii) FGFR1 Gene Expression is Reduced in Prostate Cancer Tissue.

Figure 36:
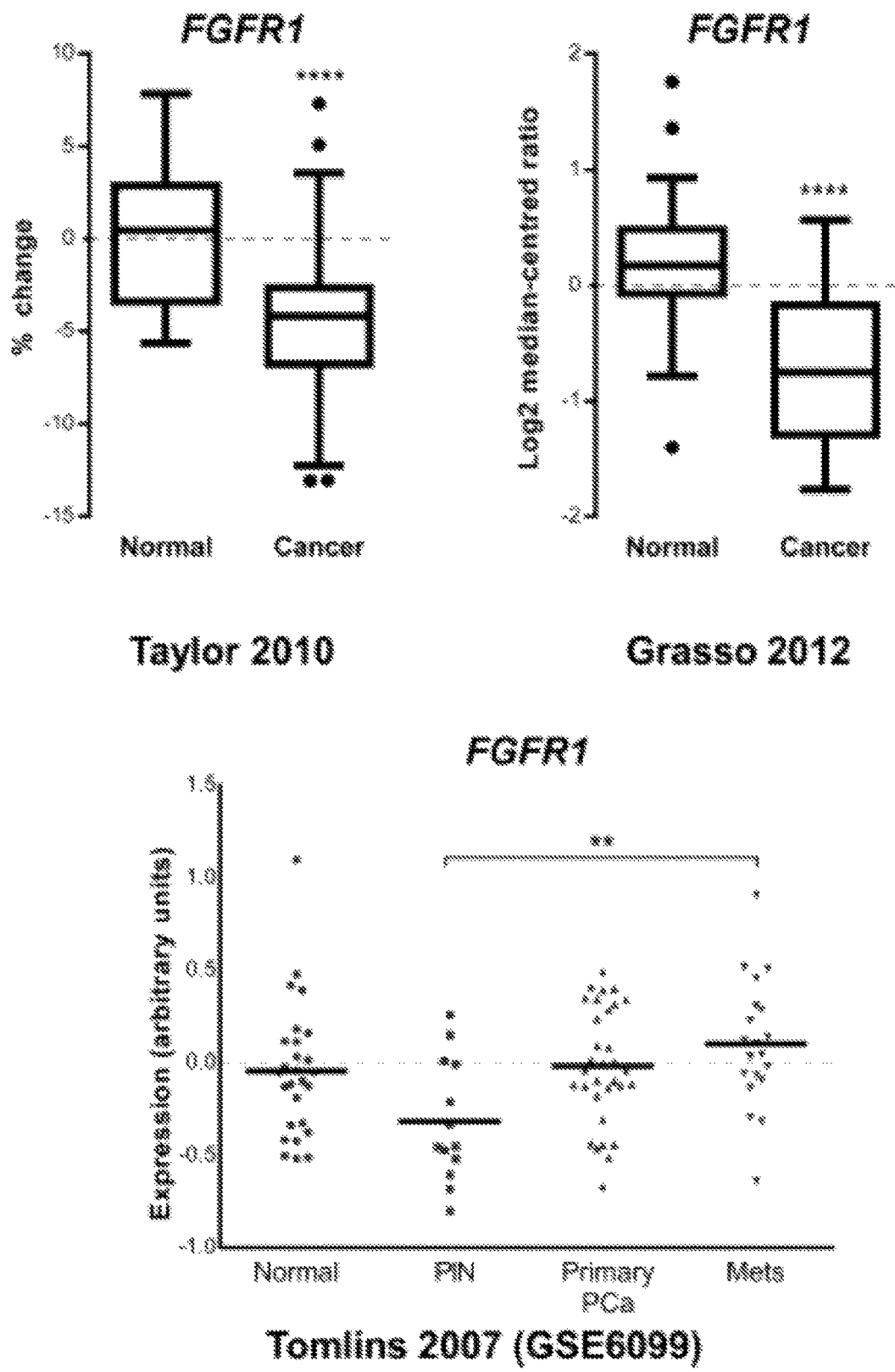
FIG. 36 shows box-and-whisker graphs showing percentage change in gene expression of FGFR1 (Taylor cohort) and Log 2 median-centred ratio (Grasso cohort) and vertical scatter plot of gene expression data from the cohort by Tomlins et al. Statistical significance is represented by an asterisk (** P≤0.0001;  P≤0.01).

FIG. 36 shows a box-and-whisker graphs showing percentage change in gene expression of FGFR1 (Taylor cohort) and Log 2 median-centred ratio (Grasso cohort) and vertical scatter plot of gene expression data from the cohort by Tomlins et al. Statistical significance is represented by an asterisk (** P≤0.0001; P≤0.01).

Analysis of FGFR1 gene expression in microarrays showed a reduction in prostate cancer tissue that was statistically significant in the Taylor and Grasso cohorts (P≤0.0001). Across tissue types, there was a reduction in PIN tissue compared to nonmalignant tissue and a statistically significant increase (P≤0.01) in gene expression between PIN and metastatic tissue.

(xiii) FGFR2 Gene Expression is Significantly Reduced in Prostate Cancer Tissue.

Figure 37:
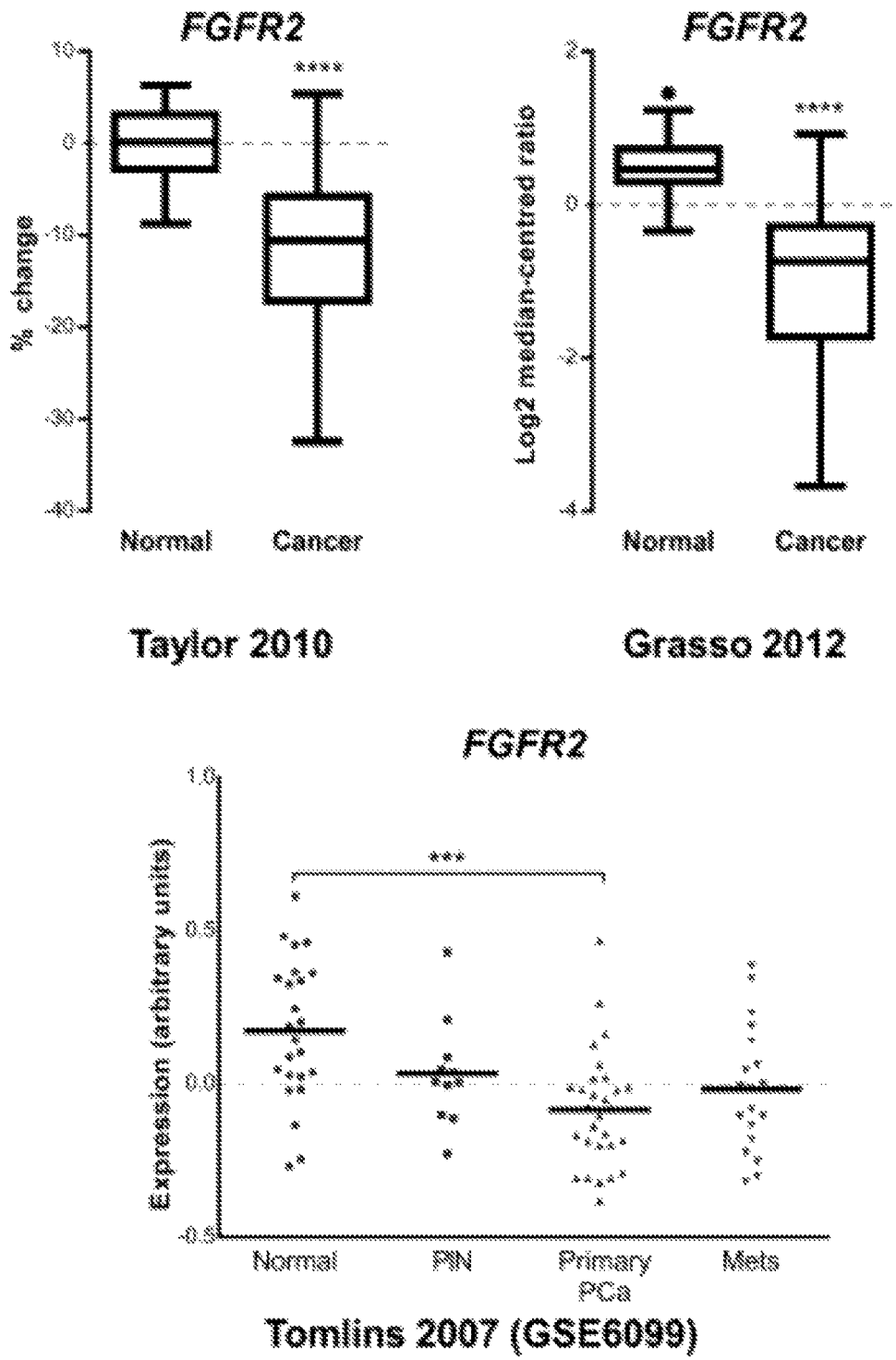
FIG. 37 shows box-and-whisker graphs showing percentage change in gene expression of FGFR2 (Taylor cohort) and Log 2 median-centred ratio (Grasso cohort) and vertical scatter plot of gene expression data from the cohort by Tomlins et al. Statistical significance is represented by an asterisk (** P≤0.0001; *P≤0.001).

FIG. 37 shows box-and-whisker graphs showing percentage change in gene expression of FGFR2 (Taylor cohort) and Log 2 median-centred ratio (Grasso cohort) and vertical scatter plot of gene expression data from the cohort by Tomlins et al. Statistical significance is represented by an asterisk (** P≤0.0001; *P≤0.001).

Analysis of FGFR2 gene expression in microarrays showed a reduction in prostate cancer tissue that was statistically significant in the Taylor and Grasso cohorts (P≤0.0001). Across tissue types, there was a reduction in PIN tissue and metastatic tissue compared to nonmalignant tissue, and a statistically significant reduction (P≤0.001) in gene expression in primary cancer tissue compared to non-malignant tissue in the Tomlins cohort.

(xiv) FGFR3 Gene Expression is Significantly Reduced in Prostate Cancer Tissue.

Figure 38:
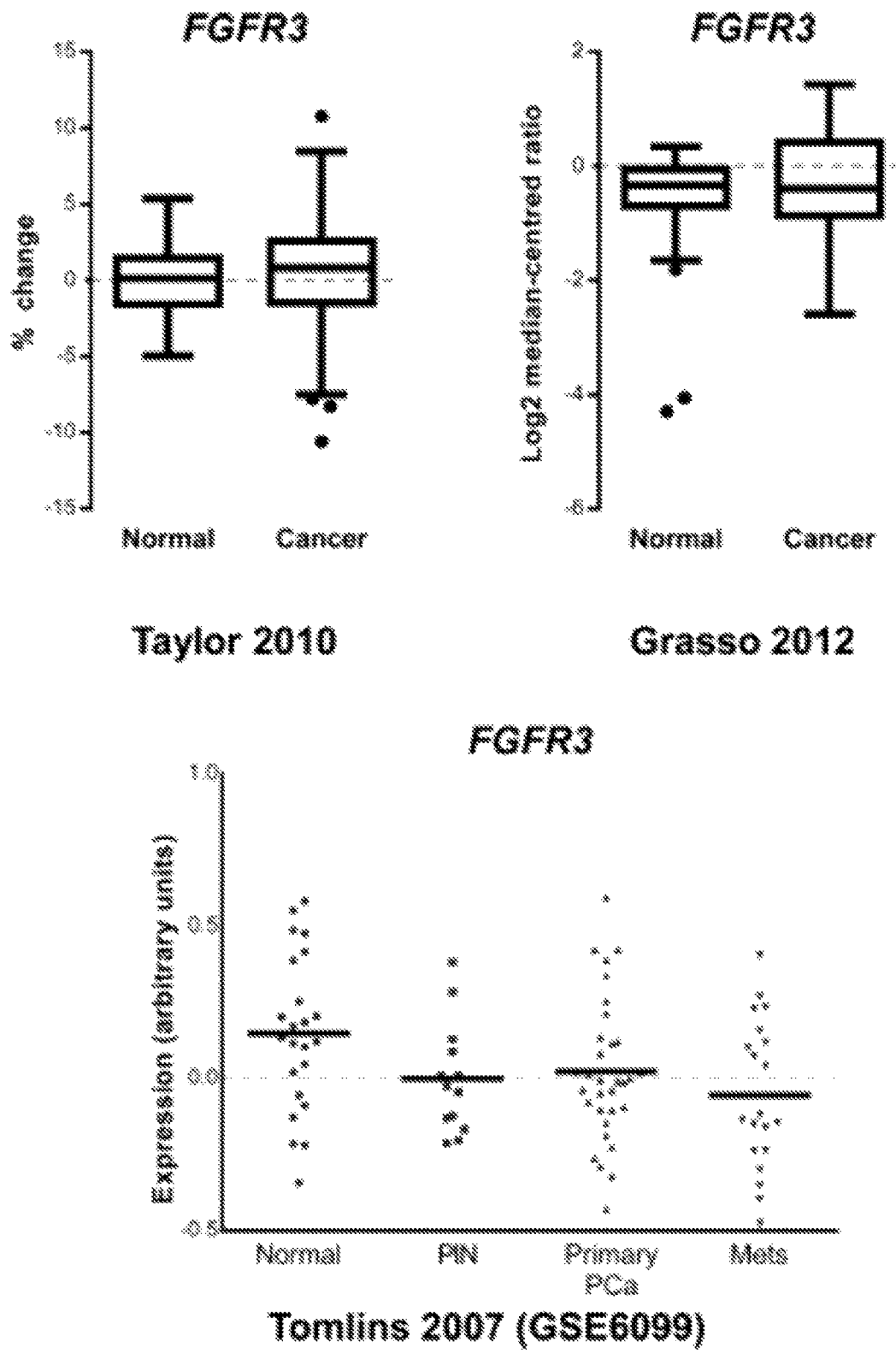
FIG. 38 shows box-and-whisker graphs showing percentage change in gene expression of FGFR3 (Taylor cohort) and Log 2 median-centred ratio (Grasso cohort) and vertical scatter plot of gene expression data from the cohort by Tomlins et al.

FIG. 38 shows box-and-whisker graphs showing percentage change in gene expression of FGFR3 (Taylor cohort) and Log 2 median-centred ratio (Grasso cohort) and vertical scatter plot of gene expression data from the cohort by Tomlins et al.

Analysis of FGFR3 gene expression in microarrays showed no significant change in FGFR3 expression in prostate cancer tissue compared to nonmalignant prostate tissue. The expression of FGFR3 showed evidence of a reduction in each disease state compared to normal tissue in the Tomlins cohort however this was not statistically significant.

(xv) Kaplan-Meier Analysis of FGFR-Related Genes Showed Prognostic Value in Patients Expressing.

Figure 39:
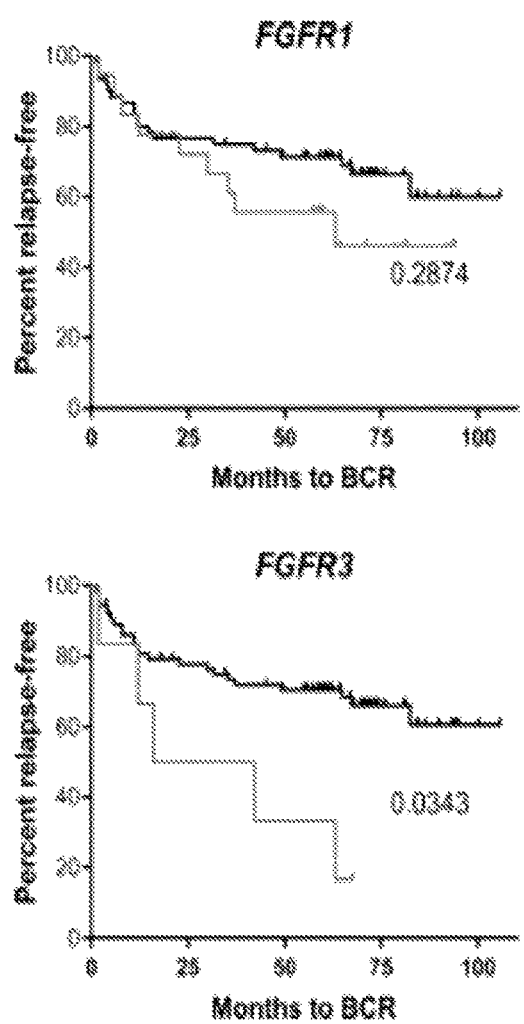
FIG. 39 shows Kaplan-Meier survival analysis of FGFR1, FGFR2 and FGFR3 gene expression.
Figure 39:
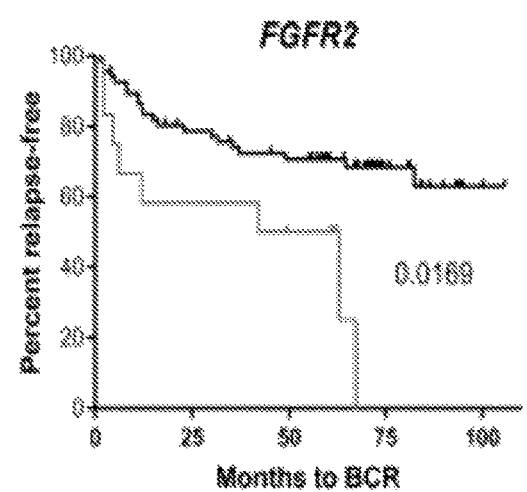

FIG. 39 shows Kaplan-Meier survival analysis of FGFR1, FGFR2 and FGFR3 gene expression. The Kaplan-Meier analysis of FGFR-related gene expression from the Glinksy cohort showed some potential capability for prognosis based on FGFR2 or FGFR3 expression.

Clustering of high (black line) or low (grey line) gene expression of FGFR genes revealed patients that had lower FGFR2 or FGFR3 gene expression were at a significantly greater risk of biochemical recurrence (P≤0.05) compared to those patients expressing a higher amount of FGFR2 or FGFR3. There was no significant stratification of patients expressing FGFR1 for this dataset.

Figure 40:
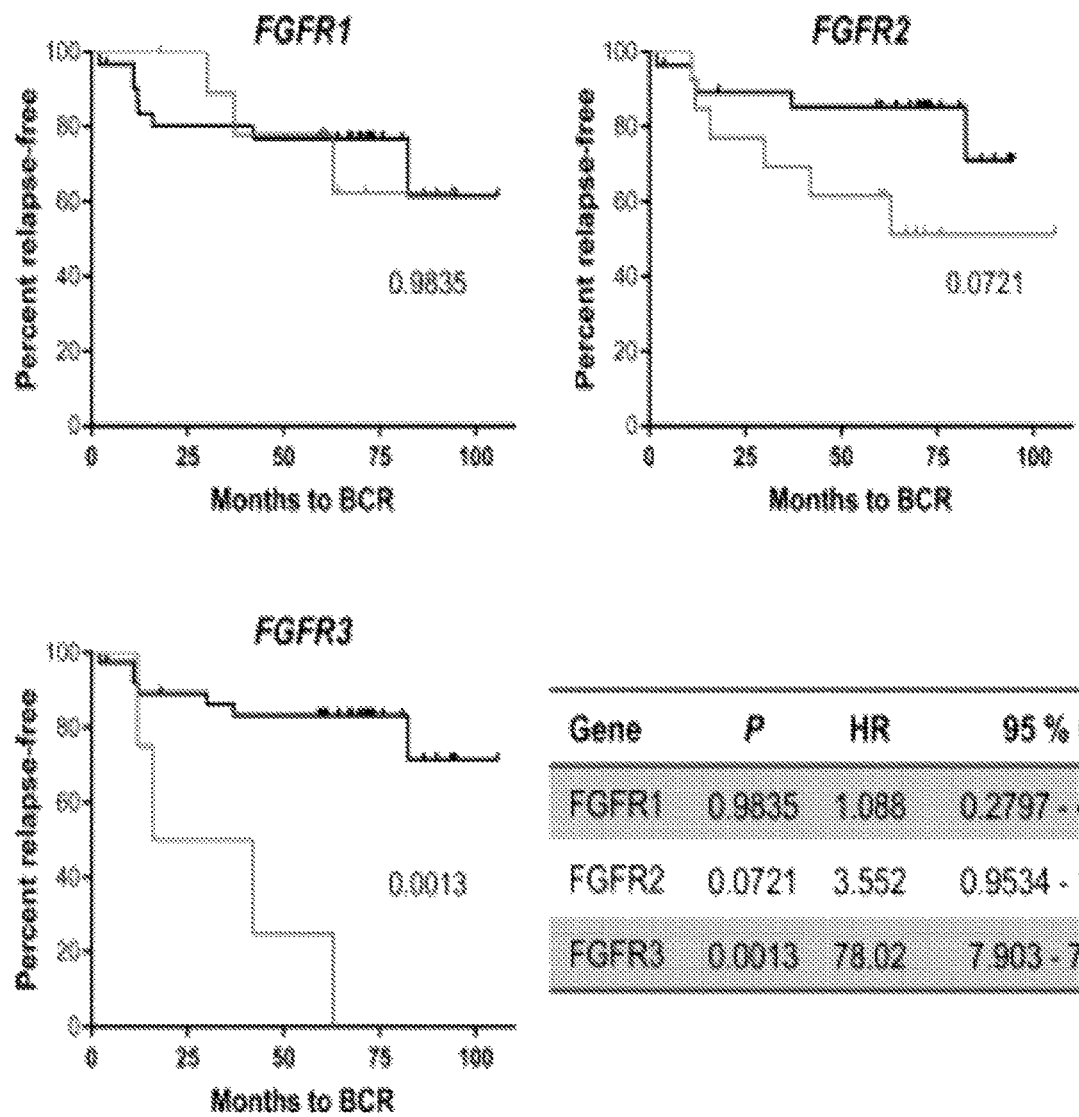
FIG. 40 shows Kaplan-Meier survival analysis of FGFR1, FGFR2 and FGFR3 gene expression.

(xvi) Kaplan-Meier Analysis of FGFR3 Showed Prognostic Value in Patients Expressing PSA ≤7.8 ng/mL FIG. 40 shows Kaplan-Meier survival analysis of FGFR1, FGFR2 and FGFR3 gene expression. From the "good-prognosis" subgroup of PSA ≤7.8 ng/mL, patients were further stratified into two groups by K-means clustering based on gene expression of FGFR1, FGFR2 and FGFR3 (high expression—black line, low expression—grey line). Statistical analysis was performed using Gehan-Breslow-Wilcoxon test. BCR: biochemical recurrence; HR: hazard ratio; CI: confidence interval.

Clustering of high (black line) or low (grey line) gene expression of FGFR genes revealed patients that expressed low PSA protein that had low expression of FGFR3 had a significantly increased risk of biochemical recurrence (P≤0.001). There was a trend for lower expression of FGFR2 to suggest increased risk of biochemical recurrence. No stratification of patients was achieved clustering groups into high or low expression of FGFR1.

(xvii) NOX2 Protein is Significantly Increased in Prostate Cancer Cells.

Figure 41:
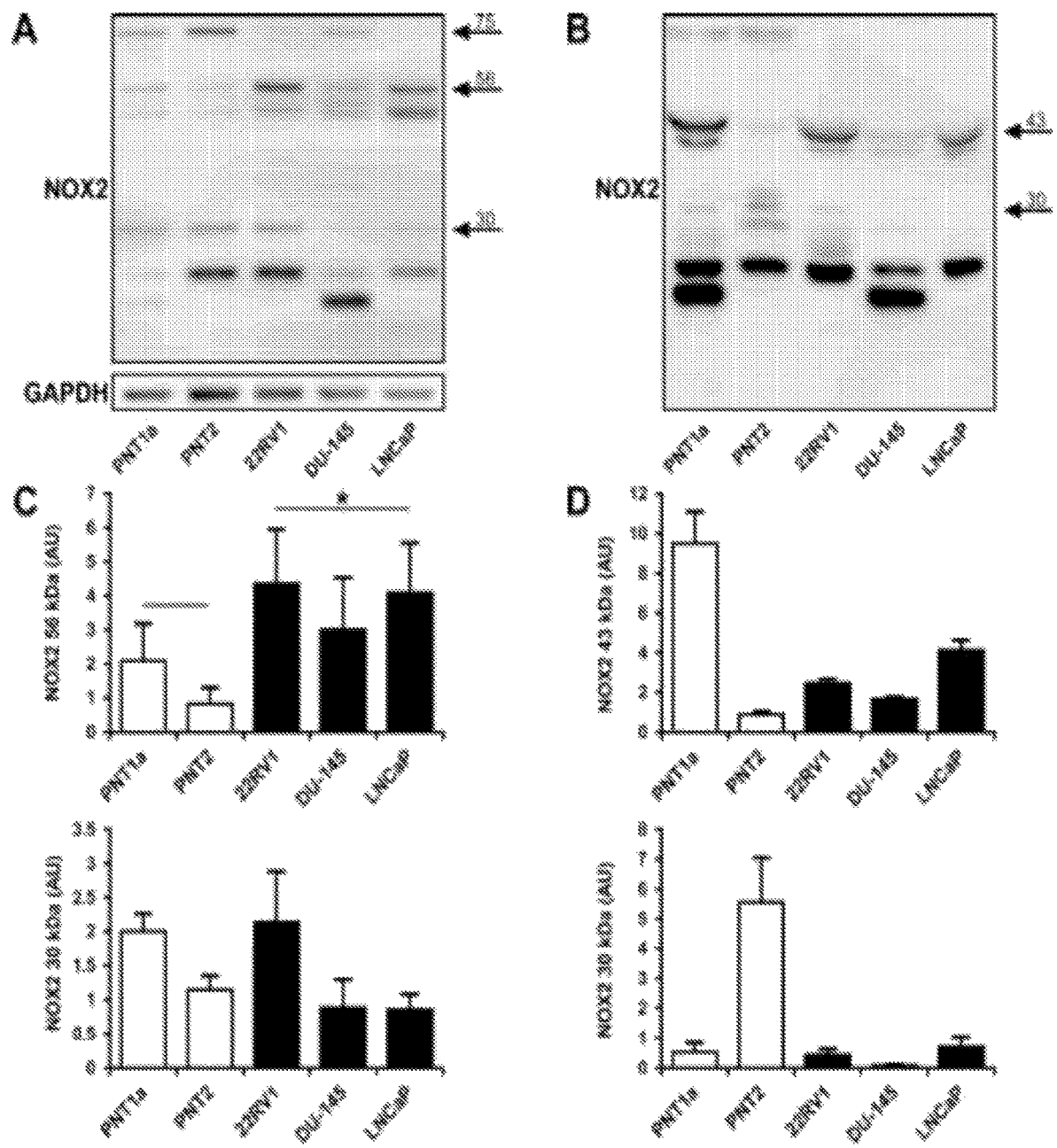
FIG. 41 shows detection and quantification of NOX2 protein (65 (56) & 30 kDa) from non-malignant control and prostate cancer cell lines.

FIG. 41 shows detection and quantification of NOX2 protein (65 (56) & 30 kDa) from non-malignant control and prostate cancer cell lines. Representative images from western blot analysis of (A) 10 μg whole cell lysate and (B) secreted NOX2 protein from non-malignant control cell lines PNT1a and PNT2, and cancer cell lines 22RV1, DU-145 and LNCaP, examined in triplicate. (C) The amount of intracellular NOX2 was quantified by densitometry relative to a GAPDH endogenous control. (D) Quantification of secreted NOX2 protein was normalised to cell count at time of protein collection. Data was analysed by clustered linear regression with statistical significance (P≤0.05) represented by an asterisk.

Western blotting was used to define the amount of NOX2 in cell lysates and culture media from the non malignant prostate cell lines (PNT1a and PNT2) and the prostate cancer cell lines (22RV1, DU-145 and LNCaP). The intracellular amount of NOX2 (56 kDa) was significantly increased in cancer cells compared to non malignant cells (FIG. 41 A, C). An isoform of NOX2 (30 kDa) was expressed in non malignant and prostate cancer cells however this was not significantly altered. There was no secretion of a 56 kDa form of NOX2 however there was evidence of secretion of a 30 kDa isoform from prostate cancer and nonmalignant cells (FIG. 41 B, D). NOX2 Antibody—Rabbit Polyclonal from Abcam, cat #ab31092 used at 1/2000 dilution (0.5 µg/mL).

(xviii) Altered NOX2 Gene Expression in Prostate Cancer Tissue.

Figure 42:
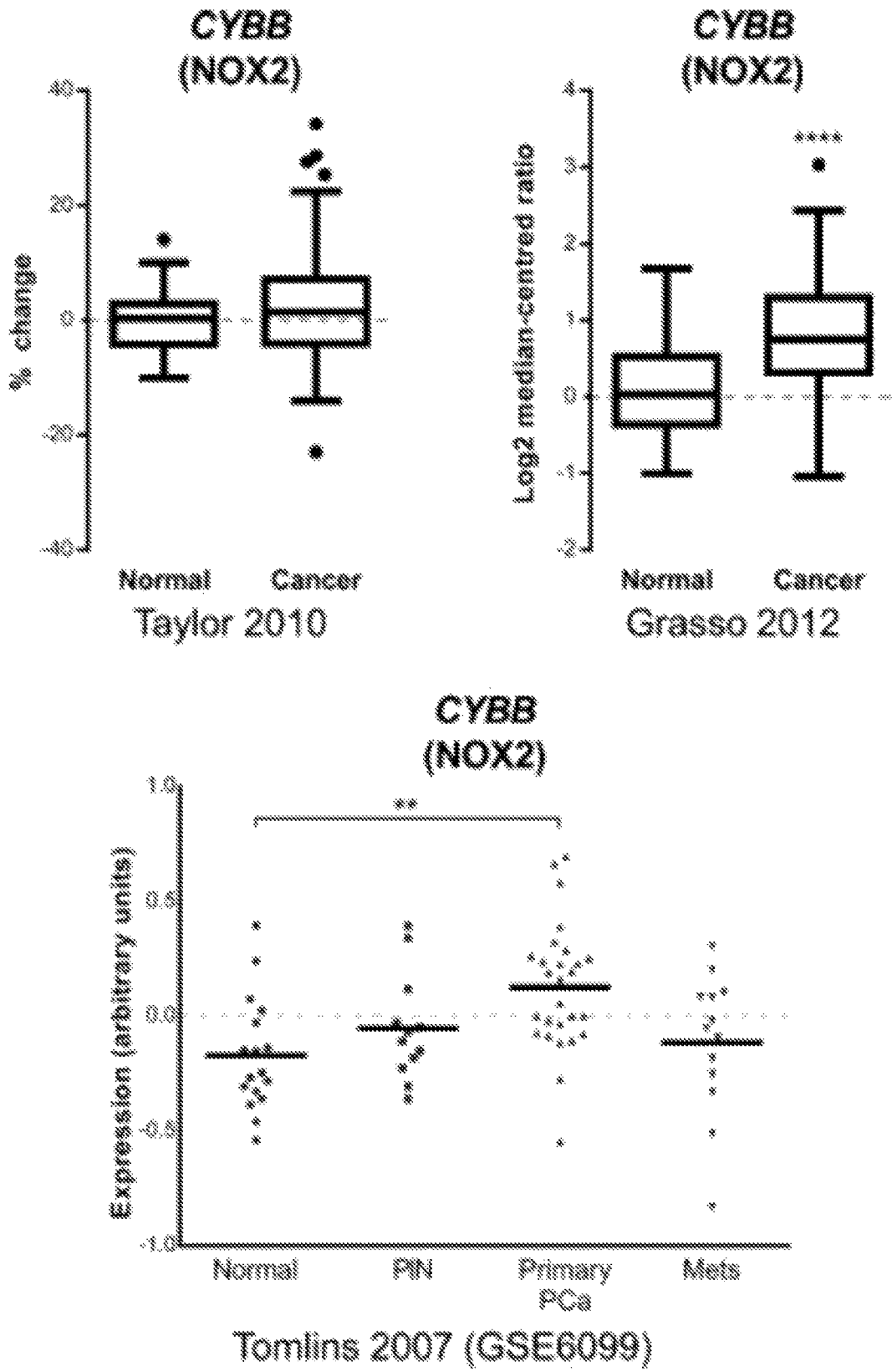
FIG. 42 shows box-and-whisker graphs showing percentage change in gene expression of NOX2 (Taylor cohort) and Log 2 median-centred ratio (Grasso cohort) and vertical scatter plot of gene expression data from the cohort by Tomlins et al. Statistical significance is represented by an asterisk (** $P \leq 0.0001$,  $P \leq 0.01$).

FIG. 42 shows box-and-whisker graphs showing percentage change in gene expression of NOX2 (Taylor cohort) and Log 2 median-centred ratio (Grasso cohort) and vertical scatter plot of gene expression data from the cohort by Tomlins et al. Statistical significance is represented by an asterisk (** P≤0.0001, P≤0.01).

The expression of NOX2 transcript was analysed from the Tomlins, Taylor and Grasso cohorts. The gene expression of NOX2 showed a significant increase in cancer tissue of the Grasso cohort (P≤0.0001) compared to non malignant tissue. Analysis of disease types of the Tomlins cohort revealed altered expression across disease stages, and a significant increase (P≤0.01) of NOX2 expression in primary cancer tissue compared to nonmalignant normal prostate tissue.

(xix) NOX4 is Unaltered in Prostate Cancer Cells Compared to Non Malignant Cells.

Figure 43:
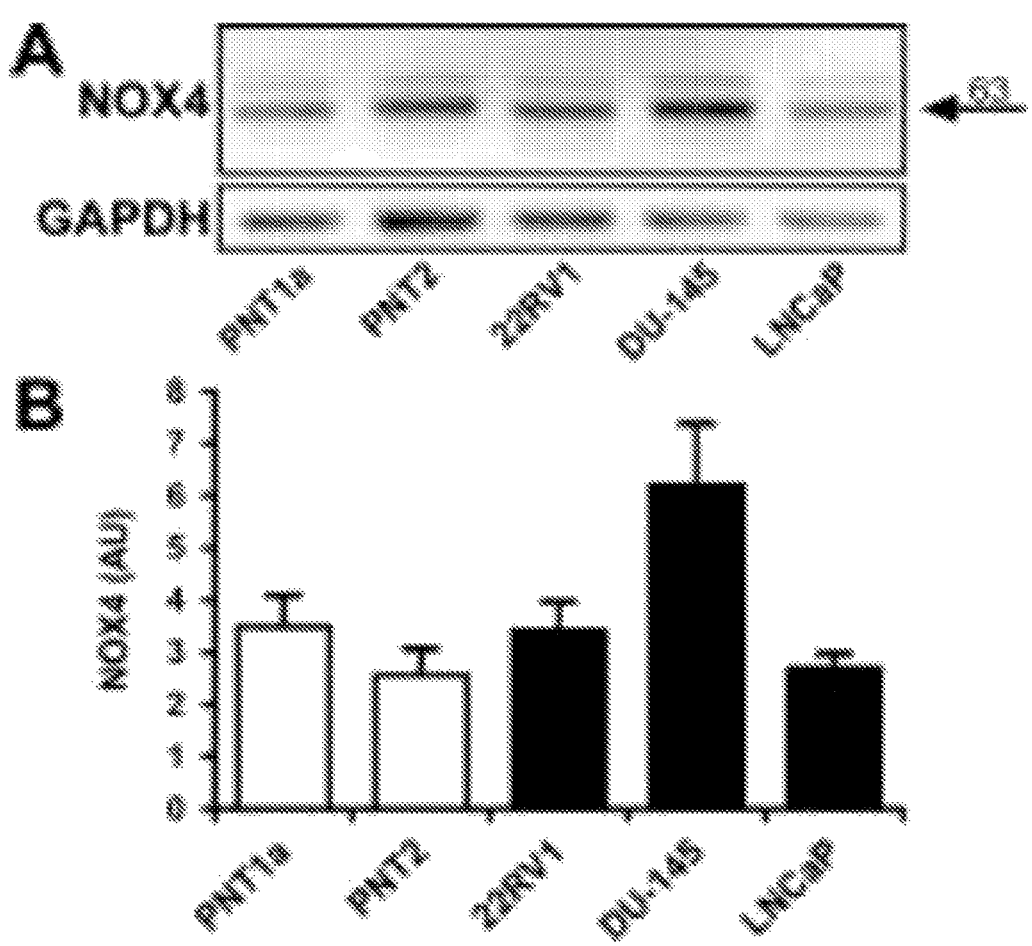
FIG. 43 shows detection and quantification of NOX4 protein from non-malignant control and prostate cancer cell lines.

FIG. 43 shows detection and quantification of NOX4 protein from non-malignant control and prostate cancer cell lines. (A) Representative image from western blot analysis of 10 µg whole cell lysate from non-malignant control cell lines PNT1a and PNT2, and cancer cell lines 22RV1, DU-145 and LNCaP, examined in triplicate. (B) The amount of intracellular NOX4 protein was quantified by densitometry relative to a GAPDH endogenous control. Data was analysed by clustered linear regression and no statistical significance was found between non-malignant and cancer cell line groups. Secreted protein from these cell lines was analysed (see NOX2), however no signal was detected for NOX4.

Western blotting was used to define the amount of NOX4 in cell lysates and culture media from the non-malignant prostate cell lines (PNT1a and PNT2) and the prostate cancer cell lines (22RV1, DU-145 and LNCaP). The intracellular amount of NOX4 (63 kDa) was unaltered in cancer cells compared to non malignant cells (FIG. 43 A, B). No secreted NOX4 protein was detectable (data not shown).

(xx) Altered NOX4 Gene Expression in Prostate Cancer Tissue.

Figure 44:
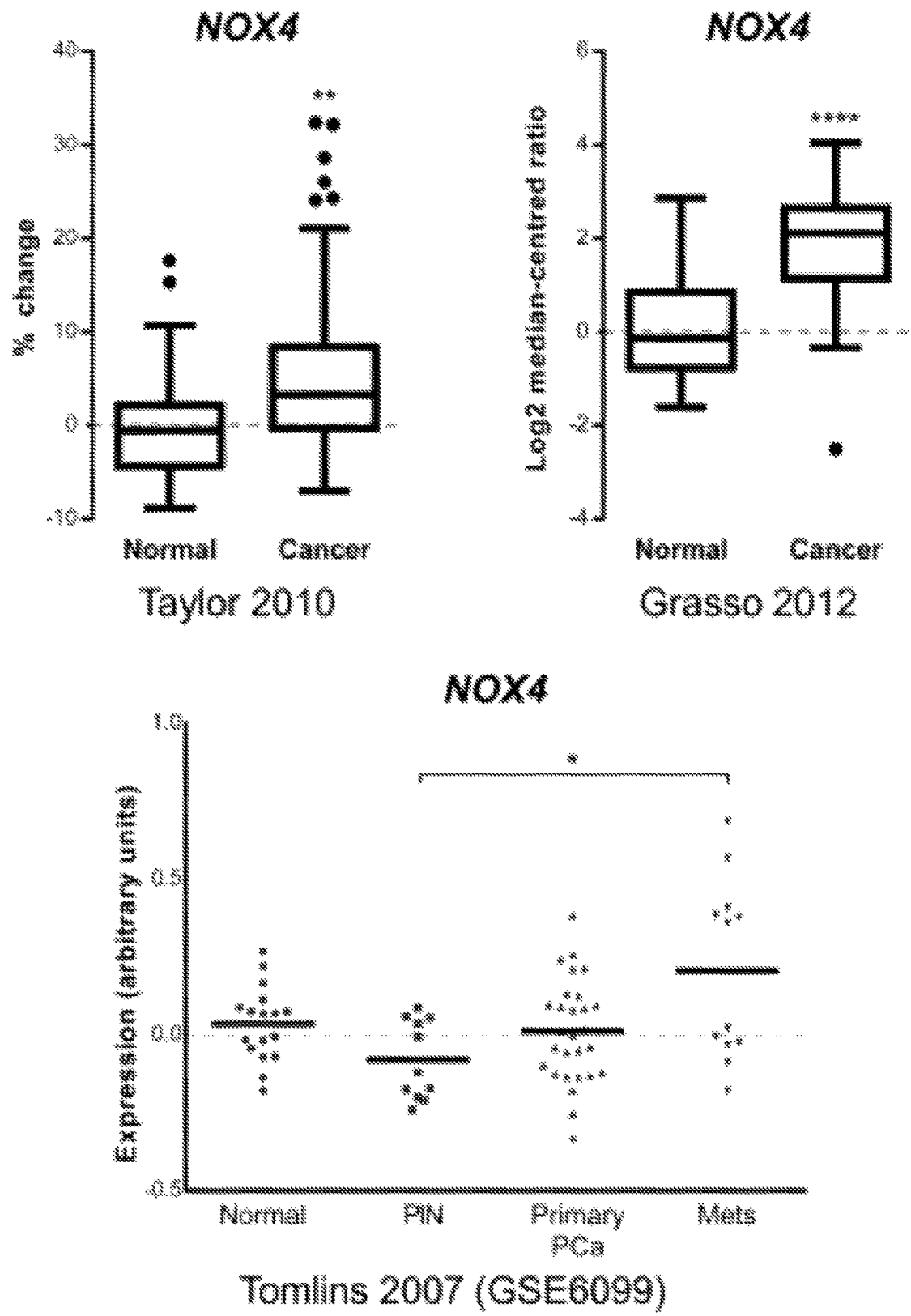
FIG. 44 shows box-and-whisker graphs showing percentage change in gene expression of NOX4 (Taylor cohort) and Log 2 median-centred ratio (Grasso cohort) and vertical scatter plot of gene expression data from the cohort by Tomlins et al. Statistical significance is represented by an asterisk (** $P \leq 0.0001$,  $P \leq 0.01$,* $P \leq 0.05$).

FIG. 44 shows box-and-whisker graphs showing percentage change in gene expression of NOX4 (Taylor cohort) and Log 2 median-centred ratio (Grasso cohort) and vertical scatter plot of gene expression data from the cohort by Tomlins et al. Statistical significance is represented by an asterisk (** P≤0.0001,  P≤0.01,* P≤0.05).

The expression of NOX4 transcript was analysed from the Tomlins, Taylor and Grasso cohorts. The gene expression of NOX4 showed a significant increase in cancer tissue of the Taylor and Grasso cohorts (P≤0.01 and P≤0.0001, respectively) compared to nonmalignant tissue. Analysis of disease types of the Tomlins cohort showed a significant increase (P≤0.05) of NOX4 expression in metastatic tissue compared to PIN tissue. NOX4 antibody—Rabbit monoclonal from Abcam, cat #ab133303 used at 1/2000 dilution (0.5 µg/mL)

(xxi) Altered APPL1, Rab7 and LIMPII Expression in Prostate Tissue (FIG. 49).

Figure 45:
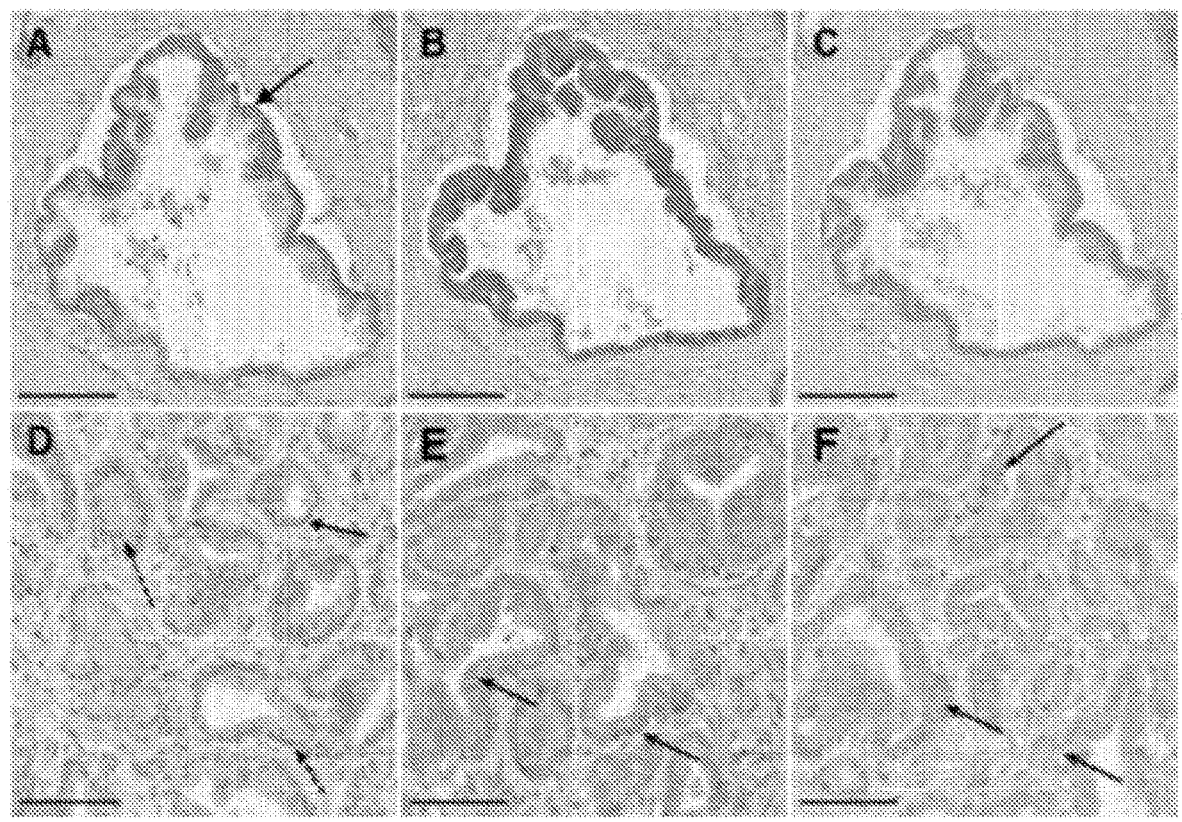
FIG. 45 shows APPL1, Rab7 and LIMPII expression in prostate tissue.

FIG. 45 shows APPL1, Rab7 and LIMPII expression in prostate tissue. APPL1, Rab7 and LIMPII in matched human non-malignant (A, B, C) and malignant (D, E, F) prostate tissue. The arrow in A shows APPL1 staining the basement membrane in non-malignant prostate tissue. In malignant prostate tissue: (D) dashed arrows show APPL1 staining both nuclei and nucleoli and solid arrow shows apparent nuclear membrane staining; (E) arrow shows apparent Rab7 nuclear membrane staining (F) arrows show enlarged LIMPII positive vesicles. Scale bar=100 µM in A, B & C and 200 µM in D, E, F. Antibodies used: rabbit anti APPL1 #3 (Detection Ab), rabbit anti Rab7 #1 (Detection Ab), sheep anti LIMPII Ab.

Immunohistochemistry was used to investigate the distribution of APPL1, the small GTPase Rab7 and LIMPII in prostate cancer tissue. The endosomal marker APPL1 showed significant basement membrane staining in non-malignant prostate tissue. In malignant tissue, there appeared to be increased staining associated with tumour mass and excitingly very specific nuclear and nucleoli staining in tumour cells. This staining was not seen in non-malignant tissue. For Rab7 specific cytoplasmic staining was observed in the stroma and glandular structures in non-malignant tissue. In contrast clear nuclear membrane staining was observed in malignant tissue with what appeared to be a decrease in the amount of cytoplasmic staining when compared to normal tissue. LIMPII staining appeared similar in both malignant and non-malignant tissue, however enlarged LIMPII positive vesicular structures were observed in malignant tissue when compared to control tissue.

Example 8—Diagnosis of Prostate Cancer and Treatment Options on the Basis of the Diagnostic/Prognostic Potential of the Marker(s)

A diagnosis of the present of prostate cancer may be made upon the basis of one or more of the level of mRNA expression of one or more of the mRNAs for any of the markers as described herein, the level of the marker proteins as described herein, the secretion of the marker proteins as described herein, the presence of the marker proteins in a biological fluid as described herein, or on the basis of immunohistology on tissue or biopsy samples of any of the marker proteins as described herein.

Examples of selected markers that may used include one or more of the following proteins or their mRNAs: CATHEPSIN B, CAPTHESIN D, α-GALACTOSIDASE, RAB7, LIMP-1, LIMP-2, TFR1, TFR2, STAMP2, SORT1 (SORTILIN), APPL1, EEA-1, LAMP-1, RAB4, APPL2, RAB5, RAB11, MPR, PAP, ACTIN, M6PR, IGFR2, MYO1B, PDCD6IP, SDCBP, SDC1, STX7, STX12, FGF1, FGF2, FGF3, FGFR1, FGFR2, FGFR3, NOX2, and NOX4.

For example, a cylindrical sample (biopsy) of prostate tissue may be removed through the rectum, using hollow needles, and a portion of the sample prepared for histology and immunohistochemistry. If the prostate is surgically removed, a pathologist may prepare a slice the prostate for analysis.

APPL1 may be selected as a suitable marker and analysis conducted as described in Example 1 using immunohistochemistry to determine the distribution of APPL1 using an APPL1 specific antibody. APPL1 delineates the cancer margins and shows dramatically increased staining within the tumour mass. Such staining would be indicative of the presence of prostate cancer.

On the basis of the detection using a selected marker as described herein, a variety of treatment options are available, dependent upon the diagnosis and/or prognosis and the extent of recurrence of the cancer, in addition to, or in conjunction with, the prognostic value of the selected markers described herein:

(i) Low Risk of Recurrence:

Treatment for patients with clinical stage T1-T2a, Gleason score 2-6, PSA <10 ng/mL, with a life expectancy <10 y, includes active surveillance Treatment for patients with a life expectancy ≥10 y includes active surveillance, or radical prostatectomy (RP) with or without pelvic lymph node dissection (PLND) if predicted probability of lymph node metastases ≥2%; RP being a standard therapy for localized prostate cancer, involving the removal of the prostate and seminal vesicles with or without pelvic lymph nodes; this may be done using either open or laparoscopic (robotic-assisted) technique; or Radiation therapy for patients with localized disease, and 3-dimensional (3D) techniques such as 3D conformal radiation treatment (3D-CRT), which offer benefits such as reduced toxicity and the use of higher doses; second-generation techniques, including intensity-modulated radiation therapy (IMRT), may also be required, especially if doses ≥78Gy are administered.

Radiation therapy doses of 75.6-79Gy in conventional 36-41 fractions to the prostate with 3D-CRT/IMRT with daily image-guided radiotherapy (IGRT) or brachytherapy (recommended dose rate: 145Gy for iodine-125 and 125Gy for palladium-103).

Patients with low-risk cancer are typically not candidates for pelvic lymph node irradiation or androgen deprivation therapy (ADT).

(ii) Intermediate Risk of Recurrence:

Treatment for patients with clinical stage T2b-T2c, Gleason score 7, PSA 10-20 ng/mL, who have a life expectancy <10 y, include active surveillance; or Radiation therapy (doses of 78-80+Gy) with 3D-CRT/IMRT with daily IGRT with or without short-term neoadjuvant/concomitant/adjuvant ADT for 4-6 months with or without brachytherapy (recommended dose rate: 145Gy for iodine-125 and 125Gy for palladium-103).

Treatment recommendations for patients with a life expectancy ≥10 y includes RP with PLND if predicted probability of lymph node metastasis ≥2% or radiation therapy (doses of 78-80+Gy) with 3D-CRT/IMRT with daily IGRT with or without short-term neoadjuvant/concomitant/adjuvant ADT for 4-6 months with or without brachytherapy (recommended dose rate: 145Gy for iodine-125 and 125Gy for palladium-103).

Intermediate-risk cancers consider combining brachytherapy (recommended dose rate: 145Gy for iodine-125 and 125Gy for palladium-103) with EBRT (40-50Gy) with or without 4-6 mo neoadjuvant/concomitant/adjuvant ADT.

Administering ADT before, during, and after radiation prolongs survival in patients.

(iii) High Risk of Recurrence:

Clinical stage T3a, Gleason score 8-10, PSA >20 ng/mL

Treatment options include radiation therapy (doses of 78-80+Gy) with 3D-CRT/IMRT plus long-term neoadjuvant/concomitant/adjuvant ADT for 2-3 y, or radiation therapy (doses of 78-80+Gy) with 3D-CRT/IMRT with daily IGRT plus brachytherapy (recommended dose rate: 145Gy for iodine-125 and 125Gy for palladium-103) with or without short-term neoadjuvant/concomitant/adjuvant ADT for 4-6 months, or RP plus PLND for selected patients with no fixation.

High-risk cancers may be treated with combination EBRT (40-50Gy) and brachytherapy with or without 4-6 months neoadjuvant/concomitant/adjuvant ADT.

Reference to any prior art in this specification is not, and should not be taken as, an acknowledgment or any form of suggestion that this prior art forms part of the common general knowledge in any country.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein, the singular forms "a", "an" and "the" include plural aspects unless the context already dictates otherwise.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The subject headings used herein are included only for the ease of reference of the reader and should not be used to limit the subject matter found throughout the disclosure or the claims. The subject headings should not be used in construing the scope of the claims or the claim limitations.

Future patent applications may be filed on the basis of the present application, for example by claiming priority from the present application, by claiming a divisional status and/or by claiming a continuation status. It is to be understood that the following claims are provided by way of example only, and are not intended to limit the scope of what may be claimed in any such future application. Nor should the claims be considered to limit the understanding of (or exclude other understandings of) the present disclosure. Features may be added to or omitted from the example claims at a later date.

Although the present disclosure has been described with reference to particular examples, it will be appreciated by those skilled in the art that the disclosure may be embodied in many other forms.

The invention claimed is:

1. A method of diagnosing and treating a prostate cancer in a subject, the method comprising:
   detecting APPL1 and SDC1 in a sample obtained from the subject;
   determining the ratio of the level of APPL1 to the level of SDC1 in the sample;
   comparing the ratio of the level of APPL1 to the level of SDC1 in the sample to the ratio of the level of APPL1 to the level of SDC1 in a non-malignant tissue to obtain an indication of prostate cancer in the subject, wherein an increased ratio of APPL1 to SDC1 in the sample as compared to the non-malignant tissue is indicative of prostate cancer in the subject; and
   administering to the subject having prostate cancer an effective amount of a therapeutic agent.

2. The method according to claim 1, wherein the method further comprises detecting one or more of an early endosomal marker, a late endosomal marker, a marker associated with endosomal biogenesis, a marker associated with endosomal trafficking and a marker associated with endosomal recycling.

3. The method according to claim 2, wherein the further marker is selected from one or more of SORT1, M6PR (CD-MPR), IGF2R (CI-MPR), PDC6IP (ALIX), and MYO1B (Myosin 1B).

4. The method of claim 1, wherein the detecting and/or determining steps involve immunological methods, including ELISA, staining and visualization with an antibody, immunohistochemistry, and/or flow cytometric detection.

5. A method of diagnosing and treating a prostate cancer in a subject, the method comprising:
   detecting SDC1 and SORT1 in a sample obtained from the subject;
   determining the ratio of the level of SDC1 to the level of SORT1 in the sample;
   comparing the ratio of the level of SDC1 to the level of SORT1 in the sample to the ratio of the level of SDC1 to the level of SORT1 in a non-malignant tissue to obtain an indication of prostate cancer in the subject, wherein an increased ratio of SDC1 to SORT1 in the sample as compared to the non-malignant tissue is indicative of prostate cancer in the subject; and
   administering to the subject having prostate cancer an effective amount of a therapeutic agent.

6. The method according to claim 5, wherein the method further comprises detecting one or more of an early endosomal marker, a late endosomal marker, a marker associated with endosomal biogenesis, a marker associated with endosomal trafficking and a marker associated with endosomal recycling.

7. The method according to claim 6, wherein the further marker is selected from one or more of APPL1, M6PR (CD-MPR), IGF2R (CI-MPR), PDC6IP (ALIX), and MYO1B (Myosin 1B).

8. The method according to claim 5, wherein the increased ratio of SDC1 to SORT1 is indicative of an increased relapse rate and/or decreased survival rate.

9. A method of determining the progression of and treating prostate cancer in a subject, the method comprising:
   detecting APPL1 and SDC1 in a sample obtained from the subject;
   determining the ratio of the level of APPL1 to the level of SDC1 in the sample;
   comparing the ratio of the level of APPL1 to the level of SDC1 in the sample to the ratio of the level of APPL1 to the level of SDC1 in a non-malignant tissue to obtain an indication of prostate cancer in the subject, wherein an amount of increase in the ratio of APPL1 to SDC1 in the sample is an indication of the progression of prostate cancer in the subject; and
   administering to the subject having prostate cancer an effective amount of a therapeutic agent in response to the indication of progression.

10. The method according to claim 9, wherein the method further comprises detecting one or more of an early endosomal marker, a late endosomal marker, a marker associated with endosomal biogenesis, a marker associated with endosomal trafficking and a marker associated with endosomal recycling.

11. The method according to claim 10, wherein the further marker is selected from one or more of SORT1, M6PR (CD-MPR), IGF2R (CI-MPR), PDC6IP (ALIX), and MYO1B (Myosin 1B).

\* \* \* \* \*